United States Patent
Gambacorti-Passerini et al.

(10) Patent No.: US 9,708,279 B2
(45) Date of Patent: Jul. 18, 2017

(54) 2-ACYLAMINOTHIAZOLES FOR THE TREATMENT OF CANCER

(71) Applicants: UNIVERSITA' DEGLI STUDI DI MILANO-BICOCCA, Milan (IT); UNIVERSITÈ DE GENÈVE, Geneva (CH); UNIVERSITÈ CLAUDE BERNARD LYON 1, Villeurbanne (FR)

(72) Inventors: Carlo Gambacorti-Passerini, Monza (IT); Luca Mologni, Vedano Al Lambro (IT); Leonardo Scapozza, Genève (CH); William Bisson, Corvallis, OR (US); Peter Goekjian, Villeurbanne (FR); Joseph D'Attoma, Villeurbanne (FR)

(73) Assignees: UNIVERSITÁ DEGLI STUDI DI MILANO—BICOCCA, Milan (IT); UNIVERSITÈ DE GENÈVE, Geneva (CH); UNIVERSITÈ CLAUDE BERNARD LYON 1, Villeurbanne (FR)

( * ) Notice: Subject to any disclaimer, the term of this patent is extended or adjusted under 35 U.S.C. 154(b) by 0 days.

(21) Appl. No.: 14/902,319

(22) PCT Filed: Jul. 3, 2014

(86) PCT No.: PCT/EP2014/064197
§ 371 (c)(1),
(2) Date: Dec. 30, 2015

(87) PCT Pub. No.: WO2015/001024
PCT Pub. Date: Jan. 8, 2015

(65) Prior Publication Data
US 2016/0257658 A1    Sep. 8, 2016

(30) Foreign Application Priority Data
Jul. 4, 2013 (IT) .............. MI2013A1124

(51) Int. Cl.
| | | |
|---|---|---|
| C07D 277/46 | (2006.01) |
| C07D 417/12 | (2006.01) |
| C07D 417/14 | (2006.01) |
| C07F 7/08 | (2006.01) |
| C07F 7/18 | (2006.01) |
| A61K 31/421 | (2006.01) |
| A61K 31/427 | (2006.01) |
| A61K 31/496 | (2006.01) |
| A61K 31/5377 | (2006.01) |

(52) U.S. Cl.
CPC ......... *C07D 277/46* (2013.01); *C07D 417/12* (2013.01); *C07D 417/14* (2013.01); *C07F 7/0812* (2013.01); *C07F 7/1856* (2013.01)

(58) Field of Classification Search
None
See application file for complete search history.

(56) References Cited

FOREIGN PATENT DOCUMENTS

| EP | 2107054 A1 | 10/2009 |
|---|---|---|
| WO | WO 2012/106540 A1 | 8/2012 |
| WO | WO 2013/017989 A1 | 2/2013 |

OTHER PUBLICATIONS

Cancer Drug Design and Discovery, Neidle, Stephen, ed. (Elsevier/Academic Press), pp. 427-431 (2008).*
Shaw et al. Clin. Cancer Res. vol. 17 p. 2081-2086(2011).*
Sullivan Ther. Adv. Med. Oncol. 2016, vol. 8(1) 32-47.*
Wu et al. Journal of Hematology & Oncology, 9:19 p. 1-7 (2016).*
International Search Report and Written Opinion of International Patent Application No. PCT/EP2014/064197 dated Aug. 18, 2014.

* cited by examiner

*Primary Examiner* — Emily Bernhardt
(74) *Attorney, Agent, or Firm* — Arent Fox LLP

(57) ABSTRACT

The present invention relates to inhibitors of the oncogenic protein kinase ALK of formula (I):

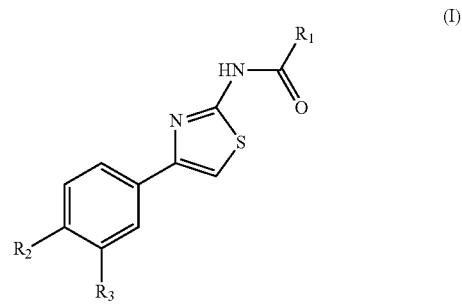

as herein described and pharmaceutical compositions thereof. The compounds of formula (I) are useful in the preparation of a medicament, in particular for the treatment of cancer.

9 Claims, No Drawings

2-ACYLAMINOTHIAZOLES FOR THE TREATMENT OF CANCER

CROSS-REFERENCE TO RELATED APPLICATION

This application is a 35 U.S.C. National Phase of PCT Application Ser. No. PCT/EP2014/064197, entitled "2-ACYLAMINOTHIAZOLES FOR THE TREATMENT OF CANCER," filed Jul. 3, 2014, which claims priority to Italian Patent Application No. MI2013A001124, entitled "2-ACYLAMINOTHIAZOLES FOR THE TREATMENT OF CANCER," filed on Jul. 4, 2013, which is expressly incorporated by reference herein in its entirety.

The present invention relates to 2-acylaminothiazole derivatives having ALK kinase inhibitory activity and to their pharmaceutical uses.

Such inhibitors can be used for the treatment of hyperproliferative diseases such as cancer, in particular for the treatment of ALK fusion protein positive cancers, such as anaplastic large cell lymphoma (ALCL), diffuse large B cell lymphoma, inflammatory myofibroblastic tumours, non-small cell lung cancer (NSCLC), oesophageal squamous cell carcinoma, renal medullary carcinoma, myeloid leukaemia, breast cancer and colorectal carcinoma.

BACKGROUND OF THE INVENTION

Cancer results from the subversion of processes that control the normal growth, location and mortality of cells. This loss of normal control mechanisms arises from the acquisition of mutations that lead to the oncogenic activation of proteins that are involved in the normal regulation of such processes.

Protein kinases are enzymes that catalyse the transfer of phosphate from adenosine-5'-triphosphate (ATP) to specific amino acid residues in many proteins. Generally, the phosphorylation of a protein changes its functionality, from inactive to active in some cases, and from active to inactive in others. Protein kinases are thus involved in the regulation of many aspects of cell function, as most of the signal transduction pathways controlling cell growth, survival, differentiation and motility are mediated by phosphorylation. Abnormal activity of protein kinases has been implicated in many cancers as well as in other diseases. The human genome encodes at least 518 kinases, of which approximately 90 specifically phosphorylate the phenolic hydroxyl of tyrosine residues. Tyrosine kinases are particularly involved in cell proliferation and survival processes, and their aberrant activation most often leads to oncogenic transformation.

For example, structural alterations in ALK produced by the chromosomal rearrangement t(2q23;5q35) generates the NPM/ALK oncogenic fusion protein associated with ALCL (Rabbitss, T. H. Nature, 1994,372, 143).

Large cell lymphomas represent about 25% of all non-Hodgkin's lymphomas; about one-third of these tumors are anaplastic large cell lymphoma (ALCL). In turn, the majority of ALCL patients (60-80%) possess a chromosomal translocation that leads to the in-frame juxtaposition of the 5' portion of the nucleophosmin (NPM) gene with the sequence encoding for the catalytic domain of ALK kinase. The resulting chimaeric gene, under the control of the strong NPM promoter, drives the expression of the NPM/ALK oncogenic fusion protein. An additional 10% of ALCL patients carry other ALK fusion proteins. To date, 11 ALK fusions have been described. In all cases, the ALK kinase domain sequence is fused to an aminoterminal protein-protein interaction domain of a protein that is highly expressed in the target cell. Thus, the fusion partner provides constitutive expression (through its promoter) and activation (via oligomerisation). In addition, ALK fusion proteins show anomalous cellular localisation. For example, NPM/ALK is mainly found in the cytoplasm and the nucleus. By contrast, wild-type ALK is a tightly regulated, integral membrane protein that is only activated in the presence of a specific extracellular ligand.

About 5-8% of NSCLC patients carry the EML4/ALK fusion. As with NPM/ALK, the 5' fusion partner EML4 provides high expression and constitutive activation of the ALK kinase. The population of ALK+NSCLC patients, although representing a minority of all NSCLC patients, is estimated to be about 50-70,000 new cases worldwide each year. In addition to fusion proteins, activating point mutants of ALK have been described and validated in familial (90% of cases) and sporadic (~10%) neuroblastoma and in anaplastic thyroid carcinoma (10% of patients).

ALK is normally expressed in the nervous system during embryonic development and is strongly down-regulated at birth, resulting in barely detectable levels in adult tissues. It has been extensively demonstrated that constitutively active NPM/ALK is a potent oncogene with transforming and tumourigenic properties (Morris et al., Science, 1994, 263, 1281-1284).

Moreover, rearrangement of ALK kinase is a very early event in tumour formation and is necessary for survival of transformed cells. The high level of expression of NPM/ALK and other ALK fusion protein variants in lymphoma cells and their direct role in lymphomagenesis, combined with the fact that normal ALK is expressed at low levels in the human body, suggests that ALK could potentially be an ideal target for therapy.

There is currently only one drug clinically available for the treatment of ALK-positive cancer. Crizotinib is a dual MET/ALK inhibitor recently approved for ALK+ NSCLC. It potently inhibits ALK phosphorylation and induces apoptosis in ALK+ cancer cells. Initial clinical trials showed excellent activity and tolerability in advanced NSCLC patients (Shaw et al., Lancet Oncol 2011; 12: 1004-12) However, clinical resistance develops in a significant fraction of patients (Choi et al., N Engl J Med 2010; 363: 1734-9). At least half of the patients show either amplification of ALK gene or acquisition of a secondary mutation that renders ALK insensitive to Crizotinib. In particular, the gatekeeper mutant L1196M showed high resistance to Crizotinib. Therefore, there is urgent need for second-generation compounds, with higher potency and selectivity, able to inhibit Crizotinib-resistant mutants and to circumvent clinical resistance. Moreover, it would be desirable to develop compounds which are non-ATP competitive.

DETAILED DESCRIPTION OF THE INVENTION

This invention provides compounds of formula (I)

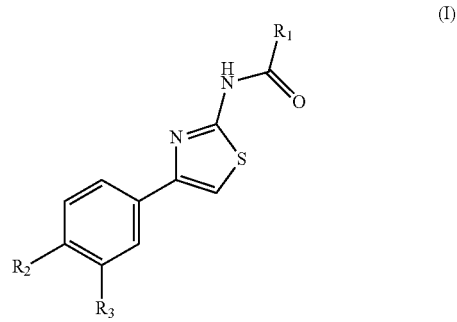

(I)

Wherein:
—$R_1$ is

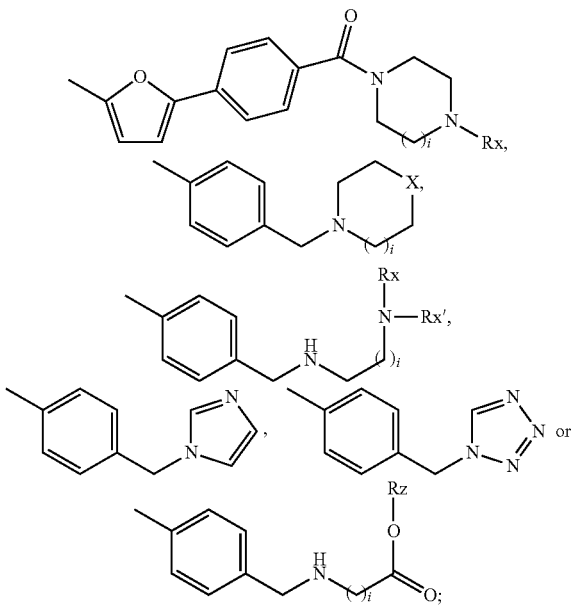

i equals zero, 1 or 2

Rx and Rx' can be the same or different and are a $C_1$-$C_3$ linear or branched alkyl;

X is either oxygen or NRy;

Ry is a $C_1$-$C_3$ linear or branched alkyl or propargyl;

Rz is either hydrogen or $C_1$-$C_3$ linear or branched alkyl;

—$R_2$ and —$R_3$ can be the same or different and are hydrogen, linear or branched $C_1$-$C_3$ alkyl or —C≡C—$R_4$, provided that at least one of —$R_2$ and —$R_3$ is —C≡C—$R_4$;

—R4 is hydrogen, —$CH_2$—O—$CPh_3$, cyclohexenyl, $C_1$-$C_4$ alkyl,

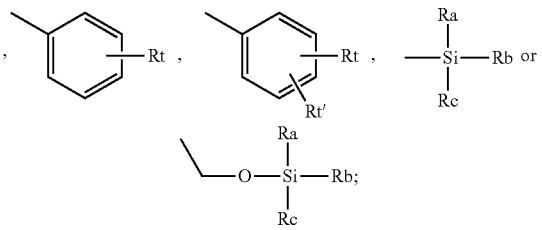

Rt and Rt' can be the same or different and are $C_1$-$C_3$ alkyl optionally substituted with one or more fluorine atoms, $C_1$-$C_3$ alkoxy optionally substituted with one or more fluorine atoms or F;

Ra, Rb and Rc can be the same or different and can be phenyl or $C_1$-$C_4$ linear or branched alkyl;

and pharmaceutically acceptable salts thereof.

In one embodiment (embodiment A1), both —$R_2$ and —$R_3$ are —C≡C—$R_4$ and $R_1$,$R_4$,Ra, Rb, Rc, Rt, Rt', Rx, Rx', Ry, Rz, X and i are as defined under formula (I).

In another embodiment (embodiment A2), $R_2$ is hydrogen or linear or branched $C_1$-$C_3$ alkyl; $R_3$ is —C≡C—$R_4$ and $R_1$,$R_4$,Ra, Rb, Rc, Rt, Rt', Rx, Rx', Ry, Rz, X and i are as defined under formula (I).

In a particular aspect of embodiment A2 (embodiment A2a), $R_2$ is hydrogen or methyl.

In a particular aspect of embodiment A2 (embodiment A2b), $R_2$ is hydrogen.

In a particular aspect of embodiment A2 (embodiment A2c), $R_2$ is methyl.

In another embodiment (embodiment A3), —$R_2$ is —C≡C—$R_4$; $R_3$ is hydrogen or linear or branched $C_1$-$C_3$ alkyl and $R_1$,$R_4$,Ra, Rb, Rc, Rt, Rt', Rx, Rx', Ry, Rz, X and i are as defined under formula (I).

In a particular embodiment of embodiment A3 (embodiment A3a), $R_3$ is hydrogen or methyl.

In a particular embodiment of embodiment A3 (embodiment A3b), $R_3$ is hydrogen.

In a particular embodiment of embodiment A3 (embodiment A3c), $R_3$ is methyl.

In other embodiments (embodiments B1), i equals 1 and $R_1$,$R_2$,$R_3$,$R_4$,Ra, Rb, Rc, Rt, Rt', Rx, Rx', Ry, Rz and X are, as the case may be, as defined under formula (I) or embodiments A1, A2 or A3.

In other embodiments (embodiments C1) —R4 is selected form the list of

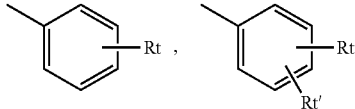

and $R_1$, $R_2$, $R_3$, Rt, Rt', Rx, Rx', Ry, Rz, X and i are, as the case may be, defined as under formula (I) or embodiments A1, A2,A2a,A2b,A2c,A3,A3a,A3b,A3c or B1

In particular aspects of embodiments C1 (embodiments C2), —R4 is selected from the list of

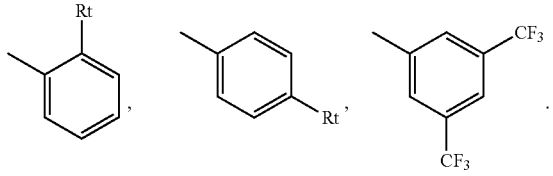

In particular aspect of embodiments C1 or C2 (embodiments C3), Rt is methyl, methoxy, trifluoromethyl, difluoromethyl, trifluoromethoxy, difluoromethoxy or F.

In more particular aspects of embodiments C1 or C2 (embodiments C4), Rt is methyl, methoxy, trifluoromethyl, trifluoromethoxy or F.

In particular aspects of embodiments C3 and C4 (embodiments C5), —R4 is

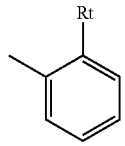

In other particular aspects of embodiments C3 and C4 (embodiments C6), —R4 is

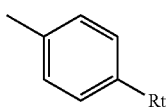

In particular aspects of embodiments C5 (embodiments C7), trifluoromethyl, trifluoromethoxy or F.

In particular aspects of embodiments C6 (embodiments C8), Rt is methyl, methoxy or F.

In other embodiments (embodiments D1), —R4 is selected from the list of

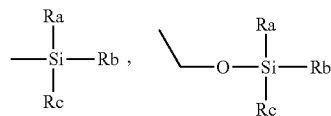

and $R_1, R_2, R_3$, Ra, Rb, Rc, Rx, Rx', Ry, Rz, X and i are, as the case may be, as defined under formula (I) or embodiments A1, A2, A2a, A2b, A2c, A3, A3a, A3b, A3c or B1.

In particular aspects of embodiments D1 (embodiments D2), Ra and Rb are the same and Rc is different from Ra and Rb.

In other particular aspects of embodiments D1 or D2 (embodiments D3), Ra and Rb are phenyl and Rc is a $C_1$-$C_4$ linear or branched alkyl.

In further particular aspects of embodiments D1 or D2 (embodiments D4), Ra, Rb and Rc are a $C_1$-$C_4$ linear or branched alkyl.

In further particular aspect of embodiments D1, D2, D3 or D4 (embodiments D5), —R4 is

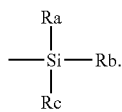

In further particular aspects of embodiments D1, D2, D3 or D4 (embodiments D6), —R4 is

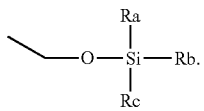

In other embodiments (embodiments E1), —$R_1$ is

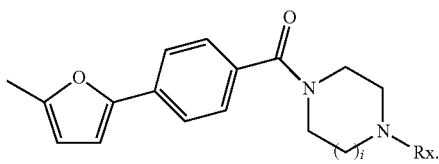

and $R_2$, $R_3$, $R_4$, Ra, Rb, Rc, Rt, Rt', Rx, Ry, and i are, as the case may be, as defined under formula (I) or embodiments A1, A2, A2a, A2b, A2c, A3, A3a, A3b, A3c, B1, C1, C2, C3, C4, C5, C6, C7,C8, D1, D2, D3, D4, D5, D6 or D7.

In particular aspects of embodiments E1 (Embodiments E1a), Rx is methyl.

In other embodiments (Embodiments E2), —R1 is

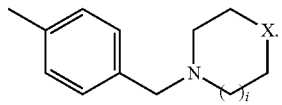

and $R_2$, $R_3$, $R_4$, Ra, Rb, Rc, Rt, Rt', Ry, X and i are, as the case may be, as defined under formula (I) or embodiments A1, A2, A2a, A2b, A2c, A3, A3a, A3b, A3c, B1, C1, C2, C3, C4, C5, C6, C7, C8, D1, D2, D3, D4, D5, D6 or D7.

In particular aspects of embodiments E2 (Embodiments E2a), X is oxygen.

In particular aspects of embodiments E2 (Embodiments E2b), X is NRy.

In particular aspects of embodiments E2b, Ry is methyl or propargyl.

In other embodiments (embodiments E3), —R1 is selected from

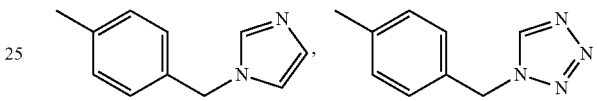

and $R_2$, $R_3$, $R_4$, Ra, Rb, Rc, Rt, Rt' and i are, as the case may be, as defined under formula (I) or embodiments A1, A2, A2a, A2b, A2c, A3, A3a, A3b, A3c, B1, C1, C2, C3, C4, C5, C6, C7, C8, D1, D2, D3, D4, D5, D6 or D7.

In other embodiments (embodiments E4), —R1 is

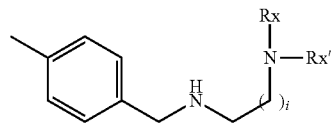

and $R_2$, $R_3$, $R_4$, Ra, Rb, Rc, Rt, Rt', Rx, Rx' and i are, as the case may be, as defined under formula (I) or embodiments A1, A2, A2a, A2b, A2c, A3, A3a, A3b, A3c, B1, C1, C2, C3, C4, C5, C6, C7, C8, D1, D2, D3, D4, D5, D6 or D7.

In particular aspects of embodiments E4 (embodiments E4a), Rx and Rx' are methyl.

In other embodiments (embodiments E5), —R1 is

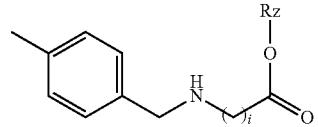

and $R_2$, $R_3$, $R_4$, Ra, Rb, Rc, Rt, Rt', Rz, and i are, as the case may be, as defined under formula (I) or embodiments A1, A2, A2a, A2b, A2c, A3, A3a, A3b, A3c, B1, C1, C2, C3, C4, C5, C6, C7,C8, D1, D2, D3, D4, D5, D6 or D7.

In particular embodiments of embodiments E5 (embodiments E5a), Rz is $C_1$-$C_3$ linear or branched alkyl.

Such compounds, in particular those where Rz is ethyl, may be used as prodrug forms of the corresponding carboxylic acid.

In particular aspects of embodiments E5 and E5a (embodiments E5b), Rx is isopropyl In particular embodiments of embodiments E5 (embodiments E5b), Rz is hydrogen.

In another embodiment, there is provided a compound selected from the list of 4-((4-methylpiperazin-1-yl)methyl)-N-(4-(3-(phenylethynyl)phenyl)thiazol-2-yl)benzamide;

4-((4-methylpiperazin-1-yl)methyl)-N-(4-(3-(p-tolylethynyl)phenyl)thiazol-2-yl)benzamide;

N-(4-(3-((4-methoxyphenyl)ethynyl)phenyl)thiazol-2-yl)-4-((4-methylpiperazin-1-yl)methyl)benzamide;

N-(4-(4-methyl-3-(phenylethynyl)phenyl)thiazol-2-yl)-4-((4-methylpiperazin-1-yl)methyl)benzamide N-(4-(4-methyl-3-(p-tolylethynyl)phenyl)thiazol-2-yl)-4-((4-methylpiperazin-1-yl)methyl)benzamide;

N-(4-(3-((4-methoxyphenyl)ethynyl)-4-methylphenyl)thiazol-2-yl)-4-((4-methylpiperazin-1-yl)methyl)benzamide;

N-(4-(4-methyl-3-((2-(trifluoromethyl)phenyl)ethynyl)phenyl)thiazol-2-yl)-4-((4-methylpiperazin-1-yl)methyl)benzamide;

N-(4-(3-((2-methoxyphenyl)ethynyl)-4-methylphenyl)thiazol-2-yl)-4-((4-methylpiperazin-1-yl)methyl)benzamide;

N-(4-(3-((4-fluorophenyl)ethynyl)-4-methylphenyl)thiazol-2-yl)-4-((4-methylpiperazin-1-yl)methyl)benzamide;

N-(4-(3-methyl-4-(p-tolylethynyl)phenyl)thiazol-2-yl)-4-((4-methylpiperazin-1-yl)methyl)benzamide;

N-(4-(3-methyl-4-((2-(trifluoromethyl)phenyl)ethynyl)phenyl)thiazol-2-yl)-4-((4-methylpiperazin-1-yl)methyl)benzamide;

4-((4-methylpiperazin-1-yl)methyl)-N-(4-(3-((2-(trifluoromethyl)phenyl)ethynyl)phenyl)thiazol-2-yl)benzamide;

N-(4-(3,4-bis((2-(trifluoromethyl)phenyl)ethynyl)phenyl)thiazol-2-yl)-4-((4-methylpiperazin-1-yl)methyl)benzamide;

N-(4-(4-methyl-3-((triisopropylsilyl)ethynyl)phenyl)thiazol-2-yl)-4-((4-methylpiperazin-1-yl)methyl)benzamide;

N-(4-(3-methyl-4-((triisopropylsilyl)ethynyl)phenyl)thiazol-2-yl)-4-((4-methylpiperazin-1-yl)methyl)benzamide;

N-(4-(3,4-bis((triisopropylsilyl)ethynyl)phenyl)thiazol-2-yl)-4-((4-methylpiperazin-1-yl)methyl)benzamide;

4-((4-methylpiperazin-1-yl)methyl)-N-(4-(3-((triethylsilyl)ethynyl)phenyl)thiazol-2-yl)benzamide;

4-((4-methylpiperazin-1-yl)methyl)-N-(4-(3-((trimethylsilyl)ethynyl)phenyl)thiazol-2-yl)benzamide;

N-(4-(3-(cyclohex-1-en-1-ylethynyl)phenyl)thiazol-2-yl)-4-((4-methylpiperazin-1-yl)methyl)benzamide;

N-(4-(3-(hex-1-yn-1-yl)phenyl)thiazol-2-yl)-4-(4-methylpiperazin-1-yl)methyl)benzamide;

N-(4-(3-(3-((tert-butyldiphenylsilyl)oxy)prop-1-yn-1-yl)phenyl)thiazol-2-yl)-4-((4-methylpiperazin-1-yl)methyl)benzamide;

4-((4-methylpiperazin-1-yl)methyl)-N-(4-(3-(3-((triisopropylsilyl)oxy)prop-1-yn-1-yl)phenyl)thiazol-2-yl)benzamide;

N-(4-(3-(3-((tert-butyldimethylsilyl)oxy)prop-1-yn-1-yl)phenyl)thiazol-2-yl)-4-((4-methylpiperazin-1-yl)methyl)benzamide;

N-(4-(3-((tert-butyldimethylsilyl)ethynyl)phenyl)thiazol-2-yl)-4-((4-methylpiperazin-1-yl)methyl)benzamide;

N-(4-(3-((tert-butyldiphenylsilyl)ethynyl)phenyl)thiazol-2-yl)-4-((4-methylpiperazin-1-yl)methyl)benzamide;

5-(4-(4-methylpiperazine-1-carbonyl)phenyl)-N-(4-(3-((triisopropylsilyl)ethynyl)phenyl)thiazol-2-yl)furan-2-carboxamide;

N-(4-(3-((tert-butyldimethylsilyl)ethynyl)phenyl)thiazol-2-yl)-5-(4-(4-methylpiperazine-1-carbonyl)phenyl)furan-2-carboxamide;

5-(4-(4-methylpiperazine-1-carbonyl)phenyl)-N-(4-(3-(3-((triisopropylsilyl)oxy)prop-1-yn-1-yl)phenyl)thiazol-2-yl)furan-2-carboxamide;

5-(4-(4-methylpiperazine-1-carbonyl)phenyl)-N-(4-(3-((2-(trifluoromethyl)phenyl)ethynyl)phenyl)thiazol-2-yl)furan-2-carboxamide;

4-((4-methylpiperazin-1-yl)methyl)-N-(4-(3-(3-(trityloxy)prop-1-yn-1-yl)phenyl)thiazol-2-yl)benzamide;

N-(4-(3-((2-fluorophenyl)ethynyl)phenyl)thiazol-2-yl)-4-((4-methylpiperazin-1-yl)methyl)benzamide;

N-(4-(3-((4-fluorophenyl)ethynyl)phenyl)thiazol-2-yl)-4-((4-methylpiperazin-1-yl)methyl)benzamide;

N-(4-(3-((3,5-bis(trifluoromethyl)phenyl)ethynyl)phenyl)thiazol-2-yl)-4-((4-methylpiperazin-1-yl)methyl)benzamide;

N-(4-(3-((3,5-bis(trifluoromethyl)phenyl)ethynyl)phenyl)thiazol-2-yl)-5-(4-(4-methylpiperazine-1-carbonyl)phenyl)furan-2-carboxamide;

4-((4-methylpiperazin-1-yl)methyl)-N-(4-(4-((triisopropylsilyl)ethynyl)phenyl)thiazol-2-yl)benzamide;

N-(4-(4-((3,5-bis(trifluoromethyl)phenyl)ethynyl)phenyl)thiazol-2-yl)-4-((4-methylpiperazin-1-yl)methyl)benzamide;

N-(4-(4-((tert-butyldimethylsilyl)ethynyl)phenyl)thiazol-2-yl)-4-((4-methylpiperazin-1-yl)methyl)benzamide;

4-(morpholinomethyl)-N-(4-(3-((triisopropylsilyl)ethynyl)phenyl)thiazol-2-yl)benzamide;

N-(4-(3-((3,5-bis(trifluoromethyl)phenyl)ethynyl)phenyl)thiazol-2-yl)-4-(morpholinomethyl)benzamide;

N-(4-(3-((tert-butyldimethylsilyl)ethynyl)phenyl)thiazol-2-yl)-4-(morpholinomethyl)benzamide;

N-(4-(3-((tert-butyldiphenylsilyl)ethynyl)phenyl)thiazol-2-yl)-4-(morpholinomethyl)benzamide;

4-((4-methylpiperazin-1-yl)methyl)-N-(4-(3-((2-(trifluoromethoxy)phenyl)ethynyl)phenyl)thiazol-2-yl)benzamide;

5-(4-(4-methylpiperazine-1-carbonyl)phenyl)-N-(4-(3-((2-(trifluoromethoxy)phenyl)ethynyl)phenyl)thiazol-2-yl)furan-2-carboxamide;

4-(((2-(dimethylamino)ethyl)amino)methyl)-N-(4-(3-((triisopropylsilyl)ethynyl)phenyl)thiazol-2-yl)benzamide;

4-((1H-tetrazol-1-yl)methyl)-N-(4-(3-((triisopropylsilyl)ethynyl)phenyl)thiazol-2-yl)benzamide;

4-((1H-imidazol-1-yl)methyl)-N-(4-(3-((triisopropylsilyl)ethynyl)phenyl)thiazol-2-yl)benzamide;

isopropyl 2-((4-((4-(3-((triisopropylsilyl)ethynyl)phenyl)thiazol-2-yl)carbamoyl)benzyl)amino)acetate;

4-((4-methylpiperazin-1-yl)methyl)-N-(4-(3-((triisopropylsilyl)ethynyl)phenyl)thiazol-2-yl)benzamide;

N-(4-(3-ethynylphenyl)thiazol-2-yl)-4-((4-methylpiperazin-1-yl)methyl)benzamide and 4-((4-(prop-2-yn-1-yl)piperazin-1-yl)methyl)-N-(4-(3-((triisopropylsilyl)ethynyl)phenyl)thiazol-2-yl)benzamide.

All embodiments may be combined.

GENERAL ROUTE TO COMPOUNDS OF THE INVENTION

When $R_2$ and/or $R_3$ are ethynyl, the compounds of the invention may be obtained by TBAF deprotection of their corresponding silyl ether, which can in turn be obtained as described below.

When only one of $-R_2$ and $-R_3$ is $-C{\equiv}C-R_4$, the compounds of the invention may be obtained as depicted in scheme 1 below Scheme 1

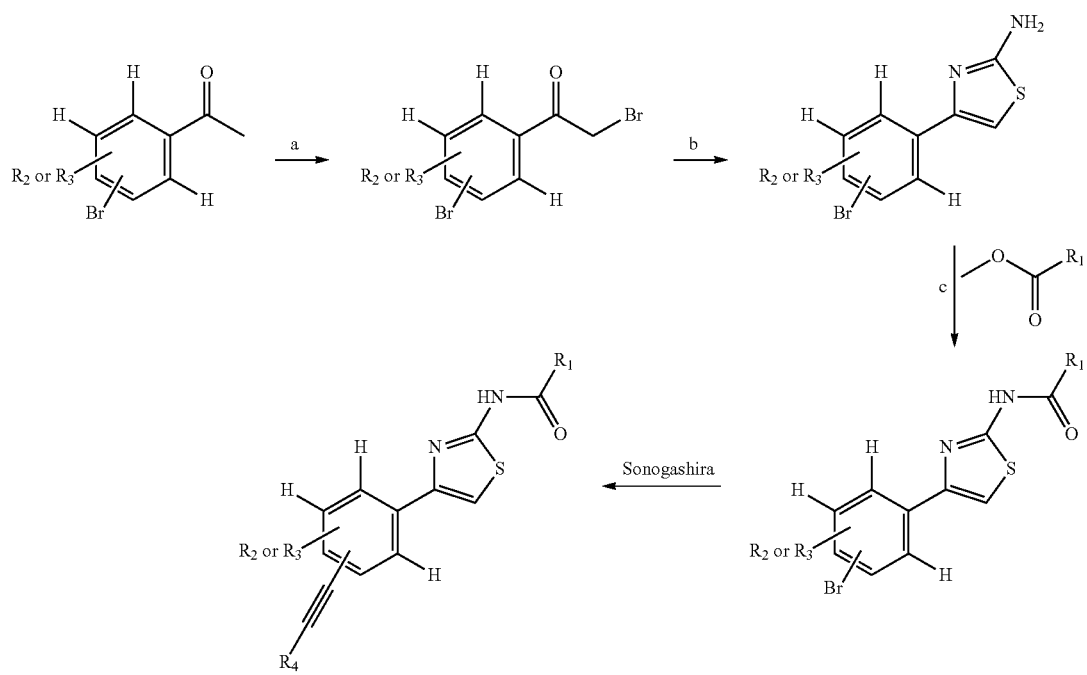

Reactants and conditions:
(a) CuBr$_2$, EtOAc, reflux; (b) thiourea, EtOH, reflux (c) AlMe$_3$, toluene, reflex Reactants and conditions: (a) CuBr$_2$, EtOAc, reflux; (b) thiourea, EtOH, reflux (c) AlMe$_3$, toluene, reflux Alternatively, and imperatively when —R$_1$ is

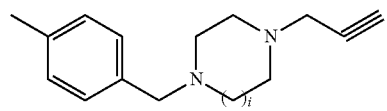

such compounds may be obtained by insertion of the R$_2$ or R$_3$ ethynyl derivative via a Sonogashira coupling as a first step, as depicted in scheme 2 below -continued

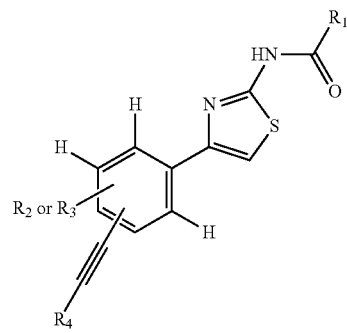

When both —R$_2$ and —R$_3$ are —C≡C—R$_4$ and —R$_2$ and —R$_3$ are the same, the compounds of this invention may be obtained similarly to those depicted in scheme 1 and 2 above, but starting from a di-halo derivative and by inserting both R$_2$ and R$_3$ via the Sonogashira reaction as depicted in schemes 3 and 4 below Scheme 2

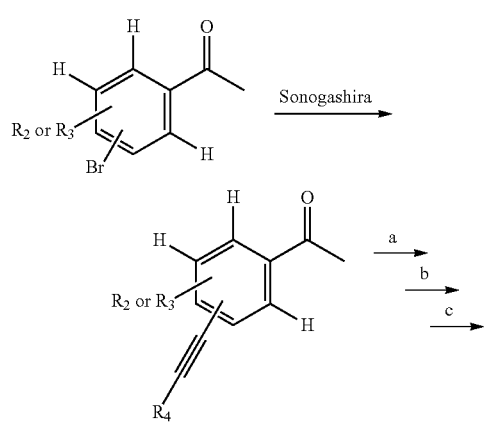

Scheme 3

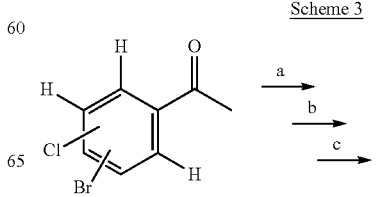

-continued

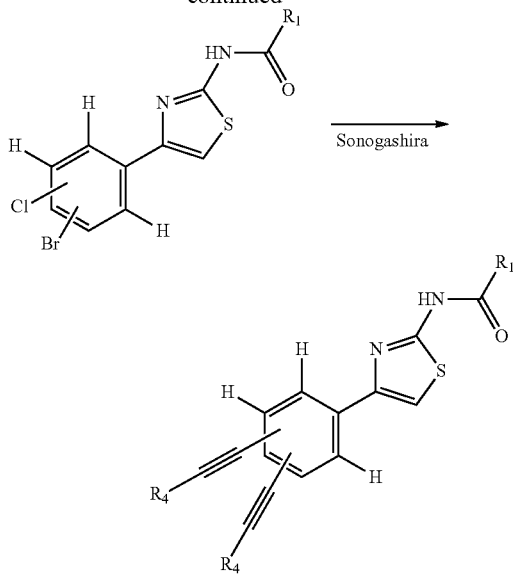

Scheme 4

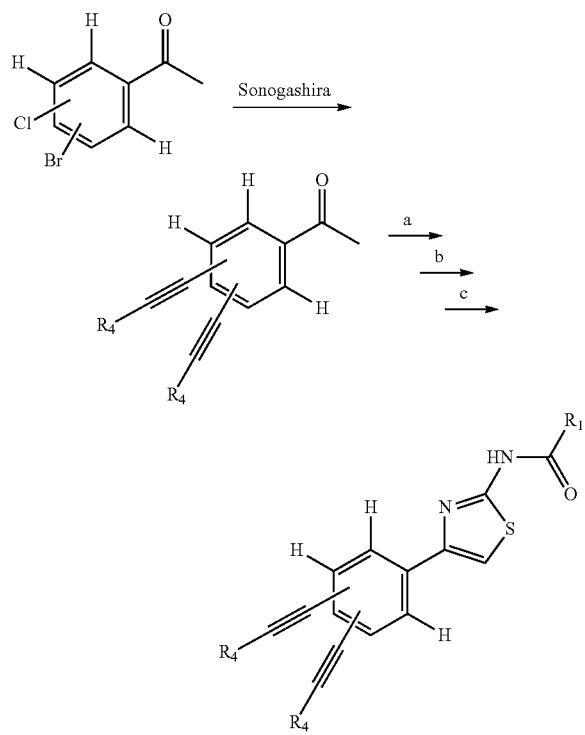

When both —R₂ and —R₃ are —C≡C—R₄ and they are not the same, such groups may be inserted sequentially into the above depicted di-halo precursor via a Sonogashira coupling, either by inserting the first group at the bromide-substituted carbon via a Sonogashira reaction under the Buchwald conditions using 1 equivalent of alkyne—which however may lead to the formation of a portion of unwanted disubstituted compound—and then performing a second Sonogashira coupling with the same conditions at the chlorine substituted atom, or by inserting the first group at the bromine-substituted carbon via a controlled copper and Pd(PPh₃)₄-catalysed Sonogashira reaction and the second group via a Sonogashira reaction at the chlorine atom under the Buchwald conditions.

BIOLOGICAL EVALUATION

The compounds of the invention may be tested in a relevant animal model or in the following assays.

ELISA-Based in vitro Kinase Assay

GST-tagged recombinant wild-type or L1196M mutated ALK kinase (rALK) was expressed in Sf9 insect cells using the pBacPAK baculovirus vector system (Clontech) and purified using Glutathione Sepharose 4B affinity beads (GE Healthcare). Recombinant 3C protease was used to remove the GST tag. Purified ALK was used to screen inhibitors in the ELISA-based kinase assay, as follows: Nunc-Immuno 96-well plates were incubated overnight at 30° C. with coating solution containing 2 µg of a specific ALK peptide substrate (ARDIYRASFFRKGGCAMLPVK) in PBS. Wells were then washed with 200 µL of wash buffer (PBS-Tween 0.05%) and incubated with 4% BSA in PBS for at least 2 h at 30° C. The kinase reaction was performed in the presence of 50 mM Tris pH 7.5, 5 mM $MnCl_2$, 5 mM $MgCl_2$, 0.3 mM ATP and purified rALK in a total volume of 100 µL/well at 30° C. for 15 min. For inhibitor testing the reaction mix was preincubated with inhibitor or vehicle for 10 min at room temperature before transferring to the ELISA plate. After the reaction, the wells were washed 5 times with 200 uL of wash buffer. Phosphorylated peptide was detected using 100 µL/well of a mouse monoclonal anti-phosphotyrosine antibody (clone 4G10 UpstateBiotech Ltd) diluted 1:2000 in PBS+4% BSA. After 30 min incubation at room temperature the antibody was removed and wells were washed as described above. 100 µL of a secondary antibody (anti-mouse IgG, Horseradish Peroxidase linked whole antibody, Amersham Pharmacia Biotech) diluted 1:1000 in PBS+4% BSA was added to each well and the plate was incubated again for 30 min at room temperature before washing as above. The plate was developed using 100 µL/well TMB Substrate Solution (Pierce) and the reaction was stopped by adding an equal volume of 1M $H_2SO_4$. Finally, the absorbance was read at 450 nm using an ELISA plate reader (Bio-Rad). The concentration of inhibitor showing 50% inhibition as compared with the control was expressed as $IC_{50}$ (µM).

Tritiated Thymidine Uptake Cell Proliferation Assay

The following procedure uses parental untransformed BaF3 cells, BaF3 cells transformed with the oncogenic fusion protein NPM/ALK, BaF3 cells transformed with the mutated oncogenic fusion protein NPM/ALK carrying the substitution L1196M, human NPM/ALK-positive SUDHL-1 and Karpas-299 cells, human ALK-negative U937 and HL-60 leukemic cells. The parent untransformed BaF3 cells and ALK-negative cells are used as controls. Cells are seeded in U-bottomed 96-well plates at 10 000 cells/well in a volume of 100 µL in supplemented medium. In the case of the parent untransformed BaF3 cells, the medium is supplemented with IL-3. Serial dilutions of inhibitors are added to the appropriate wells and volumes adjusted to 200 µL. Controls were treated with the equivalent volume of vehicle, DMSO, alone. Plates are incubated at 37° C. for 72 h. ³[H]-thymidine (1 µCiCi/well) is added for the last 8 h of incubation. Cells are harvested on to paper filters and ³[H]-thymidine incorporation is measured using a β scintillation counter (1430 MicroBeta, Wallac, Turku, Finland). The 50% inhibitory concentration ($IC_{50}$) is defined as the concentration of inhibitor, expressed in micromolar, that give a 50% decrease in $^3$[H]-thymidine uptake compared with controls.

FORMULATION AND ADMINISTRATION

Compounds under formula I are formulated preferably in admixture with a pharmaceutically acceptable carrier, excipient or the like. In general, it is preferable to administer the pharmaceutical composition in orally-administrable form, but certain formulations may be administered via a parenteral, intravenous, intramuscular, transdermal, buccal, subcutaneous, suppository, nasal or other route. One of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients. In certain pharmaceutical dosage forms, the pro-drug form of the compounds, especially including ester and ether derivatives, as well as various salt forms of the present compounds, are preferred. One of ordinary skill in the art will recognize how to readily modify the present compounds to pro- drug forms to facilitate delivery of active compounds to a targeted site within the host organism or patient. The routineer also will take advantage of favourable pharmacokinetic parameters of the pro-drug forms, where applicable, in delivering the present compounds to a targeted site within the host organism or patient to maximize the intended effect of the compound. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount effective to alleviate the symptoms of the subject being treated. While human dosage levels have yet to be optimized for the compounds of the invention, generally, a daily dose is from about 0.05 mg/kg to about 100 mg/kg of body weight. The amount of active compound administered will, of course, be dependent on the subject and disease state being treated, the severity of the affliction, the manner and schedule of administration and the judgment of the prescribing physician. For purposes of the present invention, a prophylactically or preventive effective amount of the compositions according to the present invention (i.e., an amount which substantially reduces the risk that a patient will either succumb to a disease state or condition or that the disease state or condition will worsen) falls within the same concentration range as set forth above for therapeutically effective amounts and is usually the same as a therapeutically effective amount. In some embodiments of the present invention, one or more compounds of formula (I) are administered in combination with one or more other pharmaceutically active agents. The phrase "in combination", as used herein, refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition. Rather, so long as both (or more) agents remain in the subject's body, they are considered to be administered "in combination".

EXAMPLES

Examples 1 to 50 below represent individual embodiments of this invention

General procedure D for Sonogashira coupling with $PdCl_2(CH_3CN)_2$:

At room temperature and under an inert atmosphere, the bromide moiety (1 eq.) was placed in a Schlenk tube, followed by the addition of $PdCl_2(CH_3CN)_2$ (0.08 eq.), 2-dicyclohexylphosphino-2',4',6'-triisopropylbiphenyl (0.16 eq.) and $Cs_2CO_3$ (2.6 eq.). The tube was evacuated and back-filled with argon (this was repeated three additional times). Acetonitrile (1 mL) was added and then the alkyne (2 eq.) was injected. The reaction mixture was allowed to stir at 90° C. overnight. Then the reaction mixture was cooled to room temperature. The mixture was diluted with DCM, filtered through Celite and washed with DCM. The organic layer was evaporated under reduced pressure.

General procedure E for Sonogashira coupling with $PdCl_2(CH_3CN)_2$:

At room temperature and under an inert atmosphere, the bromide moiety (1 eq.) was placed in a Schlenk tube, followed by the addition of $PdCl_2(CH_3CN)_2$ (0.16 eq.), 2-dicyclohexylphosphino-2',6'-dimethoxybiphenyl (0.32 eq.) and $Cs_2CO_3$ (5.2 eq.). The tube was evacuated and back-filled with argon (this was repeated three additional times). Acetonitrile (1 mL) was added and then the alkyne (2 eq.) was injected. The reaction mixture was allowed to stir at 90° C. overnight. Then the reaction mixture was cooled to room temperature. The mixture was diluted with DCM, filtered through Celite and washed with DCM. The organic layer was evaporated under reduced pressure.

General procedure F for Sonogashira coupling with $Pd(PPh_3)_4$:

At room temperature and under an inert atmosphere, the bromide moiety (1 eq.) was placed in a Schlenk tube, followed by the addition of $Pd(PPh_3)_4$ (0.05 equiv.), CuI (0.1 equiv.) and $K_3PO_4$ (1.1 equiv.). The tube was evacuated and back-filled with argon (this was repeated three additional times). THF (1 mL) was added and then the alkyne (2 equiv.) was injected. The reaction mixture was allowed to stir at 70° C. overnight. Then the reaction mixture was cooled to room temperature. The mixture was diluted with DCM, filtered through Celite and washed with DCM. The organic layer was evaporated under reduced pressure.

General procedure G for Sonogashira coupling with $PdCl_2(CH_3CN)_2$:

At room temperature and under an inert atmosphere, the bromide moiety (1 eq.) was placed in a Schlenk tube, followed by the addition of $PdCl_2(CH_3CN)_2$ (0.08 eq.), 2-dicyclohexylphosphino-2',4',6'-triisopropylbiphenyl (0.16 eq.) and $K_2CO_3$ (2 eq.). The tube was evacuated and back-filled with argon (this was repeated three additional times). Acetonitrile (1 mL) was added and then the alkyne (2 eq.) was injected. The reaction mixture was allowed to stir at 90° C. overnight. Then the reaction mixture was cooled to room temperature. The mixture was diluted with DCM, filtered through Celite and washed with DCM. The organic layer was evaporated under reduced pressure.

General procedure H for Sonogashira coupling with PdCl$_2$(CH$_3$CN)$_2$:

At room temperature and under an inert atmosphere, the bromide moiety (1 eq.) was placed in a Schlenk tube, followed by the addition of PdCl$_2$(CH$_3$CN)$_2$ (0.16 eq.), 2-dicyclohexylphosphino-2',4',6'-dimethoxybiphenyl (0.32 eq.) and K$_2$CO$_3$ (4 eq.). The tube was evacuated and back-filled with argon (this was repeated three additional times). Acetonitrile (1 mL) was added and then the alkyne (2 eq.) was injected. The reaction mixture was allowed to stir at 90° C. overnight. Then the reaction mixture was cooled to room temperature. The mixture was diluted with DCM, filtered through Celite and washed with DCM. The organic layer was evaporated under reduced pressure.

Example 1

4-((4-methylpiperazin-1-yl)methyl)-N-(4-(3-(phenyl-ethynyl)phenyl)thiazol-2-yl)benzamide

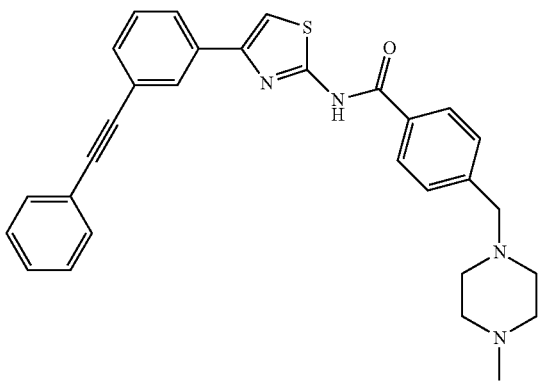 [SMILES: CN1CCN(Cc2ccc(C(=O)Nc3nc(-c4cccc(C#Cc5ccccc5)c4)cs3)cc2)CC1]

According the general procedure D using N-(4-(3-bromophenyl)thiazol-2-yl)-4-((4-methylpiperazin-1-yl)methyl)benzamide (30 mg, 0.063 mmol). Purification by silica gel flash chromatography (DCM/MeOH 85:15) afforded the product (19.6 mg, 64%) as a yellow viscous oil. $^1$H NMR (400 MHz, CDCl$_3$) δ 7.95 (dd, J=1.5, 1.5 Hz, 1H, Har), 7.85 (d, J=8.1 Hz, 2H, Har), 7.73 (dd, J=7.8, 1.5 Hz, 1H, Har), 7.58-7.53 (m, 2H, Har), 7.46-7.31 (m, 8H, Har), 7.23 (s, 1H, Har), 3.54 (s, 2H, CH$_2$), 2.48 (bs, 8H, 4×CH$_2$), 2.30 (s, 3H, CH$_3$). $^{13}$C NMR (101 MHz, CDCl$_3$) δ 165.1 (C), 159.0 (C), 149.6 (C), 144.3 (C), 134.7 (C), 132.0 (CH), 131.3 (CH), 131.0 (C), 129.7 (CH), 129.6 (CH), 129.1 (CH), 128.7 (CH), 127.8 (CH), 126.2 (CH), 124.1 (C), 123.5 (C), 109.0 (CH), 90.0 (C), 89.5 (C), 62.7 (CH$_2$), 55.3 (CH$_2$), 53.2 (CH$_2$), 46.2 (CH$_3$). HRMS [M+H]$^+$ C$_{30}$H$_{29}$N$_4$OS: Calcd. 493.2057 found 493.2059. Purity: 97.6%.

Example 2

4-((4-methylpiperazin-1-yl)methyl)-N-(4-(3-(p-tolyl-ethynyl)phenyl)thiazol-2-yl)benzamide

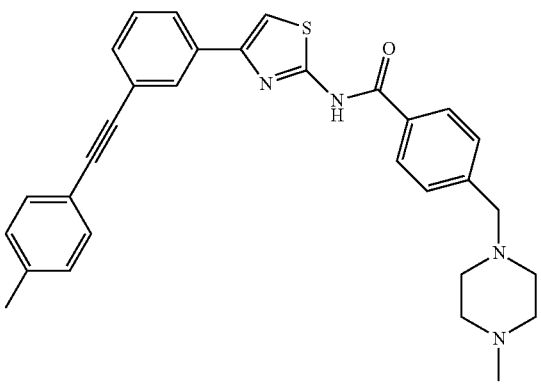 [SMILES: Cc1ccc(C#Cc2cccc(-c3csc(NC(=O)c4ccc(CN5CCN(C)CC5)cc4)n3)c2)cc1]

According the general procedure D using N-(4-(3-bromophenyl)thiazol-2-yl)-4-((4-methylpiperazin-1-yl)methyl)benzamide (30 mg, 0.063 mmol). Purification by silica gel flash chromatography (DCM/MeOH 85:15) afforded the product (13.2 mg, 42%) as a yellow viscous oil. $^1$H NMR (300 MHz, CDCl$_3$) δ 7.95 (dd, J=1.5,1.5 Hz, 1H, Har), 7.87 (d, J=8.2 Hz, 2H, Har), 7.73 (ddd, J=7.7, 2.8, 1.4 Hz, 1H), 7.47-7.40 (m, 6H, Har), 7.34 (dd, J=7.7, 7.7 Hz, 1H, Har), 7.23 (s, 1H, Har), 7.17 (d, J=8.0 Hz, 2H, Har), 3.56 (s, 2H, CH$_2$), 2.51 (bs, 8H, 4×CH$_2$), 2.38 (s, 3H, CH$_3$), 2.33 (s, 3H, CH$_3$). $^{13}$C NMR (75 MHz, CDCl$_3$) δ 165.0 (C), 158.9 (C), 149.6 (C), 144.3 (C), 138.9 (C), 134.7 (C), 131.9 (CH), 131.3 (CH), 130.9 (C), 129.7 (CH), 129.5 (CH), 129.5 (CH), 129.1 (CH), 109.0 (CH), 90.2 (C), 88.9 (C), 62.7 (CH$_2$), 55.3 (CH$_2$), 53.1 (CH$_2$), 46.1 (CH$_3$), 21.9 (CH$_3$). HRMS [M+H]$^+$ C$_{31}$H$_{31}$N$_4$OS: Calcd. 507.2213 found 507.2226. Purity: 96.6%.

Example 3

N-(4-(3-((4-methoxyphenyl)ethynyl)phenyl)thiazol-2-yl)-4-((4-methylpiperazin-1-yl)methyl)benzamide

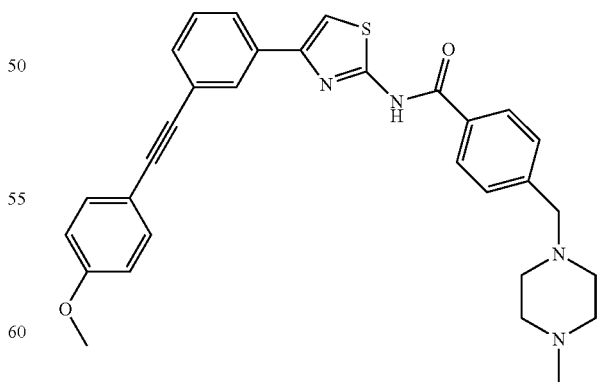

According the general procedure D using N-(4-(3-bromophenyl)thiazol-2-yl)-4-((4-methylpiperazin-1-yl)methyl)benzamide (30 mg, 0.063 mmol). Purification by silica gel flash chromatography (DCM/MeOH 85:15) afforded the product (15.2 mg, 47%) as a yellow viscous oil. $^1$H NMR (400 MHz, CDCl$_3$) δ 7.90 (dd, J=1.5, 1.5 Hz, 1H, Har), 7.83 (d, J=8.2 Hz, 2H, Har), 7.69 (dd, J=7.8, 2.8, 1.5 Hz, 1H), 7.48 (d, J=8.8 Hz, 2H, Har), 7.41-7.36 (m, 3H, Har), 7.30 (dd, J=7.7, 7.7 Hz, 1H, Har), 7.22 (s, 1H, Har), 6.89 (d, J=8.8 Hz, 2H, Har), 3.83 (s, 3H, CH$_3$), 3.53 (s, 2H, CH$_2$), 2.49 (bs, 8H, 4×CH$_2$), 2.31 (s, 3H, CH$_3$). $^{13}$C NMR (101 MHz, CDCl$_3$) δ 165.2 (C), 160.0 (C), 159.1 (C), 149.6 (C), 144.2 (C), 134.6 (C), 133.4 (CH), 131.1 (CH), 131.0 (C), 129.6 (CH), 129.4 (CH), 129.0 (CH), 127.8 (CH), 125.8 (CH), 124.3 (C), 115.6 (C), 114.4 (CH), 108.9 (CH), 90.1 (C), 88.2 (C), 62.7 (CH$_2$), 55.6 (CH$_3$), 55.3 (2×CH$_2$), 53.1 (2×CH$_2$), 46.1 (CH$_3$). HRMS [M+H]$^+$ C$_{31}$H$_{31}$N$_4$O$_2$S: Calcd. 523.2162 found 523.2157. Purity: 100%.

Example 4

N-(4-(4-methyl-3-(phenylethynyl)phenyl)thiazol-2-yl)-4-((4-methylpiperazin-1-yl)methyl)benzamide

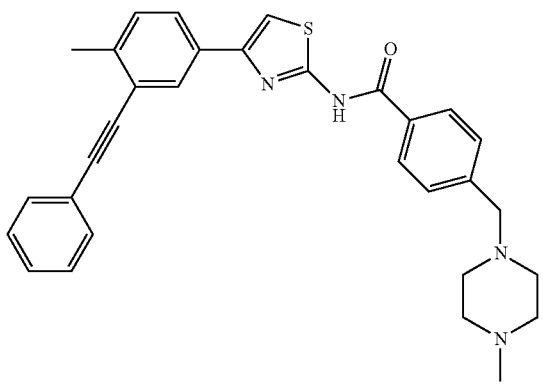 [SMILES: Cc1ccc(-c2csc(NC(=O)c3ccc(CN4CCN(C)CC4)cc3)n2)cc1C#Cc1ccccc1]

According the general procedure D using N-(4-(3-bromo-4-methylphenyl)thiazol-2-yl)-4-((4-methylpiperazin-1-yl)methyl)benzamide (32 mg, 0.066 mmol). Purification by silica gel flash chromatography (DCM/MeOH 85:15) afforded the product (21.3 mg, 64%) as a yellow viscous oil. $^1$H NMR (400 MHz, CDCl$_3$) δ 7.90 (d, J=1.7 Hz, 1H, Har), 7.85 (d, J=8.2 Hz, 2H, Har), 7.63 (dd, J=8.0, 1.8 Hz, 1H, Har), 7.55 (dd, J=7.2, 2.4 Hz, 2H, Har), 7.44-7.34 (m, 5H, Har), 7.21 (d, J=8.1 Hz, 1H, Har), 7.17 (s, 1H, Har), 3.55 (s, 2H, CH$_2$), 2.50 (s, 3H, CH$_3$), 2.48 (bs, 8H, 4×CH$_2$), 2.31 (s, 3H, CH$_3$). $^{13}$C NMR (101 MHz, CDCl$_3$) δ 165.0 (C), 158.9 (C), 149.7 (C), 144.3 (C), 140.2 (C), 132.2 (C), 131.9 (2×CH), 131.0 (C), 130.2 (CH), 129.9 (C), 129.8 (CH), 129.67 (CH), 129.26 (C), 128.73 (2×CH), 128.63 (CH), 127.78 (CH), 126.19 (CH), 123.8 (C), 108.2 (CH), 93.9 (C), 88.5 (C), 62.7 (CH$_2$), 55.3 (2×CH$_2$), 53.3 (2×CH$_2$), 46.2 (CH$_3$), 20.8 (CH$_3$). HRMS [M+H]$^+$ C$_{31}$H$_{30}$N$_4$OS: Calcd. 507.2217 found 507.2213. Purity: 92.6%.

Example 5

N-(4-(4-methyl-3-(p-tolylethynyl)phenyl)thiazol-2-yl)-4-((4-methylpiperazin-1-yl)methyl)benzamide

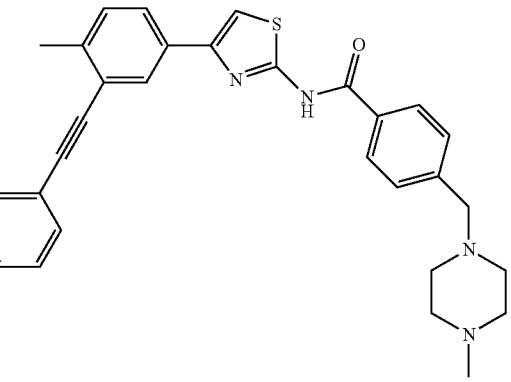

According the general procedure D using N-(4-(3-bromo-4-methylphenyl)thiazol-2-yl)-4-((4-methylpiperazin-1-yl)methyl)benzamide (32 mg, 0.066 mmol). Purification by silica gel flash chromatography (DCM/MeOH 85:15) afforded the product (21.2 mg, 62%) as a yellow viscous oil. $^1$H NMR (300 MHz, CDCl$_3$) δ 7.87 (d, J=1.8 Hz, 1H, Har), 7.83 (d, J=8.2 Hz, 2H, Har), 7.60 (dd, J=7.9, 1.8 Hz, 1H, Har), 7.45 (d, J=8.1 Hz, 2H, Har), 7.38 (d, J=8.2 Hz, 3H), 7.20-7.15 (m, 4H, Har), 3.54 (s, 2H, CH$_2$), 2.50 (s, 3H, CH$_3$), 2.48 (bs, 8H, 4×CH$_2$), 2.38 (s, 3H, CH$_3$), 2.31 (s, 3H, CH$_3$). $^{13}$C NMR (75 MHz, CDCl$_3$) δ 165.1 (C), 159.0 (C), 149.7 (C), 144.2 (C), 140.1 (C), 138.8 (C), 132.1 (C), 131.7 (2×CH), 131.0 (C), 130.1 (CH), 129.7 (CH), 129.6 (2×CH), 129.5 (2×CH), 127.8 (2×CH), 126.0 (CH), 123.9 (C), 120.6 (C), 108.1 (CH), 94.1 (C), 87.8 (C), 62.7 (CH$_2$), 55.3 (2×CH$_2$), 53.2 (2×CH$_2$), 46.2 (CH$_3$), 21.9 (CH$_3$), 20.8 (CH$_3$). HRMS [M+H]$^+$ C$_{32}$H$_{33}$N$_4$OS: Calcd. 521.2370 found 521.2373. Purity: 95.0%.

Example 6

N-(4-(3-((4-methoxyphenyl)ethynyl)-4-methylphenyl)thiazol-2-yl)-4-((4-methylpiperazin-1-yl)methyl)benzamide

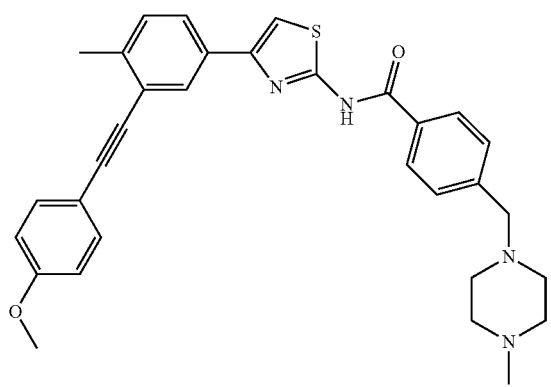 [SMILES: COc1ccc(C#Cc2cc(-c3csc(NC(=O)c4ccc(CN5CCN(C)CC5)cc4)n3)ccc2C)cc1]

According the general procedure D using N-(4-(3-bromo-4-methylphenyl)thiazol-2-yl)-4-((4-methylpiperazin-1-yl)

methyl)benzamide (30 mg, 0.062 mmol). Purification by silica gel flash chromatography (DCM/MeOH 85:15) afforded the product (12 mg, 36%) as a yellow viscous oil. $^1$H NMR (400 MHz, CDCl$_3$) δ 7.91 (d, J=1.7 Hz, 1H), 7.89 (d, J=8.2 Hz, 2H, Har), 7.63 (dd, J=7.9, 1.8 Hz, 1H, Har), 7.49 (d, J=8.7 Hz, 2H, Har), 7.45 (d, J=8.2 Hz, 2H, Har), 7.23 (d, J=8.0 Hz, 1H, Har), 7.17 (s, 1H, Har), 6.90 (d, J=8.8 Hz, 2H, Har), 3.84 (s, 3H, CH$_3$), 3.57 (s, 2H, CH$_2$), 2.53 (bs, 8H, 4×CH$_2$), 2.51 (s, 3H, CH$_3$), 2.34 (s, 3H, CH$_3$). $^{13}$C NMR (101 MHz, CDCl$_3$) δ 164.83 (C), 160.02 (C), 158.70 (C), 149.79 (C), 144.23 (C), 140.07 (C), 133.33 (2×CH), 132.21 (C), 131.03 (C), 130.17 (CH), 129.76 (2×CH), 129.62 (CH), 127.79 (2×CH), 125.88 (CH), 124.14 (C), 115.91 (C), 114.40 (2×CH), 108.14 (CH), 93.93 (C), 87.21 (C), 62.68 (CH$_2$), 55.68 (CH$_3$), 55.27 (2×CH$_2$), 53.08 (2×CH$_2$), 46.06 (CH$_3$), 20.87 (CH$_3$). HRMS [M+H]$^{30}$ C$_{32}$H$_{32}$N$_4$OS: Calcd. 537.2319 found 537.2324. Purity: 89.3%.

Example 7

N-(4-(4-methyl-3-((2-(trifluoromethyl)phenyl)ethynyl)phenyl)thiazol-2-yl)-4-((4-methylpiperazin-1-yl)methyl)benzamide

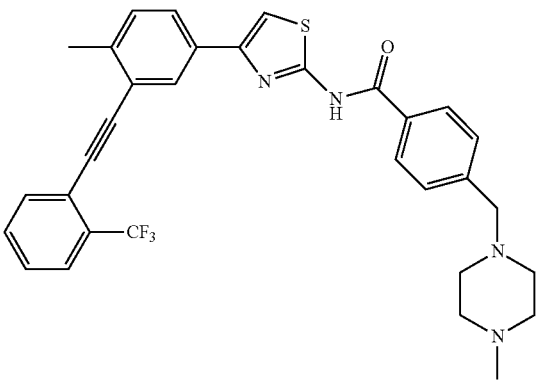 [SMILES: Cc1ccc(-c2csc(NC(=O)c3ccc(CN4CCN(C)CC4)cc3)n2)cc1C#Cc1ccccc1C(F)(F)F]

According the general procedure D using N-(4-(3-bromo-4-methylphenyl)thiazol-2-yl)-4-((4-methylpiperazin-1-yl)methyl)benzamide (30 mg, 0.062 mmol). Purification by silica gel flash chromatography (DCM/MeOH 85:15) afforded the product (19.6 mg, 56%) as a yellow viscous oil. $^1$H NMR (400 MHz, CDCl$_3$) δ 7.91 (d, J=1.7 Hz, 1H, Har), 7.85 (d, J=8.2 Hz, 2H, Har), 7.70 (dd, J=7.7, 3.7 Hz, 1H, Har), 7.65 (dd, J=8.0, 1.8 Hz, 1H, Har), 7.55 (dd, J=7.6, 7.6 Hz, 1H, Har), 7.44 (d, J=7.7 Hz, 1H, Har), 7.41 (d, J=8.1 Hz, 2H, Har), 7.22 (d, J=8.0 Hz, 1H, Har), 7.18 (s, 1H, Har), 3.54 (s, 2H, CH$_2$), 2.50 (s, 3H, CH$_3$), 2.48 (bs, 8H, 4×CH$_2$), 2.31 (s, 3H, CH$_3$). $^{13}$C NMR (101 MHz, CDCl$_3$) δ 165.05 (C), 159.00 (C), 149.56 (C), 144.26 (C), 140.75 (C), 134.35 (CH), 132.25 (C), 131.81 (CH), 131.49 (q, J=30.4 Hz, C), 131.00 (C), 130.29 (CH), 130.07 (CH), 129.67 (2×CH), 128.30 (CH), 127.80 (2×CH), 126.77 (CH), 126.24 (q, J=5.6 Hz, CH), 123.98 (d, J=273.4 Hz, C), 123.23 (C), 122.00 (C), 108.32 (CH), 94.10 (C), 89.60 (C), 62.70 (CH$_2$), 55.28 (2×CH$_2$), 53.21 (2×CH$_2$), 46.13 (CH$_3$), 20.67 (CH$_3$). HRMS [M+H]$^+$ C$_{32}$H$_{30}$F$_3$N$_4$OS: Calcd. 575.2087 found 575.2069. Purity: 92.9%.

Example 8

N-(4-(3-((2-methoxyphenyl)ethynyl)-4-methylphenyl)thiazol-2-yl)-4-((4-methylpiperazin-1-yl)methyl)benzamide

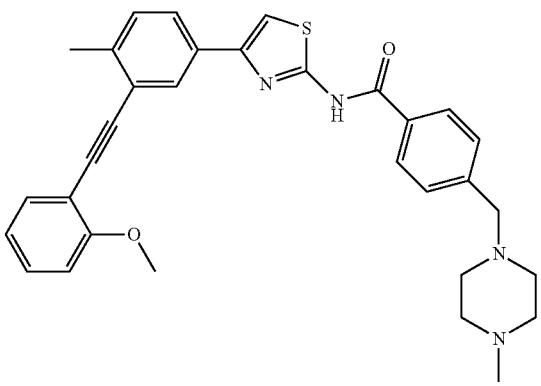 [SMILES: COc1ccccc1C#Cc1cc(-c2csc(NC(=O)c3ccc(CN4CCN(C)CC4)cc3)n2)ccc1C]

According the general procedure D using N-(4-(3-bromo-4-methylphenyl)thiazol-2-yl)-4-((4-methylpiperazin-1-yl)methyl)benzamide (30 mg, 0.062 mmol). Purification by silica gel flash chromatography (DCM/MeOH 85:15) afforded the product (17.1 mg, 52%) as a yellow viscous oil. $^1$H NMR (400 MHz, CDCl$_3$) δ 7.93 (d, J=1.6 Hz, 1H, Har), 7.87 (d, J=8.1 Hz, 2H, Har), 7.63 (dd, J=7.9, 1.7 Hz, 1H, Har), 7.51 (dd, J=7.5, 1.4 Hz, 1H, Har), 7.42 (d, J=8.1 Hz, 2H, Har), 7.35-7.29 (m, 1H, Har), 7.22 (d, J=8.0 Hz, 1H, Har), 7.17 (s, 1H, Har), 6.96 (dd, J=7.6, 7.6 Hz, 1H, Har), 6.92 (d, J=8.4 Hz, 1H, Har), 3.93 (s, 3H, CH$_3$), 3.56 (s, 2H, CH$_2$), 2.53 (s, 3H, CH$_3$), 2.50 (bs, 8H, 4×CH$_2$), 2.32 (s, 3H, CH$_3$). $^{13}$C NMR (101 MHz, CDCl$_3$) δ 165.0 (C), 160.3 (C), 158.8 (C), 149.8 (C), 144.2 (C), 140.4 (C), 133.7 (CH), 132.1 (C), 131.0 (C), 130.1 (CH), 130.1 (CH), 129.7 (2×CH), 129.6 (CH), 127.8 (2×CH), 126.1 (CH), 120.8 (CH), 113.0 (C), 111.1 (CH), 108.1 (CH), 92.6 (C), 90.3 (C), 62.7 (CH$_2$), 56.2 (CH$_3$), 55.2 (2×CH$_2$), 53.1 (2×CH$_2$), 46.1 (CH$_3$), 20.8 (CH$_3$). HRMS [M+H]$^+$ C$_{33}$H$_{33}$N$_4$OS: Calcd. 537.2319 found 537.2303. Purity: 96.9%.

Example 9

N-(4-(3-((4-fluorophenyl)ethynyl)-4-methylphenyl)thiazol-2-yl)-4-((4-methylpiperazin-1-yl)methyl)benzamide

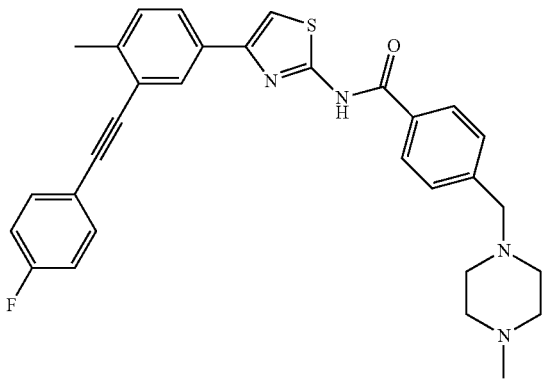 [SMILES: Cc1ccc(-c2csc(NC(=O)c3ccc(CN4CCN(C)CC4)cc3)n2)cc1C#Cc1ccc(F)cc1]

According the general procedure D using N-(4-(3-bromo-4-methylphenyl)thiazol-2-yl)-4-((4-methylpiperazin-1-yl)methyl)benzamide (30 mg, 0.062 mmol). Purification by silica gel flash chromatography (DCM/MeOH 85:15) afforded the product (15.4 mg, 52%) as a yellow viscous oil. $^1$H NMR (300 MHz, CDCl$_3$) δ 7.91 (d, J=1.7 Hz, 1H, Har), 7.87 (d, J=8.2 Hz, 2H, Har), 7.64 (dd, J=7.9, 1.8 Hz, 1H, Har), 7.57-7.50 (m, 2H, Har), 7.43 (d, J=8.2 Hz, 2H, Har), 7.23 (d, J=8.1 Hz, 1H, Har), 7.17 (s, 1H, Har), 7.09-7.04 (m, 2H, Har), 3.56 (s, 2H, CH$_2$), 2.54 (bs, 8H, 4×CH$_2$), 2.50 (s, 3H, CH$_3$), 2.32 (s, 3H, CH$_3$). $^{13}$C NMR (101 MHz, CDCl$_3$) δ 164.92 (C), 162.88 (d, J=249.4 Hz, C), 158.88 (C), 149.65 (C), 144.26 (C), 140.20 (C), 133.74 (d, J=8.3 Hz, 2×CH), 132.26 (C), 130.99 (C), 130.01 (d, J=44.7 Hz, 2×CH), 129.73 (2×CH), 127.80 (2×CH), 126.27 (CH), 123.63 (C), 119.84 (C), 116.04 (d, J=22.1 Hz, 2×CH), 108.24 (CH), 92.78 (C), 88.17 (C), 62.70 (CH$_2$), 55.24 (2×CH$_2$), 53.15 (2×CH$_2$), 46.07 (CH$_3$), 20.83 (CH$_3$). HRMS [M+H]$^+$ C$_{31}$H$_{30}$FN$_4$OS: Calcd. 525.2119 found 525.2116. Purity: 96.1%.

Example 10

N-(4-(3-methyl-4-(p-tolylethynyl)phenyl)thiazol-2-yl)-4-((4-methylpiperazin-1-yl)methyl)benzamide

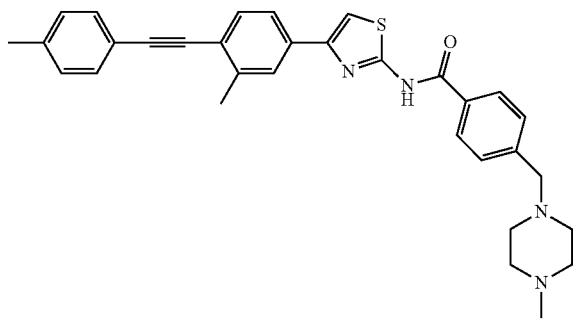 [SMILES: Cc1ccc(C#Cc2ccc(-c3csc(NC(=O)c4ccc(CN5CCN(C)CC5)cc4)n3)cc2C)cc1]

According the general procedure D using N-(4-(3-methyl-4-bromophenyl)thiazol-2-yl)-4-((4-methylpiperazin-1-yl)methyl)benzamide (23 mg, 0.047 mmol). Purification by silica gel flash chromatography (DCM/MeOH 85:15) afforded the product (14.2 mg, 58%) as a yellow viscous oil. $^1$H NMR (400 MHz, CDCl$_3$) δ 10.37 (bs, 1H, Har), 7.83 (d, J=8.2 Hz, 2H, Har), 7.64 (bs, 1H, Har), 7.56 (dd, J=8.0, 1.4 Hz, 1H, Har), 7.48-7.37 (m, 5H, Har), 7.21 (s, 1H, Har), 7.16 (d, J=8.1 Hz, 2H, Har), 3.53 (s, 2H, CH$_2$), 2.51 (s, 3H, CH$_3$), 2.47 (bs, 8H, 4×CH$_2$), 2.37 (s, 3H, CH$_3$), 2.29 (s, 3H, CH$_3$). $^{13}$C NMR (101 MHz, CDCl$_3$) δ 165.0 (C), 158.9 (C), 150.0 (C), 144.4 (C), 140.8 (C), 138.7 (C), 134.0 (C), 132.4 (CH), 131.7 (2×CH), 130.9 (C), 129.7 (2×CH), 129.5 (2×CH), 127.7 (2×CH), 127.2 (CH), 123.5 (CH), 123.2 (C), 120.7 (C), 108.9 (CH), 94.8 (C), 88.0 (C), 62.7 (CH$_2$), 55.4 (2×CH$_2$), 53.4 (2×CH$_2$), 46.3 (CH$_3$), 21.9 (CH$_3$), 21.2 (CH$_3$). HRMS [M+H]$^+$ C$_{32}$H$_{33}$N$_4$OS: Calcd. 521.2370 found 521.2373. Purity: 97.8%.

Example 11

N-(4-(3-methyl-4-((2-(trifluoromethyl)phenyl)ethynyl)phenyl)thiazol-2-yl)-4-((4-methylpiperazin-1-yl)methyl)benzamide

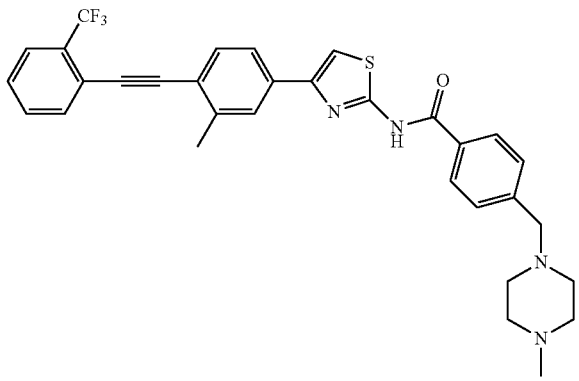 [SMILES: Cc1cc(-c2csc(NC(=O)c3ccc(CN4CCN(C)CC4)cc3)n2)ccc1C#Cc1ccccc1C(F)(F)F]

According general procedure D using N-(4-(3-methyl-4-bromophenyl)thiazol-2-yl)-4-((4-methylpiperazin-1-yl)methyl)benzamide (23 mg, 0.047 mmol). Purification by silica gel flash chromatography (DCM/MeOH 85:15) afforded the product (16.1 mg, 60%) as a yellow viscous oil. $^1$H NMR (400 MHz, CDCl$_3$) δ 10.36 (bs, 1H, NH), 7.83 (d, J=8.1 Hz, 2H, Har), 7.73-7.64 (m, 1H, Har), 7.60-7.37 (m, 6H, Har), 7.23 (s, 1H, Har), 3.53 (s, 2H, CH$_2$), 2.52 (s, 3H, CH$_3$), 2.47 (bs, 8H, 4×CH$_2$), 2.29 (s, 3H, CH$_3$). $^{13}$C NMR (101 MHz, CDCl$_3$) δ 165.1 (C), 158.9 (C), 149.8 (C), 144.4 (C), 141.3 (C), 134.8 (C), 134.2 (CH), 132.9 (CH), 131.8 (CH), 131.4 (q, J=30.3 Hz, C), 130.8 (C), 129.7 (2×CH), 128.2 (CH), 127.7 (2×CH), 127.4 (CH), 126.2 (q, J=5.3 Hz, CH), 124.0 (d, J=273.2 Hz, C), 123.5 (CH), 122.4 (C), 122.0 (q, J=2.0 Hz, C), 109.3 (CH), 94.3 (C), 90.2 (C), 62.7 (CH$_2$), 55.4 (2×CH$_2$), 53.5 (2×CH$_2$), 46.3 (CH$_3$), 21.0 (CH$_3$). HRMS (ESI) [M+H]$^+$ C$_{32}$H$_{30}$F$_3$N$_4$OS: Calcd. 575.2087 found 575.2085. Purity: 97.8%.

Example 12

4-((4-methylpiperazin-1-yl)methyl)-N-(4-(3-((2-(trifluoromethyl)phenyl)ethynyl)phenyl)thiazol-2-yl)benzamide

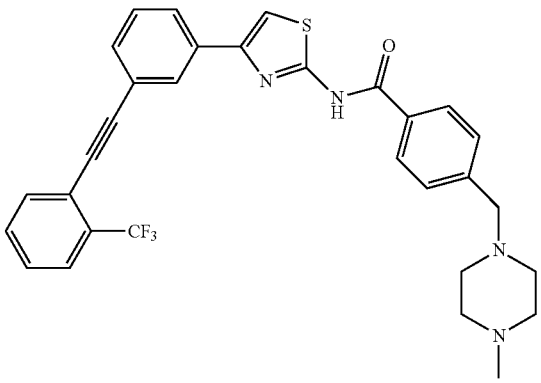 [SMILES: CN1CCN(Cc2ccc(C(=O)Nc3nc(-c4cccc(C#Cc5ccccc5C(F)(F)F)c4)cs3)cc2)CC1]

According general procedure D using N-(4-(3-bromophenyl)thiazol-2-yl)-4-((4-methylpiperazin-1-yl)methyl)benzamide (28 mg, 0.059 mmol). Purification by silica gel flash chromatography (DCM/MeOH 85:15) afforded the product (4.8 mg, 15%) as a yellow viscous oil. $^1$H NMR (400 MHz, CDCl$_3$) δ 9.88 (bs, 1H, NH), 8.01 (d, J=1.5,1.5 Hz, 1H, Har), 7.91 (d, J=8.2 Hz, 2H, Har), 7.81 (ddd, J=7.8, 2.7, 1.3 Hz, 1H, Har), 7.70 (d, J=8.1 Hz, 1H, Har), 7.69 (d, J=7.3 Hz, 1H, Har), 7.57-7.45 (m, 5H, Har), 7.45-7.38 (m, 2H, Har), 7.25 (s, 1H, Har), 3.59 (s, 2H, CH$_2$), 2.55 b(s, 8H, 4×CH$_2$), 2.37 (s, 3H, CH$_3$). $^{13}$C NMR (101 MHz, CDCl$_3$) δ 164.7 (C), 158.6 (C), 149.5 (C), 144.3 (C), 134.9 (C), 134.1 (CH), 131.9 (q, J=30.4 Hz, C), 131.8 (CH), 131.6 (CH), 131.0 (C), 129.8 (2×CH), 129.6 (CH), 129.2 (CH), 128.4 (CH), 127.8 (2×CH), 126.8 (CH), 126.3 (q, J=5.2 Hz, CH), 124.0 (d, J=273.3 Hz, C), 123.6 (C), 121.8 (d, J=2.1 Hz, C), 109.1 (CH), 95.0 (C), 85.9 (C), 62.6 (CH$_2$), 55.2 (2×CH$_2$), 53.0 (2×CH$_2$), 46.0 (CH$_3$). HRMS (ESI) [M+H]$^+$ C$_{31}$H$_{28}$F$_3$N$_4$OS: Calcd. 561.1903 found 561.1930. Purity: 97.0%.

Example 13

N-(4-(3,4-bis((2-(trifluoromethyl)phenyl)ethynyl)phenyl)thiazol-2-yl)-4-((4-methylpiperazin-1-yl)methyl)benzamide

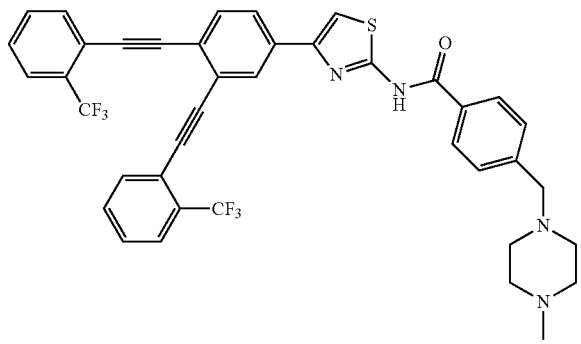 [SMILES: CN1CCN(Cc2ccc(C(=O)Nc3nc(-c4ccc(C#Cc5ccccc5C(F)(F)F)c(C#Cc5ccccc5C(F)(F)F)c4)cs3)cc2)CC1]

According general procedure E using N-(4-(4-bromo-3-chlorophenyl)thiazol-2-yl)-4-((4-methylpiperazin-1-yl)methyl)benzamide (30 mg, 0.059 mmol). Purification by silica gel flash chromatography (DCM/MeOH 85:15) afforded the product (17.4 mg, 41%) as a yellow viscous oil. $^1$H NMR (400 MHz, CDCl$_3$) δ 7.99 (d, J=1.6 Hz, 1H, Har), 7.85 (d, J=8.2 Hz, 2H, Har), 7.78-7.67 (m, 5H, Har), 7.58-7.48 (m, 3H, Har), 7.47-7.38 (m, 4H, Har), 7.30 (s, 1H, Har), 3.54 (s, 2H, CH$_2$), 2.48 (s, 8H, 4×CH$_2$), 2.30 (s, 3H, CH$_3$). $^{13}$C NMR (101 MHz, CDCl3) δ 165.2 (C), 159.1 (C), 148.8 (C), 144.5 (C), 134.7 (C), 134.5 (CH), 134.3 (CH), 133.3 (CH), 131.8 (q, J=30.7 Hz, 2×C), 131.8 (d, J=1.5 Hz, 2×CH), 130.9 (C), 130.2 (CH), 129.7 (2×CH), 128.5 (d, J=7.0 Hz, 2×CH), 127.8 (2×CH), 126.3 (CH), 126.2 (q, J=5.1 Hz, 2×CH), 125.7 (C), 124.6 (C), 123.9 (d, J=273.4 Hz, 2×C), 121.8-121.6 (m, 2×C), 110.0 (CH), 93.7 (d, J=0.7 Hz, C), 93.5 (C), 90.4 (C), 89.7 (C), 62.7 (CH$_2$), 55.3 (2×CH$_2$), 53.3 (2×CH$_2$), 46.2 (CH$_3$). HRMS [M+H]$^+$ C$_{40}$H$_{31}$F$_6$N$_4$OS: Calcd. 729.2117 found 729.2094. Purity: 89.0%.

Example 14

N-(4-(4-methyl-3-((triisopropylsilyl)ethynyl)phenyl)thiazol-2-yl)-4-((4-methylpiperazin-1-yl)methyl)benzamide

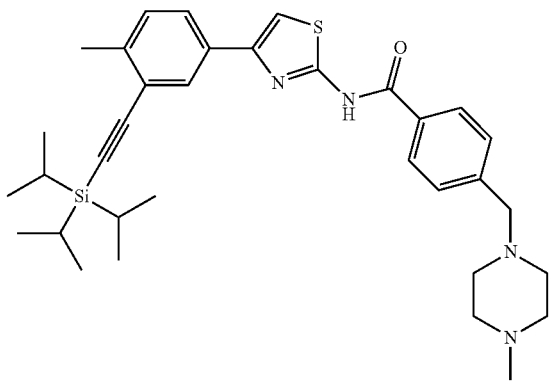 [SMILES: Cc1ccc(-c2csc(NC(=O)c3ccc(CN4CCN(C)CC4)cc3)n2)cc1C#C[Si](C(C)C)(C(C)C)C(C)C]

According general procedure G using N-(4-(3-bromo-4-methylphenyl)thiazol-2-yl)-4-((4-methylpiperazin-1-yl)methyl)benzamide (30 mg, 0.062 mmol). Purification by silica gel flash chromatography (DCM/MeOH 9:1) afforded the product (27.3 mg, 75%) as a yellow viscous oil. $^1$H NMR (400 MHz, CDCl$_3$) δ 7.82 (s, 1H, Har), 7.80 (d, J=8.3 Hz, 2H, Har), 7.57 (dd, J=7.9, 1.9 Hz, 1H, Har), 7.36 (d, J=8.2 Hz, 2H, Har), 7.17-7.12 (m, 2H, Har), 3.52 (s, 2H, CH$_2$), 2.47 (bs, 8H, 4×CH$_2$), 2.43 (s, 3H, CH$_3$), 2.32 (s, 3H, CH$_3$), 1.14 (s, 21H, 3×CH(CH$_3$)$_2$). $^{13}$C NMR (101 MHz, CDCl$_3$) δ 165.1 (C), 158.9 (C), 149.6 (C), 144.1 (C), 140.6 (C), 132.1 (C), 131.1 (C), 130.1 (CH), 130.0 (CH), 129.6 (2×CH), 127.8 (2×CH), 126.1 (CH), 124.0 (C), 108.2 (CH), 105.8 (C), 95.12 (C), 62.7 (CH$_2$), 55.3 (2×CH$_2$), 53.2 (2×CH$_2$), 46.1 (CH$_3$), 21.0 (CH$_3$), 19.0 (6×CH$_3$), 11.6 (3×CH). HRMS [M+H]$^+$ C$_{34}$H$_{47}$N$_4$OSSi: Calcd. 587.3234 found 587.3207. Purity: 98.8%.

Example 15

N-(4-(3-methyl-4-((triisopropylsilyl)ethynyl)phenyl)thiazol-2-yl)-4-((4-methylpiperazin-1-yl)methyl)benzamide

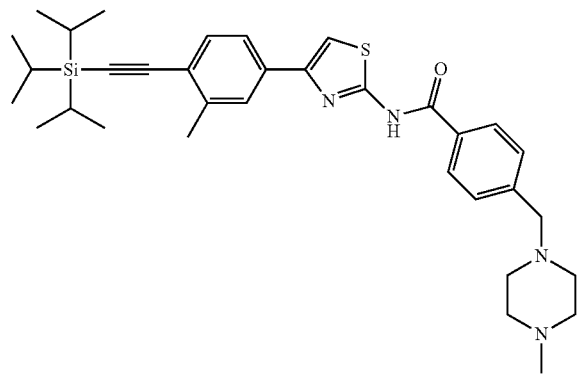 [SMILES: Cc1cc(-c2csc(NC(=O)c3ccc(CN4CCN(C)CC4)cc3)n2)ccc1C#C[Si](C(C)C)(C(C)C)C(C)C]

According general procedure G using N-(4-(4-bromo-3-methylphenyl)thiazol-2-yl)-4-((4-methylpiperazin-1-yl)

methyl)benzamide (26 mg, 0.053 mmol). Purification by silica gel flash chromatography (DCM/MeOH 9:1) afforded the product (10.9 mg, 35%) as a yellow viscous oil. $^1$H NMR (400 MHz, CDCl$_3$) δ 7.86 (d, J=8.3 Hz, 2H, Har), 7.63 (s, 1H, Har), 7.53 (dd, J=8.0, 1.4 Hz, 1H, Har), 7.46-7.39 (m, 3H, Har), 7.19 (s, 1H, Har), 3.56 (s, 2H, CH$_2$), 2.54 (bs, 8H, 4×CH$_2$), 2.47 (s, 3H, CH$_3$), 2.37 (s, 3H, CH$_3$), 1.15 (s, 21H, 3×CH(CH$_3$)$_2$). $^{13}$C NMR (101 MHz, CDCl$_3$) δ 164.8 (C), 158.7 (C), 150.0 (C), 144.2 (C), 141.3 (C), 134.2 (C), 133.0 (CH), 131.0 (C), 129.7 (2×CH), 127.7 (2×CH), 127.2 (CH), 123.4 (CH), 123.3 (C), 109.0 (CH), 106.0 (C), 95.9 (C), 62.6 (CH$_2$), 55.2 (2×CH$_2$), 52.9 (2×CH$_2$), 46.0 (CH$_3$), 21.4 (CH$_3$), 19.0 (6×CH$_3$), 11.7 (3×CH). HRMS [M+H]$^+$ C$_{34}$H$_{47}$N$_4$OSSi. Calcd. 587.3234 found 587.3211. Purity: 98.4%.

Example 16

N-(4-(3,4-bis((triisopropylsilyl)ethynyl)phenyl)thiazol-2-yl)-4((4-methylpiperazin-1-yl)methyl)benzamide

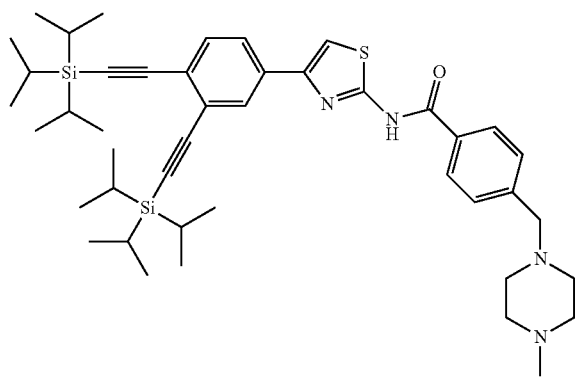 [SMILES: CC(C)[Si](C#Cc1ccc(-c2csc(NC(=O)c3ccc(CN4CCN(C)CC4)cc3)n2)cc1C#C[Si](C(C)C)(C(C)C)C(C)C)(C(C)C)C(C)C]

According general procedure H using N-(4-(4-bromo-3-chlorophenyl)thiazol-2-yl)-4-((4-methylpiperazin-1-yl)methyl)benzamide (26 mg, 0.052 mmol). Purification by silica gel flash chromatography (DCM/MeOH 9:1) afforded the product (29.3 mg, 75%) as a yellow viscous oil. $^1$H NMR (400 MHz, CDCl$_3$) δ 7.84 (d, J=1.6 Hz, 1H, Har), 7.81 (d, J=8.3 Hz, 2H, Har), 7.60 (dd, J=8.1, 1.8 Hz, 1H, Har), 7.42 (d, J=8.2 Hz, 1H, Har), 7.37 (d, J=8.2 Hz, 2H, Har), 7.23 (s, 1H, Har), 3.52 (s, 2H, CH$_2$), 2.46 (bs, 8H, 4×CH$_2$), 2.30 (s, 3H, CH$_3$), 1.14 (s, 42H, 6×CH(CH$_3$)$_2$). $^{13}$C NMR (101 MHz, CDCl$_3$) δ 165.2 (C), 159.2 (C), 149.0 (C), 144.4 (C), 134.2 (CH), 134.0 (C), 131.0 (CH), 130.9 (C), 129.7 (2×CH), 127.8 (2×CH), 126.1 (C), 125.6 (CH), 125.2 (C), 109.6 (CH), 105.8 (C), 105.5 (C), 96.2 (C), 95.4 (C), 62.8 (CH$_2$), 55.4 (2×CH$_2$), 53.4 (2×CH$_2$), 46.3 (CH$_3$), 19.1 (6×CH$_3$), 19.1 (6×CH$_3$), 11.7 (3×CH), 11.7 (3×CH). HRMS [M+H]$^+$ C$_{44}$H$_{65}$N$_4$OSSi$_2$. Calcd. 753.4412 found 753.4398. Purity: 87.3%.

Example 17

4-((4-methylpiperazin-1-yl)methyl)-N-(4-(3-((triethylsilyl)ethynyl)phenyl)thiazol-2-yl)benzamide

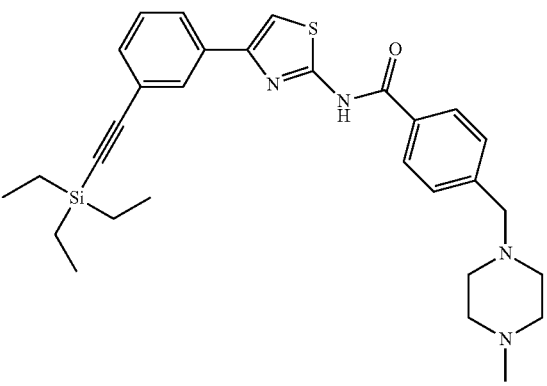 [SMILES: CC[Si](C#Cc1cccc(-c2csc(NC(=O)c3ccc(CN4CCN(C)CC4)cc3)n2)c1)(CC)CC]

According general procedure F using N-(4-(3-bromophenyl)thiazol-2-yl)-4-((4-methylpiperazin-1-yl)methyl)benzamide (30 mg, 0.063 mmol). Purification by silica gel flash chromatography (DCM/MeOH 9:1) afforded the product (9.6 mg, 29%) as a yellow viscous oil. $^1$H NMR (400 MHz, CDCl$_3$) δ 7.90-7.86 (m, 3H, Har), 7.72 (d, J=7.7 Hz, 1H, Har), 7.44 (d, J=8.1 Hz, 2H, Har), 7.39 (d, J=7.7 Hz, 1H, Har), 7.30 (dd, J=7.7, 7.7 Hz, 1H, Har), 7.20 (s, 1H, Har), 3.57 (s, 2H, CH$_2$), 2.53 (bs, 8H, 4×CH$_2$), 2.35 (s, 3H, CH$_3$), 1.06 (t, J=7.9 Hz, 9H, 3×CH$_2$CH$_3$), 0.69 (q, J=7.9 Hz, 6H, 3×CH$_2$CH$_3$). $^{13}$C NMR (101 MHz, CDCl$_3$) δ 164.9 (C), 158.8 (C), 149.5 (C), 144.3 (C), 134.6 (C), 131.9 (CH), 130.9 (C), 129.9 (CH), 129.8 (2×CH), 128.9 (CH), 127.8 (2×CH), 126.3 (CH), 124.1 (C), 109.0 (CH), 106.4 (C), 92.3 (C), 62.6 (CH$_2$), 55.2 (2×CH$_2$), 53.0 (2×CH$_2$), 46.1 (CH$_3$), 7.9 (3×CH$_2$CH$_3$), 4.8 (3×CH$_2$CH$_3$). HRMS [M+H]$^+$ C$_{30}$H$_{39}$N$_4$OSSi: Calcd. 531.2608 found 531.2600. Purity: 99.2%.

Example 18

4-((4-methylpiperazin-1-yl)methyl)-N-(4-(3-((trimethylsilyl)ethynyl)phenyl)thiazol-2-yl)benzamide

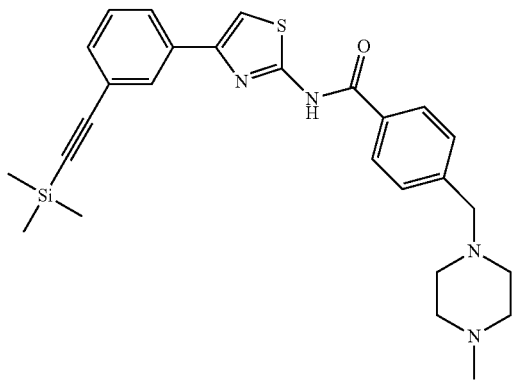 [SMILES: CN1CCN(Cc2ccc(C(=O)Nc3nc(-c4cccc(C#C[Si](C)(C)C)c4)cs3)cc2)CC1]

According general procedure G using N-(4-(3-bromophenyl)thiazol-2-yl)-4-((4-methylpiperazin-1-yl)methyl)benzamide (51 mg, 0.109 mmol). Purification by silica gel flash chromatography (DCM/MeOH 9:1) afforded the product (8.6 mg, 16%) as a yellow viscous oil. $^1$H NMR (400 MHz, CDCl$_3$) δ 7.89 (dd, J=1.5, 1.5 Hz, 1H, Har), 7.86 (d, J=8.3 Hz, 2H, Har), 7.73 (ddd, J=7.8, 1.5, 1.5 Hz, 1H, Har), 7.43 (d, J=8.2 Hz, 2H, Har), 7.38 (ddd, J=7.6, 1.3, 1.3 Hz, 1H, Har), 7.30 (dd, J=7.7, 7.7 Hz, 1H, Har), 7.21 (s, 1H, Har), 3.57 (s, 2H, CH$_2$), 2.55 (bs, 8H, 4×CH$_2$), 2.37 (s, 3H, CH$_3$), 0.26 (s, 9H, 3×CH$_3$Si). $^{13}$C NMR (101 MHz, CDCl$_3$) δ 164.8 (C), 158.7 (C), 149.5 (C), 144.2 (C), 134.6 (C), 131.7 (CH), 131.0 (C), 129.9 (CH), 129.8 (2×CH), 129.0 (CH), 127.8 (2×CH), 126.4 (CH), 123.9 (C), 109.0 (CH), 105.1 (C), 94.8 (C), 62.6 (CH$_2$), 55.2 (2×CH$_2$), 52.9 (2×CH$_2$), 46.0 (CH$_3$), 0.3 (3×CH$_3$Si). HRMS [M+H]$^+$ C$_{27}$H$_{33}$N$_4$OSSi: Calcd. 489.2132 found 489.2110. Purity: 97.7%.

Example 19

N-(4-(3-(cyclohex-1-en-1-ylethynyl)phenyl)thiazol-2-yl)-4-((4-methylpiperazin-1-yl)methyl)benzamide

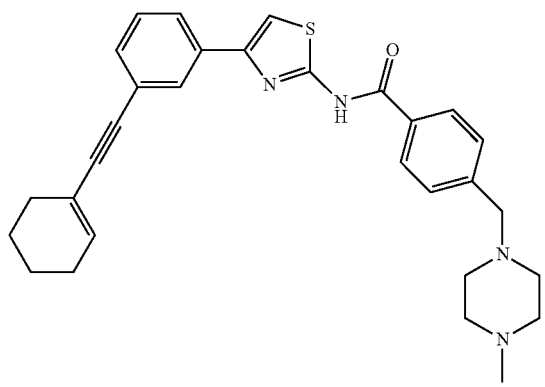 [SMILES: CN1CCN(Cc2ccc(C(=O)Nc3nc(-c4cccc(C#CC5=CCCCC5)c4)cs3)cc2)CC1]

According general procedure G using N-(4-(3-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (12.4 mg, 39%) as a yellow viscous oil. $^1$H NMR (400 MHz, CDCl$_3$) δ 7.86-7.81 (m, 3H, Har), 7.67 (ddd, J=7.4, 1.5, 1.5 Hz, 1H, Har), 7.40 (d, J=8.2 Hz, 2H, Har), 7.32 (dd, J=7.6, 1.4, 1.4 Hz, 1H, Har), 7.28 (d, J=7.6 Hz, 1H, Har), 7.19 (s, 1H, Har), 6.25-6.21 (m, 1H, Har), 3.54 (s, 2H, CH$_2$), 2.51 (bs, 8H, 4×CH$_2$), 2.34 (s, 3H, CH$_3$), 2.28-2.11 (m, 4H, H$_{cycl}$), 1.75-1.57 (m, 4H, H$_{cycl}$). $^{13}$C NMR (101 MHz, CDCl$_3$) δ 165.0 (C), 158.9 (C), 149.7 (C), 144.2 (C), 135.8 (CH), 134.6 (C), 131.2 (CH), 131.0 (C), 129.7 (2×CH), 129.4 (CH), 129.0 (CH), 127.8 (2×CH), 125.6 (CH), 124.5 (C), 121.0 (C), 108.8 (CH), 91.9 (C), 86.9 (C), 62.7 (CH$_2$), 55.3 (2×CH$_2$), 53.1 (2×CH$_2$), 46.1 (CH$_3$), 29.6 (CH$_{cycl}$), 26.1 (CH$_{cycl}$), 22.7 (CH$_{cycl}$), 21.8 (CH$_{cycl}$). HRMS [M+H]$^+$ C$_{30}$H$_{33}$N$_4$OS: Calcd. 497.2370 found 497.2355. Purity: 95.2%.

Example 20

N-(4-(3-(hex-1-yn-1-yl)phenyl)thiazol-2-yl)-4-((4-methylpiperazin-1-yl)methyl)benzamide

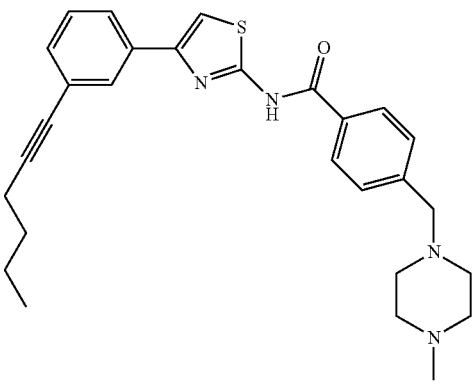 [SMILES: CCCCC#Cc1cccc(-c2csc(NC(=O)c3ccc(CN4CCN(C)CC4)cc3)n2)c1]

According general procedure G using N-(4-(3-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (16.5 mg, 55%) as a yellow viscous oil. $^1$H NMR (400 MHz, CDCl$_3$) δ 7.8 (d, J=8.3 Hz, 2H, Har), 7.75 (dd, J=1.7, 1.7 Hz,1H, Har), 7.61 (ddd, J=7.1, 1.7, 1.7 Hz, 1H, Har), 7.36 (d, J=8.2 Hz, 2H, Har), 7.26-7.20 (m, 2H, Har), 7.12 (s, 1H, Har), 3.51 (s, 2H, CH$_2$), 2.49 (bs, 8H, 4×CH$_2$), 2.36 (t, J=7.0 Hz, 2H, CH$_2$), 2.32 (s, 3H, CH$_3$), 1.57-1.48 (m, 2H, CH$_2$), 1.47-1.39 (m, 2H, CH$_2$), 0.89 (t, J=7.3 Hz, 3H, CH$_3$). $^{13}$C NMR (101 MHz, CDCl$_3$) δ 164.9 (C), 158.7 (C), 149.8 (C), 144.1 (C), 134.6 (C), 131.4 (CH), 131.0 (C), 129.7 (2×CH), 129.5 (CH), 128.9 (CH), 127.8 (2×CH), 125.5 (CH), 124.9 (C), 108.8 (CH), 91.1 (C), 80.7 (C), 62.6 (CH$_2$), 55.2 (2×CH$_2$), 52.8 (2×CH$_2$), 45.9 (CH$_3$), 31.2 (CH$_2$), 22.4 (CH$_2$), 19.5 (CH$_2$), 14.0 (CH$_3$). HRMS [M+H]$^+$ C$_{28}$H$_{33}$N$_4$OS: Calcd. 473.2370 found 473.2378. Purity: 85.1%.

Example 21

N-(4-(3-(3-((tert-butyldiphenylsilyl)oxy)prop-1-yn-1-yl)phenyl)thiazol-2-yl)-4-((4-methylpiperazin-1-yl)methyl)benzamide

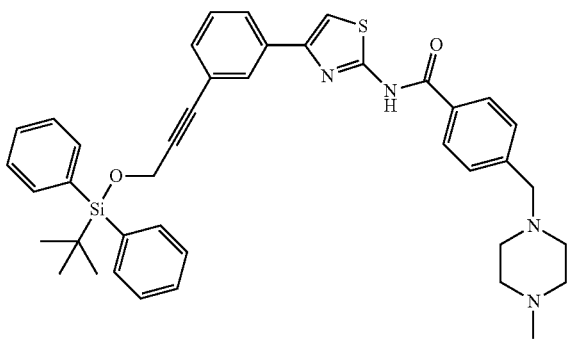 [SMILES: CN1CCN(Cc2ccc(C(=O)Nc3nc(-c4cccc(C#CCO[Si](c5ccccc5)(c5ccccc5)C(C)(C)C)c4)cs3)cc2)CC1]

According general procedure G using N-(4-(3-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (21.5 mg, 50%) as a yellow viscous oil. $^1$H NMR (400 MHz, CDCl$_3$) δ 7.85 (d, J=8.2 Hz, 2H, Har), 7.80-7.74 (m, 5H, Har), 7.72 (dd, J=7.2, 1.6 Hz, 1H, Har), 7.46-7.36 (m, 8H, Har), 7.31-7.26 (m, 2H, Har), 7.18 (s, 1H, Har), 4.56 (s, 2H, CH$_2$), 3.55 (s, 2H, CH$_2$), 2.52 (bs, 8H, 4×CH$_2$), 2.35 (s, 3H, CH$_3$), 1.09 (s, 9H, (CH$_3$)$_3$). $^{13}$C NMR (101 MHz, CDCl$_3$) δ 165.0 (C), 158.8 (C), 149.6 (C), 144.2 (C), 136.0 (4×CH), 134.6 (C), 133.5 (C), 131.4 (CH), 131.0 (C), 130.1 (2×CH), 129.7 (2×CH), 129.5 (CH), 128.9 (CH), 128.1 (4×CH), 127.8 (2×CH), 126.1 (CH), 123.7 (C), 108.9 (CH), 88.2 (C), 85.2 (C), 62.6 (CH$_2$), 55.2 (2×CH$_2$), 53.5 (CH$_2$), 53.0 (2×CH$_2$), 46.0 (CH$_3$), 27.1 (3×CH3), 19.6 (C). HRMS [M+H]$^+$ C$_{41}$H$_{45}$N$_4$O$_2$SSi: Calcd. 685.3027 found 685.3044. Purity: 97.6%.

Example 22

4-((4-methylpiperazin-1-yl)methyl)-N-(4-(3-(3-((tri-isopropylsilyl)oxy)prop-1-yn-1-yl)phenyl)thiazol-2-yl)benzamide

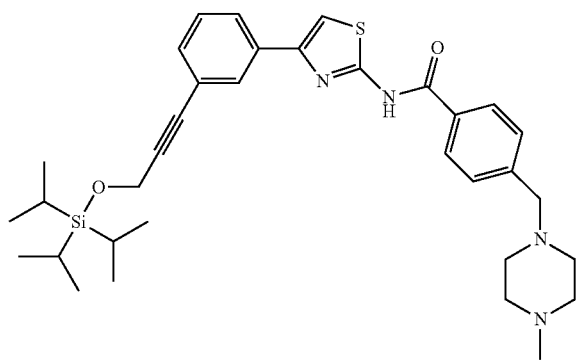 [SMILES: CC(C)[Si](OCC#Cc1cccc(-c2csc(NC(=O)c3ccc(CN4CCN(C)CC4)cc3)n2)c1)(C(C)C)C(C)C]

According general procedure G using N-(4-(3-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (15.8 mg, 42%) as a yellow viscous oil. $^1$H NMR (400 MHz, CDCl$_3$) δ 7.86-7.83 (m, 3H, Har), 7.72 (ddd, J=7.4, 1.6, 1.6 Hz, 1H, Har), 7.42 (d, J=8.3 Hz, 2H, Har), 7.34 (ddd, J=7.6, 1.5, 1.5 Hz, 1H, Har), 7.31 (d, J=7.5 Hz, 1H, Har), 7.19 (s, 1H, Har), 4.62 (s, 2H, CH$_2$), 3.56 (s, 2H, CH$_2$), 2.53 (bs, 8H, 4×CH$_2$), 2.35 (s, 3H, CH$_3$), 1.12 (d, J=5.8 Hz, 21H, ((CH$_3$)$_2$CH)$_3$). $^{13}$C NMR (101 MHz, CDCl$_3$) δ 164.9 (C), 158.8 (C), 149.6 (C), 144.2 (C), 134.7 (C), 131.4 (CH), 131.0 (C), 129.7 (2×CH), 129.5 (CH), 129.0 (CH), 127.7 (2×CH), 126.2 (CH), 123.8 (C), 108.9 (CH), 88.7 (C), 84.6 (C), 62.6 (CH$_2$), 55.2 (2×CH$_2$), 53.0 (CH$_2$), 52.8 (2×CH$_2$), 46.0 (CH$_3$), 18.3 (6×CH$_3$), 12.4 (3×CH). HRMS [M+H]$^+$ C$_{34}$H$_{47}$N$_4$O$_2$SSi: Calcd. 603.3184 found 603.3192. Purity: 95.6%.

Example 23

N-(4-(3-(3-((tert-butyldimethylsilyl)oxy)prop-1-yn-1-yl)phenyl)thiazol-2-yl)-4-((4-methylpiperazin-1-yl)methyl)benzamide

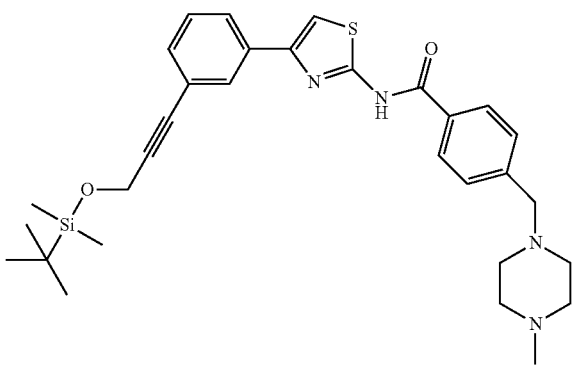 [SMILES: CN1CCN(Cc2ccc(C(=O)Nc3nc(-c4cccc(C#CCO[Si](C)(C)C(C)(C)C)c4)cs3)cc2)CC1]

According general procedure G using N-(4-(3-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (14.1 mg, 40%) as a yellow viscous oil. $^1$H NMR (400 MHz, CDCl$_3$) δ 7.87-7.84 (m, 3H, Har), 7.73 (ddd, J=7.4, 1.6, 1.6 Hz, 1H, Har), 7.43 (d, J=8.3 Hz, 2H, Har), 7.35 (ddd, J=7.6, 1.4, 1.4 Hz, 1H, Har), 7.32 (d, J=7.5 Hz, 1H, Ha), 7.19 (s, 1H, Har), 4.56 (s, 2H, CH$_2$), 3.57 (s, 2H, CH$_2$), 2.54 (bs, 8H, 4×CH$_2$), 2.36 (s, 3H, CH$_3$), 0.94 (s, 9H, (CH$_3$)$_3$), 0.18 (s, 6H, (CH$_3$)$_2$). $^{13}$C NMR (101 MHz, CDCl$_3$) δ 164.9 (C), 158.7 (C), 149.6 (C), 144.2 (C), 134.7 (C), 131.4 (CH), 131.0 (C), 129.8 (2×CH), 129.5 (CH), 129.0 (CH), 127.8 (2×CH), 126.2 (CH), 123.8 (C), 108.9 (CH), 88.5 (C), 84.9 (C), 62.6 (CH$_2$), 55.2 (2×CH$_2$), 52.9 (CH$_2$), 52.6 (2×CH$_2$), 46.0 (CH$_3$), 26.2 ((CH$_3$)$_3$CSi), 18.7 ((CH$_3$)$_3$CSi), −4.7 ((CH$_3$)$_2$Si). HRMS [M+H]$^+$ C$_{31}$H$_{41}$N$_4$O$_2$SSi: Calcd. 561.2714 found 561.2730. Purity: 97.5%.

Example 24

N-(4-(3-((tert-butyldimethylsilyl)ethynyl)phenyl)thiazol-2-yl)-4-((4-methylpiperazin-1-yl)methyl)benzamide

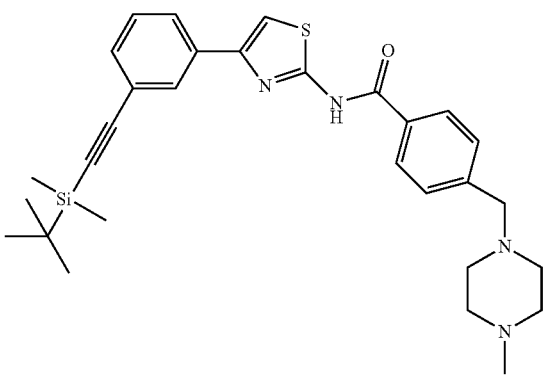 [SMILES: CN1CCN(Cc2ccc(C(=O)Nc3nc(-c4cccc(C#C[Si](C)(C)C(C)(C)C)c4)cs3)cc2)CC1]

According general procedure G using N-(4-(3-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (19.5 mg, 58%) as a yellow viscous oil. $^1$H NMR (400 MHz, CDCl$_3$) δ 7.86 (dd, J=1.5, 1.5 Hz, 1H, Har), 7.82 (d, J=8.2 Hz, 2H, Har), 7.70 (ddd, J=7.8, 1.5, 1.5 Hz, 1H, Har), 7.39 (d, J=8.2 Hz, 2H, Har), 7.36 (ddd, J=7.8, 1.4, 1.4 Hz, 1H, Har), 7.28 (d, J=7.8 Hz, 1H, Har), 7.21 (s, 1H, Har), 3.54 (s, 2H, CH$_2$), 2.50 (bs, 8H, 4×CH$_2$), 2.33 (s, 3H, CH$_3$), 1.00 (s, 9H, (CH$_3$)$_3$CSi), 0.19 (s, 6H, (CH$_3$)$_2$Si). $^{13}$C NMR (101 MHz, CDCl$_3$) δ 165.0 (C), 158.9 (C), 149.5 (C), 144.3 (C), 134.6 (C), 131.7 (CH), 131.0 (C), 129.9 (CH), 129.7 (2×CH), 128.9 (CH), 127.7 (2×CH), 126.3 (CH), 124.0 (C), 109.0 (CH), 105.8 (C), 93.1 (C), 62.7 (CH$_2$), 55.3 (2×CH$_2$), 53.2 (2×CH$_2$), 46.1 (CH$_3$), 26.5 ((CH$_3$)$_3$CSi), 17.0 ((CH$_3$)$_3$CSi), −4.23 ((CH$_3$)$_2$Si). HRMS [M+H]$^+$ C$_{30}$H$_{39}$N$_4$O$_2$SSi: Calcd. 531.2608 found 531.2612. Purity: 93.0%.

Example 25

N-(4-(3-((tert-butyldiphenylsilyl)ethynyl)phenyl)thiazol-2-yl)-4-((4-methylpiperazin-1-yl)methyl)benzamide

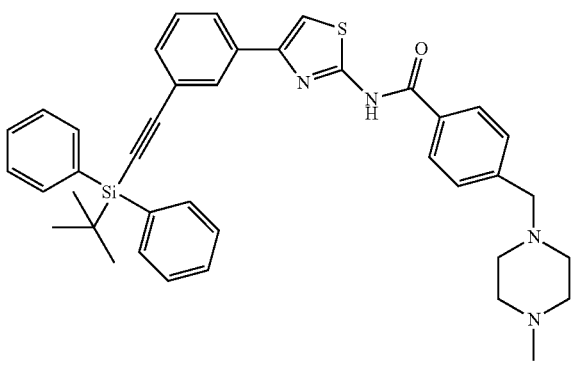 [SMILES: CN1CCN(Cc2ccc(C(=O)Nc3nc(-c4cccc(C#C[Si](c5ccccc5)(c5ccccc5)C(C)(C)C)c4)cs3)cc2)CC1]

According general procedure G using N-(4-(3-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (20.6 mg, 50%) as a yellow viscous oil. $^1$H NMR (400 MHz, CDCl$_3$) δ 7.95 (dd, J=1.5, 1.5 Hz, 1H, Har), 7.82-7.78 (m, 6H, Har), 7.71 (ddd, J=7.9, 1.5, 1.5 Hz, 1H, Har), 7.45 (ddd, J=7.7, 1.4, 1.4 Hz, 1H, Har), 7.38-7.31 (m, 9H, Har), 7.17 (s, 1H, Har), 3.48 (s, 2H, CH$_2$), 2.44 (bs, 8H, 4×CH$_2$), 2.26 (s, 3H, CH$_3$), 1.08 (s, 9H, (CH$_3$)$_3$). $^{13}$C NMR (101 MHz, CDCl$_3$) δ 164.9 (C), 158.8 (C), 149.4 (C), 144.3 (C), 136.0 (4×CH), 134.8 (C), 133.6 (2×C), 132.0 (CH), 131.0 (C), 130.0 (CH), 129.9 (2×CH), 129.8 (2×CH), 129.1 (CH), 128.1 (4×CH), 127.8 (2×CH), 126.3 (CH), 123.8 (C), 109.1 (CH), 90.0 (C), 82.9 (C), 62.6 (CH$_2$), 55.2 (2×CH$_2$), 53.0 (2×CH$_2$), 46.0 (CH$_2$), 27.5 (3×CH$_3$), 19.1 (C). HRMS [M+H]$^+$ C$_{30}$H$_{39}$N$_4$O$_2$SSi: Calcd. 531.2608 found 531.2612. Purity: 100%.

Example 26

5-(4-(4-methylpiperazine-1-carbonyl)phenyl)-N-(4-(3-((triisopropylsilyl)ethynyl)phenyl)thiazol-2-yl)furan-2-carboxamide

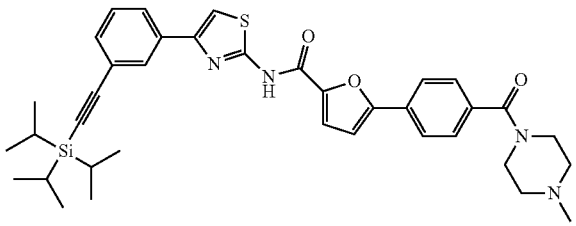 [SMILES: CC(C)[Si](C#Cc1cccc(-c2csc(NC(=O)c3ccc(-c4ccc(C(=O)N5CCN(C)CC5)cc4)o3)n2)c1)(C(C)C)C(C)C]

According general procedure G using N-(4-(3-bromophenyl)thiazol-2-yl)-5-(4-(4-methylpiperazine-1-carbonyl)phenyl)furan-2-carboxamide (30 mg, 0.054 mmol). Purification by silica gel flash chromatography (DCM/MeOH 9:1) afforded the product (11.1 mg, 32%) as a yellow viscous oil. $^1$H NMR (400 MHz, CDCl$_3$) δ 7.84 (dd, J=1.7, 1.7 Hz, 1H, Har), 7.74 (d, J=8.3 Hz, 2H, Har), 7.70 (ddd, J=7.8, 2.7, 1.4 Hz, 1H, Har), 7.50 (d, J=8.3 Hz, 2H, Har), 7.42 (ddd, J=7.8, 2.6, 1.4 Hz, 1H, Har), 7.41 (d, J=3.6 Hz, 1H, Har), 7.31 (dd, J=7.7, 7.7 Hz, 1H, Har), 7.18 (s, 1H, Har), 6.83 (d, J=3.7 Hz, 1H, Har), 3.87 (bs, 2H, CH$_2$), 3.56 (bs, 2H, CH$_2$), 2.53 (bs, 4H, 2×CH$_2$), 2.40 (s, 3H, CH$_3$), 1.15 (s, 21H, 3×(CH$_3$)$_2$CH). $^{13}$C NMR (101 MHz, CDCl$_3$) δ 169.8 (C), 157.8 (C), 156.3 (C), 155.5 (C), 149.9 (C), 145.6 (C), 136.3 (C), 134.6 (C), 132.1 (CH), 130.7 (C), 129.8 (CH), 128.9 (CH), 128.3 (2×CH), 126.3 (CH), 125.1 (2×CH), 124.4 (C), 119.7 (CH), 109.3 (CH), 107.0 (C), 91.2 (C), 55.2 (2×CH$_2$), 55.0 (2×CH$_2$), 46.1 (CH$_3$), 19.0 (3×(CH$_3$)$_2$CH), 11.7 (3×(CH$_3$)$_2$CH). HRMS [M+H]$^+$ C$_{37}$H$_{45}$N$_4$O$_3$SSi: Calcd. 653.2976 found 653.2959. Purity: 93.2%.

Example 27

N-(4-(3-((tert-butyldimethylsilyl)ethynyl)phenyl)thiazol-2-yl)-5-(4-(4-methylpiperazine-1-carbonyl)phenyl)furan-2-carboxamide

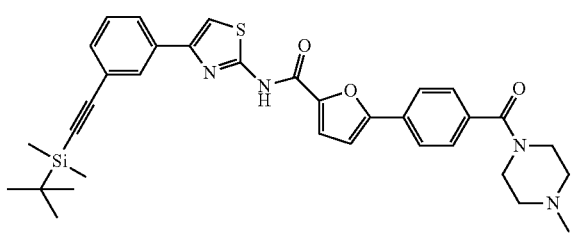 [SMILES: CN1CCN(C(=O)c2ccc(-c3ccc(C(=O)Nc4nc(-c5cccc(C#C[Si](C)(C)C(C)(C)C)c5)cs4)o3)cc2)CC1]

According general procedure G using N-(4-(3-bromophenyl)thiazol-2-yl)-5-(4-(4-methylpiperazine-1-carbonyl)phenyl)furan-2-carboxamide (30 mg, 0.054 mmol). Purification by silica gel flash chromatography (DCM/MeOH 9:1) afforded the product (7.7 mg, 24%) as a yellow viscous oil. $^1$H NMR (400 MHz, CDCl$_3$) δ 10.47 (s, 1H, NH), 7.81 (dd, J=1.4, 1.4 Hz, 1H, Har), 7.70 (d, J=8.3 Hz, 2H, Har), 7.67 (ddd, J=7.8, 2.9, 1.4 Hz, 1H, Har), 7.48 (d, J=8.4 Hz, 2H, Har), 7.39 (d, J=3.6 Hz, 1H, Har), 7.38 (ddd, J=7.8, 2.6, 1.3 Hz, 1H, Har), 7.29 (dd, J=7.8, 7.8 Hz, 1H, Har), 7.16 (s, 1H, Har), 6.81 (d, J=3.7 Hz, 1H, Har), 3.84 (bs, 2H, CH$_2$), 3.52 (bs, 2H, CH$_2$), 2.49 (bs, 4H, 2×CH$_2$), 2.37 (s, 3H, CH$_3$), 1.01 (s, 9H, 3×CH$_3$), 0.20 (s, 6H, 2×CH$_3$). $^{13}$C NMR (101 MHz, CDCl$_3$) δ 169.8 (C), 157.9 (C), 156.2 (C), 155.5 (C), 149.8 (C), 145.6 (C), 136.4 (C), 134.6 (C), 131.9 (CH), 130.6 (C), 129.9 (CH), 128.9 (CH), 128.2 (2×CH), 126.4 (CH), 125.1 (2×CH), 124.0 (C), 119.7 (CH), 109.3 (CH), 109.2 (CH), 105.7 (C), 93.2 (C), 55.3 (2×CH$_2$), 54.9 (2×CH$_2$), 46.2 (CH$_3$), 26.2 (3×CH$_3$), 17.1 (C), −4.22 (2×CH$_3$). HRMS [M+H]$^+$ C$_{34}$H$_{39}$N$_4$O$_3$SSi: Calcd. 611.2507 found 611.2488. Purity: 95.7%.

Example 28

5-(4-(4-methylpiperazine-1-carbonyl)phenyl)-N-(4-(3-(3-((triisopropylsilyl)oxy)prop-1-yn-1-yl)phenyl)thiazol-2-yl)furan-2-carboxamide

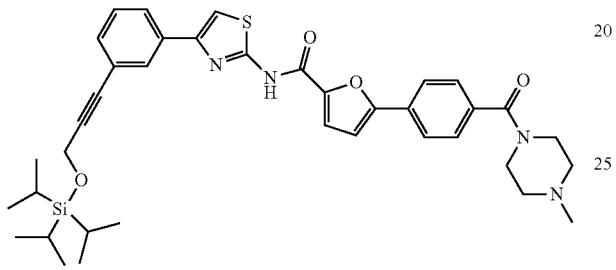

According general procedure G using N-(4-(3-bromophenyl)thiazol-2-yl)-5-(4-(4-methylpiperazine-1-carbonyl)phenyl)furan-2-carboxamide (30 mg, 0.054 mmol). Purification by silica gel flash chromatography (DCM/MeOH 9:1) afforded the product (3.5 mg, 10%) as a yellow viscous oil. $^1$H NMR (400 MHz, CDCl3) δ 10.14 (bs, 1H, NH), 7.80-7.66 (m, 4H, Har), 7.47 (d, J=7.5 Hz, 2H, Har), 7.38 (d, J=3.6 Hz, 2H, Har), 7.34-7.27 (m, 2H, Har), 7.12 (s, 1H, Har), 6.84 (d, J=3.6 Hz, 1H, Har), 4.56 (s, 2H, CH$_2$), 3.96 (bs, 4H, 2×CH$_2$), 3.43 (bs, 4H, 2×CH$_2$), 2.78 (s, 3H, CH$_3$), 1.08-1.03 (m, 21H, 3×(CH$_3$)$_2$CH). $^{13}$C NMR (101 MHz, CDCl$_3$) δ 170.1 (C), 164.6 (C), 157.7 (C), 155.8 (C), 155.3 (C), 145.9 (C), 134.3 (C), 131.7 (CH), 131.6 (C), 129.6 (CH), 129.1 (CH), 128.5 (2×CH), 126.3 (CH), 125.4 (2×CH), 123.9 (C), 119.7 (CH), 111.5 (C), 109.9 (CH), 109.2 (CH), 88.8 (C), 84.5 (C), 53.8 (2×CH$_2$), 52.8 (2×CH$_2$), 44.0 (CH$_3$), 30.0 (CH$_2$), 18.3 (3×(CH$_3$)$_2$CH), 12.4 (3×(CH$_3$)$_2$CH). HRMS [M+H]$^+$ C$_{38}$H$_{47}$N$_4$O$_4$SSi: Calcd. 683.3082 found 638.3075. Purity: 61%.

Example 29

5-(4-(4-methylpiperazine-1-carbonyl)phenyl)-N-(4-(3-((2-(trifluoromethyl)phenyl)ethynyl)phenyl)thiazol-2-yl)furan-2-carboxamide

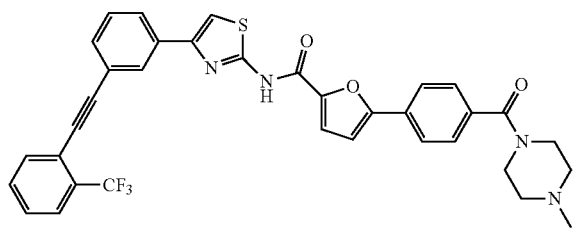 [SMILES: CN1CCN(C(=O)c2ccc(-c3ccc(C(=O)Nc4nc(-c5cccc(C#Cc6ccccc6C(F)(F)F)c5)cs4)o3)cc2)CC1]

According general procedure G using N-(4-(3-bromophenyl)thiazol-2-yl)-5-(4-(4-methylpiperazine-1-carbonyl)phenyl)furan-2-carboxamide (30 mg, 0.054 mmol). Purification by silica gel flash chromatography (DCM/MeOH 9:1) afforded the product (13.8 mg, 40%) as a yellow viscous oil. $^1$H NMR (500 MHz, CDCl$_3$) δ 10.33 (s, 1H, NH), 7.86 (s, 1H, Har), 7.69 (d, J=8.0 Hz, 2H, Har), 7.62 (dd, J=7.5, 4.3 Hz, 2H, Har), 7.50-7.27 (m, 8H, Har), 7.14 (s, 1H, Har), 6.78 (d, J=3.6 Hz, 1H, Har), 3.88 (bs, 2H, CH$_2$), 3.66 (bs, 2H, CH$_2$), 2.69 (bs, 4H, 2×CH$_2$), 2.47 (s, 3H, CH$_3$). $^{13}$C NMR (101 MHz, CDCl3) δ 169.9 (C), 157.9 (C), 156.1 (C), 155.5 (C), 149.7 (C), 145.7 (C), 134.8 (C), 134.2 (CH), 131.9 (C), 131.8 (CH), 131.8 (q, J=30.3 Hz, C), 131.6 (CH), 131.0 (C), 129.6 (CH), 129.2 (CH), 128.4 (CH), 128.3 (2×CH), 127.5 (CH), 126.8 (CH), 126.3 (q, J=4.7 Hz, CH), 125.2 (2×CH), 123.9 (d, J=273.6 Hz, C), 123.6 (C), 121.7 (d, J=1.2 Hz, C), 119.7 (CH), 109.4 (d, J=3.5 Hz, CH), 94.9 (C), 85.9 (C), 54.6 (2×CH$_2$), 54.5 (2×CH$_2$), 45.3 (CH$_3$). HRMS [M+H]$^+$ C$_{35}$H$_{28}$F$_3$N$_4$O$_3$S: Calcd. 641.1829 found 641.1805. Purity: 91.1%.

Example 30

4-((4-methylpiperazin-1-yl)methyl)-N-(4-(3-(3-(trityloxy)prop-1-yn-1-yl)phenyl)thiazol-2-yl)benzamide

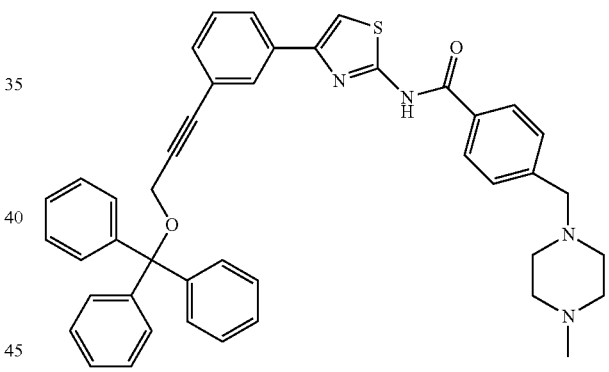

According general procedure G using N-(4-(3-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (11.4 mg, 26%) as a yellow viscous oil. $^1$H NMR (300 MHz, CDCl$_3$) δ 9.90 (bs, 1H, NH), 7.88 (dd, J=1.5, 1.5 Hz, 1H, Har), 7.88 (d, J=8.1 Hz, 2H, Har), 7.75 (ddd, J=6.7, 2.0, 2.0 Hz, 1H, Har), 7.55-7.50 (m, 6H, Har), 7.46 (d, J=8.2 Hz, 2H, Har), 7.37-7.30 (m, 9H, Har), 7.28 (dd, J=1.3, 1.3 Hz, 1H, Har), 7.24 (ddd, J=6.0, 1.2, 1.2 Hz, 1H, Har), 7.21 (s, 1H, Har), 4.01 (s, 2H, CH$_2$), 3.57 (s, 2H, CH$_2$), 2.51 (bs, 8H, 4×CH$_2$), 2.33 (s, 3H, CH$_3$). $^{13}$C NMR (101 MHz, CDCl$_3$) δ 164.8 (C), 158.6 (C), 149.6 (C), 144.4 (C), 143.8 (4×C), 134.7 (C), 131.6 (CH), 130.9 (C), 129.8 (2×CH), 129.7 (CH), 129.0 (6×CH), 128.3 (6×CH), 127.7 (2×CH), 127.5 (4×CH), 126.2 (CH), 123.7 (C), 108.9 (CH), 87.9 (C), 86.5 (C), 85.4 (C), 62.7 (CH$_2$), 55.3 (2×CH$_2$), 54.0 (CH$_2$), 53.2 (2×CH$_2$), 46.2 (CH$_3$). HRMS [M+H]$^+$ C$_{44}$H$_{41}$N$_4$O$_2$S: Calcd. 689.2945 found 689.2911. Purity: 100.0%.

Example 31

N-(4-(3-((2-fluorophenyl)ethynyl)phenyl)thiazol-2-yl)-4-((4-methylpiperazin-1-yl)methyl)benzamide

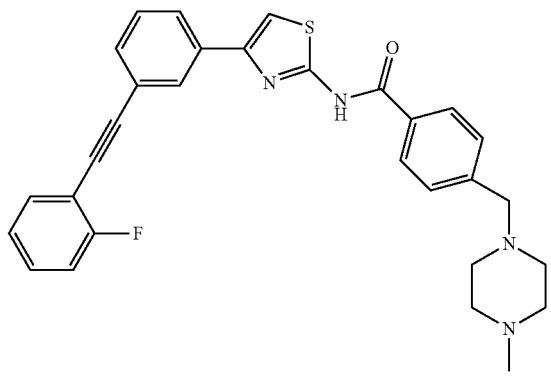 [SMILES: CN1CCN(Cc2ccc(C(=O)Nc3nc(-c4cccc(C#Cc5ccccc5F)c4)cs3)cc2)CC1]

According general procedure G using N-(4-(3-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (12 mg, 37%) as a yellow viscous oil. $^1$H NMR (400 MHz, CDCl$_3$) δ 10.59 (bs, 1H, NH), 7.86 (dd, J=1.6, 1.6 Hz, 1H, Har), 7.74 (d, J=8.2 Hz, 2H, Har), 7.65 (ddd, J=7.9, 1.3, 1.3 Hz, 1H, Har), 7.47 (ddd, J=7.3, 7.3, 1.7 Hz, 1H, Har), 7.36 (ddd, J=7.7, 1.3, 1.3 Hz, 1H, Har), 7.30 (d, J=8.3 Hz, 2H, Har), 7.28-7.21 (m, 2H, Har), 7.16 (s, 1H, Har), 7.10-7.06 (m, 1H, Har), 7.06-7.02 (m, 1H, Har), 3.46 (s, 2H, CH$_2$), 2.41 (bs, 8H, 4×CH$_2$), 2.24 (s, 3H, CH$_3$). $^{13}$C NMR (101 MHz, CDCl$_3$) δ 165.3 (C), 163.0 (d, J=251.7 Hz, C), 159.3 (C), 149.6 (C), 144.3 (C), 134.8 (C), 133.9 (d, J=0.9 Hz, CH), 131.5 (CH), 131.0 (C), 130.5 (d, J=7.9 Hz, CH), 129.7 (3×CH), 129.1 (CH), 127.9 (2×CH), 126.6 (CH), 124.4 (d, J=3.7 Hz, CH), 123.7 (C), 116.0 (d, J=20.9 Hz, CH), 112.2 (d, J=15.6 Hz, C), 109.1 (CH), 94.6 (d, J=3.2 Hz, C), 83.4 (C), 62.7 (CH$_2$), 55.3 (2×CH$_2$), 53.2 (2×CH$_2$), 46.2 (CH$_3$). HRMS [M+H]$^+$ C$_{30}$H$_{28}$FN$_4$OS: Calcd. 511.1962 found 511.1948. Purity: 100.0%.

Example 32

N-(4-(3-((4-fluorophenyl)ethynyl)phenyl)thiazol-2-yl)-4-((4-methylpiperazin-1-yl)methyl)benzamide

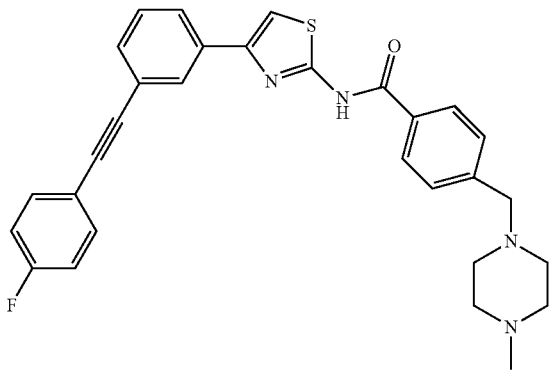 [SMILES: CN1CCN(Cc2ccc(C(=O)Nc3nc(-c4cccc(C#Cc5ccc(F)cc5)c4)cs3)cc2)CC1]

According general procedure G using N-(4-(3-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (14.2 mg, 44%) as a yellow viscous oil. $^1$H NMR (400 MHz, CDCl$_3$) δ 10.49 (s, 1H, NH), 7.92 (dd, J=1.3, 1.3 Hz, 1H, Har), 7.83 (dd, J=8.1, 1.6 Hz, 2H, Har), 7.74-7.70 (m, 1H, Har), 7.56-7.49 (m, 2H, Har), 7.42-7.36 (m, 3H, Har), 7.32 (ddd, J=7.7, 7.7, 1.8 Hz, 1H, Har), 7.23 (d, J=1.8 Hz, 1H, Har), 7.06 (ddd, J=8.6, 8.6, 1.8 Hz, 1H, Har), 3.54 (s, 2H, CH$_2$), 2.50 (bs, 8H, 4×CH$_2$), 2.33 (s, 3H, CH$_3$). $^{13}$C NMR (101 MHz, CDCl$_3$) δ 165.1 (C), 162.9 (d, J=249.5 Hz, C), 159.1 (C), 149.5 (C), 144.2 (C), 134.7 (C), 133.9 (d, J=8.3 Hz, 2×CH), 131.2 (CH), 130.9 (C), 129.7 (2×CH), 129.3 (d, J=44.3 Hz, 2×CH), 127.8 (2×CH), 126.2 (CH), 123.8 (C), 119.5 (C), 116.0 (d, J=22.1 Hz, 2×CH), 109.0 (CH), 89.1 (C), 88.9 (C), 62.6 (CH$_2$), 55.2 (2×CH$_2$), 53.1 (2×CH$_2$), 46.0 (CH$_3$). HRMS [M+H]$^+$ C$_{30}$H$_{28}$FN$_4$OS: Calcd. 511.1962 found 511.1969. Purity: 100.0%.

Example 33

N-(4-(3-((3,5-bis(trifluoromethyl)phenyl)ethynyl)phenyl)thiazol-2-yl)-4-((4-methylpiperazin-1-yl)methyl)benzamide

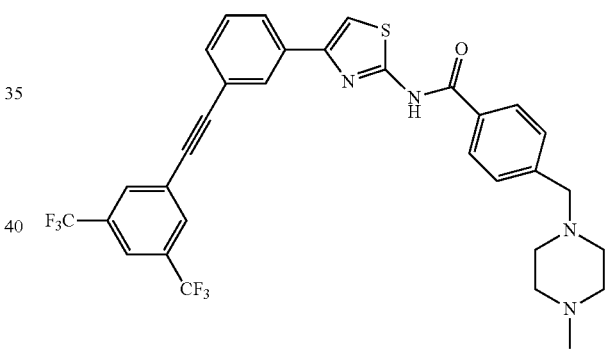

According general procedure G using N-(4-(3-bromophenyl)thiazol-2-yl)-4-((4-methylpiperazin-1-yl)methyl)benzamide (60 mg, 0.127 mmol). Purification by silica gel flash chromatography (DCM/MeOH 9:1) afforded the product (63 mg, 79%) as a yellow viscous oil. $^1$H NMR (400 MHz, CDCl$_3$) δ 11.04 (bs, 1H, NH), 7.97 (bs, 2H, Har), 7.92 (dd, J=1.5, 1.5 Hz, 2H, Har), 7.82 (bs, 1H, Har), 7.78 (d, J=8.2 Hz, 2H, Har), 7.71 (ddd, J=7.8, 1.3, 1.3 Hz, 1H, Har), 7.37 (ddd, J=7.7, 1.3, 1.3 Hz, 1H, Har), 7.31 (d, J=8.1 Hz, 2H, Har), 7.29 (dd, J=7.7, 7.7 Hz, 1H, Har), 7.24 (s, 1H, Har), 3.49 (s, 2H, CH$_2$), 2.45 (bs, 8H, 4×CH$_2$), 2.31 (s, 3H, CH$_3$). $^{13}$C NMR (101 MHz, CDCl$_3$) δ 165.4 (C), 159.6 (C), 149.2 (C), 144.2 (C), 134.8 (C), 132.4 (q, J=33.8 Hz, 2×C), 131.8 (CH), 131.8 (CH), 131.2 (CH), 130.9 (C), 129.9 (CH), 129.5 (2×CH), 129.1 (CH), 127.8 (2×CH), 126.9 (CH), 125.8 (C), 123.3 (d, J=267.3 Hz, 2×C), 122.6 (C), 122.1-121.8 (m, CH), 109.2 (CH), 92.8 (C), 86.9 (C), 62.6 (CH$_2$), 55.3 (2×CH$_2$), 53.1 (2×CH$_2$), 46.1 (CH$_3$). HRMS [M+H]$^+$ C$_{32}$H$_{27}$F$_6$N$_4$OS: Calcd. 629.1804 found 629.1779. Purity: 100.0%.

Example 34

N-(4-(3-((3,5-bis(trifluoromethyl)phenyl)ethynyl)phenyl)thiazol-2-yl)-5-(4-(4-methylpiperazine-1-carbonyl)phenyl)furan-2-carboxamide

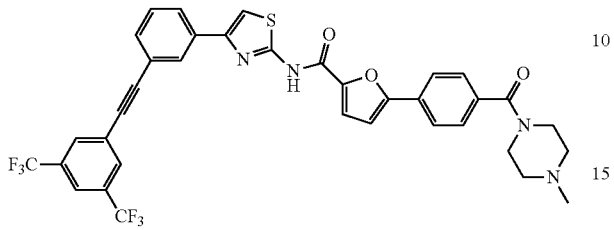

According general procedure G using N-(4-(3-bromophenyl)thiazol-2-yl)-5-(4-(4-methylpiperazine-1-carbonyl)phenyl)furan-2-carboxamide (30 mg, 0.054 mmol). Purification by silica gel flash chromatography (DCM/MeOH 9:1) afforded the product (7.8 mg, 21%) as a yellow viscous oil. $^1$H NMR (400 MHz, CDCl$_3$) δ 10.92 (bs, 1H, NH), 8.01 (bs, 2H, Har), 7.92 (bs, 1H, Har), 7.84 (bs, 1H, Har), 7.67-7.64 (m, 1H, Har), 7.62 (d, J=8.0 Hz, 2H, Har), 7.46 (d, J=8.3 Hz, 2H, Har), 7.43-7.38 (m, 2H, Har), 7.33 (dd, J=7.7, 7.7 Hz, 1H, Har), 7.19 (s, 1H, Har), 6.77 (d, J=3.6 Hz, 1H, Har), 3.84 (bs, 2H, CH$_2$), 3.50 (bs, 2H, CH$_2$), 2.53 (bs, 2H, CH$_2$), 2.42 (bs, 2H, CH$_2$), 2.36 (s, 3H, CH$_3$). $^{13}$C NMR (101 MHz, CDCl$_3$) δ 169.9 (C), 158.5 (C), 156.3 (C), 155.8 (C), 149.6 (C), 145.6 (C), 136.6 (C), 134.9 (C), 132.4 (q, J=33.6 Hz, 2×C), 132.0 (CH), 131.9 (CH), 131.4 (CH), 130.6 (C), 130.1 (CH), 129.3 (CH), 128.2 (2×CH), 127.1 (CH), 125.9 (C), 125.1 (2×CH), 123.4 (d, J=277.4 Hz, 2×C), 122.7 (C), 122.1-122.0 (m, CH), 119.9 (CH), 109.6 (CH), 109.2 (CH), 92.8 (C), 87.1 (C), 55.6 (2×CH$_2$), 55.1 (2×CH$_2$), 46.3 (CH$_3$). HRMS [M+H]$^+$ C$_{36}$H$_{27}$F$_6$N$_4$O$_3$S: Calcd. 709.1703 found 709.1670. Purity: 96.3%.

Example 35

4-((4-methylpiperazin-1-yl)methyl)-N-(4-(4-((triisopropylsilyl)ethynyl)phenyl)thiazol-2-yl)benzamide

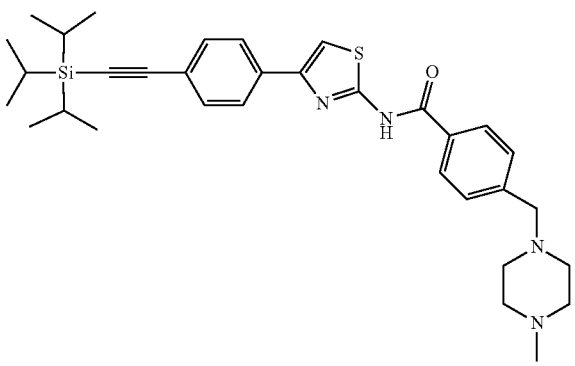 [SMILES: CC(C)[Si](C#Cc1ccc(-c2csc(NC(=O)c3ccc(CN4CCN(C)CC4)cc3)n2)cc1)(C(C)C)C(C)C]

According general procedure G using N-(4-(4-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (24 mg, 66%) as a yellow viscous oil. $^1$H NMR (400 MHz, CDCl$_3$) δ 10.61 (bs, 1H, NH), 7.79 (d, J=8.2 Hz, 2H, Har), 7.67 (d, J=8.3 Hz, 2H, Har), 7.41 (d, J=8.3 Hz, 2H, Har), 7.35 (d, J=8.2 Hz, 2H, Har), 7.21 (s, 1H, Har), 3.51 (s, 2H, CH$_2$), 2.46 (bs, 8H, 4×CH$_2$), 2.33 (s, 3H, CH$_3$), 1.13 (s, 21H, 3×(CH$_3$)$_2$CH). $^{13}$C NMR (101 MHz, CDCl$_3$) δ 165.23 (C), 159.14 (C), 149.76 (C), 144.20 (C), 134.22 (C), 132.63 (2×CH), 130.92 (C), 129.62 (2×CH), 127.77 (2×CH), 126.00 (2×CH), 123.31 (C), 109.14 (CH), 107.19 (C), 91.91 (C), 62.68 (CH$_2$), 55.31 (2×CH$_2$), 53.17 (2×CH$_2$), 46.14 (CH$_3$), 19.02 (3×(CH$_3$)$_2$CH), 11.64 (3×(CH$_3$)$_2$CH). HRMS [M+H]$^+$ C$_{33}$H$_{45}$N$_4$OSSi: Calcd. 573.3078 found 573.3064. Purity: 100.0%.

Example 36

N-(4-(4-((3,5-bis(trifluoromethyl)phenyl)ethynyl)phenyl)thiazol-2-yl)-4-((4-methylpiperazin-1-yl)methyl)benzamide

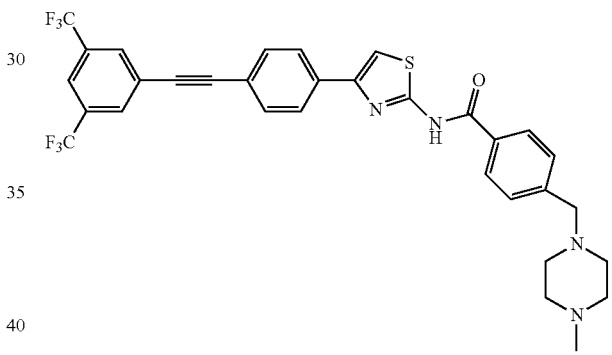

According general procedure G using N-(4-(4-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (27 mg, 68%) as a yellow viscous oil. $^1$H NMR (400 MHz, CDCl$_3$) δ 10.37 (bs, 1H, NH), 7.95 (bs, 2H, Har), 7.83 (d, J=8.3 Hz, 2H, Har), 7.82-7.81 (m, 1H, Har), 7.79 (d, J=8.4 Hz, 2H, Har), 7.53 (d, J=8.4 Hz, 2H, Har), 7.40 (d, J=8.2 Hz, 2H, Har), 7.27 (d, J=2.1 Hz, 1H, Har), 3.54 (s, 2H, CH$_2$), 2.50 (bs, 8H, 4×CH$_2$), 2.33 (s, 3H, CH$_3$). $^{13}$C NMR (101 MHz, CDCl$_3$) δ 165.1 (C), 159.1 (C), 149.4 (C), 144.3 (C), 135.2 (C), 132.5 (2×CH), 132.3 (d, J=33.8 Hz, 2×C), 131.7 (CH), 131.7 (CH), 130.9 (C), 129.7 (2×CH), 127.8 (2×CH), 126.3 (2×CH), 125.9 (C), 123.3 (d, J=272.9 Hz, 2×C), 121.9-121.8 (m, CH), 121.5 (C), 109.7 (CH), 93.0 (C), 87.5 (C), 62.7 (CH$_2$), 55.3 (2×CH$_2$), 53.1 (2×CH$_2$), 46.1 (CH$_3$). HRMS [M+H]$^+$ C$_{32}$H$_{27}$F$_6$N$_4$OS: Calcd. 629.1804 found 629.1791. Purity: 100.0%.

Example 37

N-(4-(4-((tert-butyldimethylsilyl)ethynyl)phenyl)thiazol-2-yl)-4-((4-methylpiperazin-1-yl)methyl)benzamide

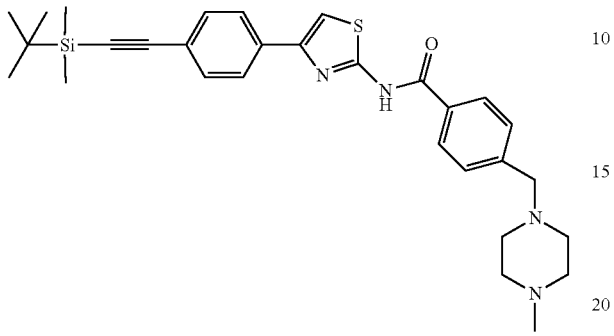

According general procedure G using N-(4-(4-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (20.7 mg, 62%) as a yellow viscous oil. $^1$H NMR (500 MHz, CDCl$_3$) δ 10.76 (bs, 1H, NH), 7.71 (d, J=8.3 Hz, 2H, Har), 7.60 (d, J=8.5 Hz, 2H, Har), 7.33 (d, J=8.5 Hz, 2H, Har), 7.26 (d, J=8.2 Hz, 2H, Har), 7.16 (s, 1H, Har), 3.45 (s, 2H, CH$_2$), 2.44 (bs, 8H, 4×CH$_2$), 2.31 (s, 3H, CH$_3$), 0.93 (s, 9H, (CH$_3$)$_3$CSi), 0.12 (s, 6H, (CH$_3$)$_2$Si). $^{13}$C NMR (126 MHz, CDCl$_3$) δ 165.3 (C), 159.2 (C), 149.6 (C), 143.9 (C), 134.2 (C), 132.6 (2×CH), 130.9 (C), 129.6 (2×CH), 127.8 (2×CH), 125.9 (2×CH), 122.9 (C), 109.2 (CH), 105.7 (C), 93.8 (C), 62.5 (CH$_2$), 55.1 (2×CH$_2$), 52.8 (2×CH$_2$), 45.9 (CH$_3$), 26.5 ((CH$_3$)$_3$CSi), 17.1 ((CH$_3$)$_3$CSi), −4.3 ((CH$_3$)$_2$Si). HRMS [M+H]$^+$ C$_{30}$H$_{39}$N$_4$OSSi: Calcd. 531.2608 found 531.2595. Purity: 94.5%.

Example 38

4-(morpholinomethyl)-N-(4-(3-((triisopropylsilyl)ethynyl)phenyl)thiazol-2-yl)benzamide

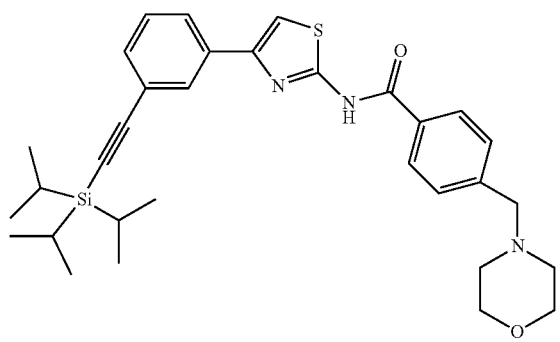 [SMILES: CC(C)[Si](C#Cc1cccc(-c2csc(NC(=O)c3ccc(CN4CCOCC4)cc3)n2)c1)(C(C)C)C(C)C]

According general procedure G using N-(4-(3-bromophenyl)thiazol-2-yl)-4-(morpholinomethyl)benzamide (32.5 mg, 0.071 mmol). Purification by silica gel flash chromatography (DCM/MeOH 9:1) afforded the product (39.7 mg, quanti.) as a yellow viscous oil. $^1$H NMR (400 MHz, CDCl$_3$) δ 10.76 (bs, 1H, NH), 7.87 (dd, J=1.5, 1.5 Hz, 1H, Har), 7.83 (d, J=8.2 Hz, 2H, Har), 7.71 (ddd, J=7.8, 1.4, 1.4 Hz, 1H, Har), 7.41-7.36 (m, 3H, Har), 7.30 (s, 1H, Har), 7.30-7.28 (m, 1H, Har), 3.75 (t, J=4.5 Hz, 4H, 2×CH$_2$), 3.54 (s, 2H, CH$_2$), 2.45 (t, J=4.3 Hz, 4H, 2×CH$_2$), 1.17 (s, 21H, 3×(CH$_3$)$_2$CH). $^{13}$C NMR (101 MHz, CDCl$_3$) δ 165.2 (C), 159.2 (C), 149.5 (C), 143.8 (C), 134.5 (C), 131.8 (CH), 131.0 (C), 129.7 (CH), 129.6 (2×CH), 128.8 (CH), 127.8 (2×CH), 126.1 (CH), 124.2 (C), 109.0 (CH), 107.0 (C), 91.2 (C), 67.2 (2×CH$_2$), 63.1 (CH$_2$), 53.9 (2×CH$_2$), 19.0 (3×(CH$_3$)$_2$CH), 11.6 (3×(CH$_3$)$_2$CH). HRMS [M+H]$^-$ C$_{32}$H$_{42}$N$_3$O$_2$SSi: Calcd. 560.2762 found 560.2741. Purity: 98.2%.

Example 39

N-(4-(3-((3,5-bis(trifluoromethyl)phenyl)ethynyl)phenyl)thiazol-2-yl)-4-(morpholinomethyl)benzamide

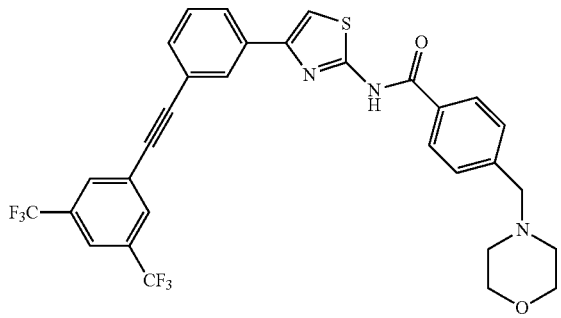 [SMILES: O=C(Nc1nc(-c2cccc(C#Cc3cc(C(F)(F)F)cc(C(F)(F)F)c3)c2)cs1)c1ccc(CN2CCOCC2)cc1]

According general procedure G using N-(4-(3-bromophenyl)thiazol-2-yl)-4-(morpholinomethyl)benzamide (30 mg, 0.065 mmol). Purification by silica gel flash chromatography (EA/MeOH 98:2) afforded the product (34.1 mg, 85%) as a yellow viscous oil. $^1$H NMR (400 MHz, CDCl$_3$) δ 10.69 (bs, 1H, NH), 7.99 (bs, 2H, Har), 7.95 (dd, J=1.5, 1.5 Hz, 1H, Har), 7.86-7.82 (m, 3H, Har), 7.76 (ddd, J=7.8, 1.4, 1.4 Hz, 1H, Har), 7.43-7.38 (m, 3H, Har), 7.34 (dd, J=7.7, 7.7 Hz, 1H, Har), 7.26 (s, 1H, Har), 3.74 (bs, 4H, 2×CH$_2$), 3.55 (s, 2H, CH$_2$), 2.45 (bs, 4H, 2×CH$_2$). $^{13}$C NMR (101 MHz, CDCl$_3$) δ 165.1 (C), 159.3 (C), 149.2 (C), 139.6 (C), 134.8 (C), 132.3 (q, J=33.7 Hz, 2×C), 131.8 (CH), 131.8 (CH), 131.3 (CH), 129.9 (2×CH), 129.2 (2×CH), 127.9 (2×CH), 127.0 (CH), 125.8 (C), 123.3 (d, J=272.8 Hz, 2×C), 122.6 (C), 122.1-122.0 (m, CH), 121.9 (C), 109.3 (CH), 92.8 (C), 87.0 (C), 67.1 (2×CH$_2$), 63.1 (CH$_2$), 53.8 (2×CH$_2$). HRMS [M+H]$^+$ C$_{31}$H$_{24}$F$_6$N$_3$O$_2$S: Calcd. 616.1488 found 616.1469. Purity: 93.9%.

Example 40

N-(4-(3-((tert-butyldimethylsilyl)ethynyl)phenyl)thiazol-2-yl)-4-(morpholinomethyl)benzamide

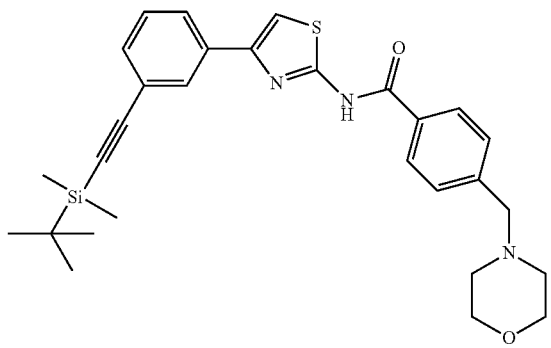 [SMILES: CC(C)(C)[Si](C)(C)C#Cc1cccc(-c2csc(NC(=O)c3ccc(CN4CCOCC4)cc3)n2)c1]

According general procedure G using N-(4-(3-bromophenyl)thiazol-2-yl)-4-(morpholinomethyl)benzamide (30 mg, 0.065 mmol). Purification by silica gel flash chromatography (EA/MeOH 98:2) afforded the product (33.0 mg, 97%) as a yellow viscous oil. $^1$H NMR (400 MHz, CDCl$_3$) δ 10.93 (bs, 1H, NH), 7.80 (dd, J=1.5, 1.5 Hz, 1H, Har), 7.77 (d, J=8.2 Hz, 2H, Har), 7.65 (ddd, J=7.8, 1.3, 1.3 Hz, 1H, Har), 7.32 (d, J=8.1 Hz, 2H, Har), 7.31 (ddd, J=7.7, 1.3, 1.3 Hz, 1H, Har), 7.22 (s, 1H, Har), 7.21 (dd, J=7.7, 7.7 Hz, 1H, Har), 3.72 (t, J=4.3 Hz, 4H, 2×CH$_2$), 3.50 (s, 2H, CH$_2$), 2.41 (t, J=4.3 Hz, 4H, 2×CH$_2$), 1.00 (s, 9H, (CH$_3$)$_3$CSi), 0.20 (s, 6H, (CH$_3$)$_2$Si). $^{13}$C NMR (101 MHz, CDCl$_3$) δ 165.4 (C), 159.4 (C), 149.5 (C), 143.7 (C), 134.4 (C), 131.7 (CH), 131.0 (C), 129.8 (CH), 129.6 (2×CH), 128.8 (CH), 127.8 (2×CH), 126.2 (CH), 123.9 (C), 109.0 (CH), 105.7 (C), 93.1 (C), 67.2 (2×CH$_2$), 63.1 (CH$_2$), 53.9 (2×CH$_2$), 26.5 ((CH$_3$)$_3$CSi), 17.0 ((CH$_3$)$_3$CSi), −4.2 ((CH$_3$)$_2$Si). HRMS [M+H]$^+$ C$_{29}$H$_{36}$N$_3$O$_2$SSi: Calcd. 518.2292 found 518.2274. Purity: 100.0%.

Example 41

N-(4-(3-((tert-butyldiphenylsilyl)ethynyl)phenyl)thiazol-2-yl)-4-(morpholinomethyl)benzamide

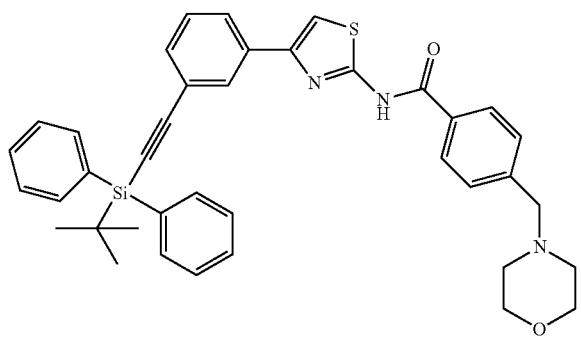 [SMILES: CC(C)(C)[Si](C#Cc1cccc(-c2csc(NC(=O)c3ccc(CN4CCOCC4)cc3)n2)c1)(c1ccccc1)c1ccccc1]

According general procedure G using N-(4-(3-bromophenyl)thiazol-2-yl)-4-(morpholinomethyl)benzamide (30 mg, 0.065 mmol). Purification by silica gel flash chromatography (EA/MeOH 98:2) afforded the product (38.5 mg, 92%) as a yellow viscous oil. $^1$H NMR (400 MHz, CDCl$_3$) δ 10.76 (bs, 1H, NH), 7.96 (dd, J=1.5, 1.5 Hz, 1H, Har), 7.90-7.86 (m, 4H, Har), 7.81 (d, J=8.1 Hz, 2H, Har), 7.74 (ddd, J=7.9, 1.5, 1.5 Hz, 1H, Har), 7.49 (ddd, J=7.7, 1.4, 1.4 Hz, 1H, Har), 7.45-7.40 (m, 6H, Har), 7.37 (d, J=8.1 Hz, 2H, Har), 7.31 (dd, J=7.8, 7.8 Hz, 1H, Har), 7.25 (s, 1H, Har), 3.70 (t, J=4.4 Hz, 4H, 2×CH$_2$), 3.51 (s, 2H, CH$_2$), 2.40 (t, J=4.3 Hz, 4H, 2×CH$_2$), 1.17 (s, 9H, (CH$_3$)$_3$CSi). $^{13}$C NMR (101 MHz, CDCl$_3$) δ 165.2 (C), 159.2 (C), 149.4 (C), 143.7 (C), 135.9 (CH), 134.7 (C), 133.5 (2×C), 132.0 (CH), 131.0 (C), 129.9 (CH), 129.7 (CH), 129.0 (CH), 128.1 (CH), 127.8 (CH), 126.7 (CH), 123.7 (C), 109.2 (CH), 109.0 (C), 90.0 (C), 67.2 (2×CH$_2$), 63.1 (CH$_2$), 53.8 (2×CH$_2$), 27.5 (3×CH$_3$), 19.1 ((CH$_3$)$_3$CSi). HRMS [M+H]$^+$ C$_{39}$H$_{40}$N$_3$O$_2$SSi: Calcd. 642.2605 found 642.2604. Purity: 100.0%.

Example 42

4-((4-methylpiperazin-1-yl)methyl)-N-(4-(3-((2-(trifluoromethoxy)phenyl)ethynyl)phenyl)thiazol-2-yl)benzamide

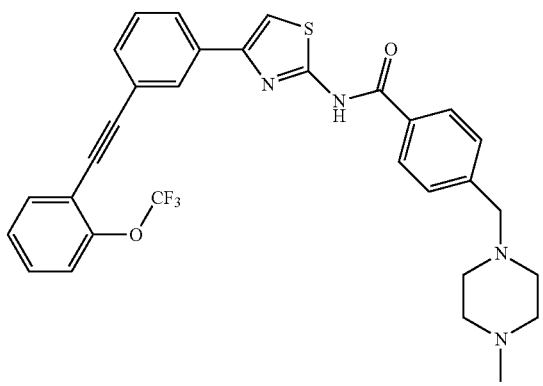 [SMILES: CN1CCN(Cc2ccc(C(=O)Nc3nc(-c4cccc(C#Cc5ccccc5OC(F)(F)F)c4)cs3)cc2)CC1]

According general procedure G using N-(4-(3-bromophenyl)thiazol-2-yl)-4-((4-methylpiperazin-1-yl)methyl)benzamide (30 mg, 0.064 mmol). Purification by silica gel flash chromatography (DCM/MeOH 9:1) afforded the product (24.7 mg, 68%) as a yellow viscous oil. $^1$H NMR (400 MHz, CDCl$_3$) δ 10.66 (bs, 1H, NH), 7.91 (dd, J=1.5, 1.5 Hz, 1H, Har), 7.80 (d, J=8.2 Hz, 2H, Har), 7.73 (ddd, J=7.8, 1.4, 1.4 Hz, 1H, Har), 7.63-7.59 (m, 1H, Har), 7.42 (ddd, J=7.7, 1.4, 1.4 Hz, 1H, Har), 7.39-7.34 (m, 3H, Har), 7.34-7.28 (m, 3H, Har), 7.24 (s, 1H, Har), 3.52 (s, 2H, CH$_2$), 2.49 (bs, 8H, 2×CH$_2$), 2.32 (s, 3H, CH$_3$). $^{13}$C NMR (101 MHz, CDCl$_3$) δ 165.3 (C), 159.2 (C), 149.6 (C), 149.4 (C), 144.2 (C), 134.7 (C), 133.9 (CH), 131.5 (CH), 130.9 (C), 129.9 (CH), 129.6 (2×CH), 129.5 (CH), 129.1 (CH), 127.8 (2×CH), 127.1 (CH), 126.6 (CH), 123.5 (C), 121.7 (CH), 120.9 (d, J=258.3 Hz, C), 118.3 (C), 109.1 (CH), 94.7 (C), 84.1 (C), 62.6 (CH$_2$), 55.2 (2×CH$_2$), 53.0 (2×CH$_2$), 46.0 (CH$_3$). HRMS [M+H]$^+$ C$_{31}$H$_{28}$F$_3$N$_4$O$_2$S: Calcd. 577.1880 found 577.1871. Purity: 91.7%.

Example 43

5-(4-(4-methylpiperazine-1-carbonyl)phenyl)-N-(4-(3-((2-(trifluoromethoxy)phenyl)ethynyl)phenyl)thiazol-2-yl)furan-2-carboxamide

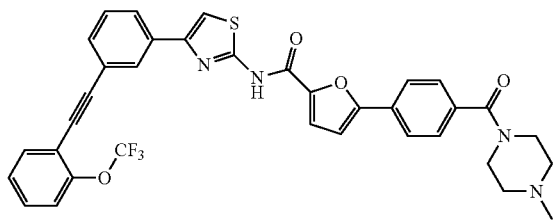 [SMILES: CN1CCN(C(=O)c2ccc(-c3ccc(C(=O)Nc4nc(-c5cccc(C#Cc6ccccc6OC(F)(F)F)c5)cs4)o3)cc2)CC1]

According general procedure G using N-(4-(3-bromophenyl)thiazol-2-yl)-5-(4-(4-methylpiperazine-1-carbonyl)phenyl)furan-2-carboxamide (30 mg, 0.054 mmol). Purification by silica gel flash chromatography (DCM/MeOH 9:1) afforded the product (20.5 mg, 58%) as a yellow viscous oil. $^1$H NMR (400 MHz, CDCl$_3$) δ 10.72 (bs, 1H, NH), 7.85 (dd, J=1.5, 1.5 Hz, 1H, Har), 7.70 (ddd, J=7.8, 1.4, 1.4 Hz, 1H, Har), 7.66 (d, J=8.2 Hz, 2H, Har), 7.64-7.61 (m, 1H, Har), 7.47 (d, J=8.4 Hz, 2H, Har), 7.44 (ddd, J=7.5, 1.4, 1.4 Hz, 1H, Har), 7.41-7.36 (m, 3H, Har), 7.33 (d, J=7.0 Hz, 2H, Har), 7.17 (s, 1H, Har), 6.78 (d, J=3.7 Hz, 1H, Har), 3.84 (bs, 2H, CH$_2$), 3.50 (bs, 2H, CH$_2$), 2.53 (bs, 2H, CH$_2$), 2.41 (bs, 2H, CH$_2$), 2.35 (s, 3H, CH$_3$). $^{13}$C NMR (101 MHz, CDCl$_3$) δ 169.8 (C), 158.1 (C), 156.2 (C), 155.6 (C), 149.7 (C), 149.6 (C), 145.5 (C), 136.4 (C), 134.7 (C), 133.9 (CH), 131.5 (CH), 130.6 (C), 129.9 (CH), 129.6 (CH), 129.1 (CH), 128.8 (CH), 128.2 (CH), 127.4 (CH), 127.2 (CH), 126.6 (CH), 125.0 (CH), 123.5 (C), 121.7 (CH), 121.0 (d, J=258.2 Hz, C), 119.7 (CH), 118.3 (C), 109.3 (CH), 109.1 (CH), 94.6 (C), 84.10 (C), 55.4 (2×CH$_2$), 54.9 (2×CH$_2$), 46.2 (CH$_3$). HRMS [M+H]$^+$ C$_{35}$H$_{28}$F$_3$N$_4$O$_4$S: Calcd. 657.1778 found 657.1774. Purity: 100.0%.

Example 44

4-(((2-(dimethylamino)ethyl)amino)methyl)-N-(4-(3-((triisopropylsilyl)ethynyl)phenyl)thiazol-2-yl)benzamide

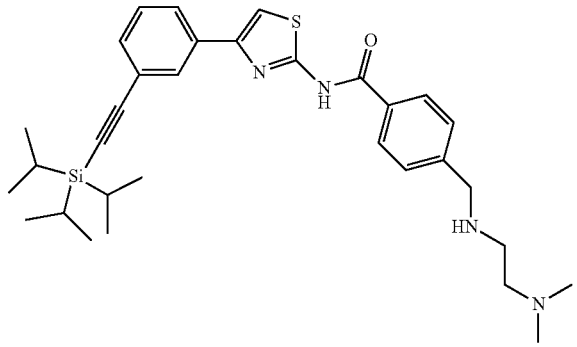 [SMILES: CC(C)[Si](C#Cc1cccc(-c2csc(NC(=O)c3ccc(CNCCN(C)C)cc3)n2)c1)(C(C)C)C(C)C]

According general procedure G using N-(4-(3-bromophenyl)thiazol-2-yl)-4-(((2-(dimethylamino)ethyl)amino)methyl)benzamide (49.3 mg, 0.107 mmol). Purification by silica gel flash chromatography (DCM/MeOH 9:1) afforded the product (27.8 mg, 47%) as a yellow viscous oil. $^1$H NMR (400 MHz, CDCl$_3$) δ 7.77 (d, J=8.2 Hz, 2H, Har), 7.75 (dd, J=1.5, 1.5 Hz, 1H, Har), 7.57 (ddd, J=7.7, 1.4, 1.4 Hz, 1H, Har), 7.29 (d, J=8.2 Hz, 2H, Har), 7.18 (ddd, J=7.6, 1.3, 1.3 Hz, 1H, Har), 7.12 (dd, J=7.7, 7.7 Hz, 1H, Har), 7.05 (s, 1H, Har), 3.68 (s, 2H, CH$_2$), 2.59 (t, J=5.6 Hz, 2H, CH$_2$), 2.53 (t, J=5.6 Hz, 2H, CH$_2$), 2.21 (s, 3H, CH$_3$), 0.90 (s, 21H, 3×(CH$_3$)$_2$CH). $^{13}$C NMR (101 MHz, CDCl$_3$) δ 165.6 (C), 158.8 (C), 149.1 (C), 143.4 (C), 134.5 (C), 131.3 (C), 131.2 (CH), 129.5 (CH), 128.7 (2×CH), 128.6 (CH), 128.1 (2×CH), 125.8 (CH), 123.8 (C), 108.5 (CH), 106.9 (C), 90.4 (C), 57.4 (2×CH$_2$), 52.6 (2×CH$_2$), 44.6 (CH$_2$), 44.2 (CH$_3$), 18.4 (3×(CH$_3$)$_2$CH), 11.2 (3×(CH$_3$)$_2$CH). HRMS [M+H]$^-$ C$_{32}$H$_{45}$N$_4$OSSi: Calcd. 561.3078 found 561.3063. Purity: 97.2%.

Example 45

4-((1H-tetrazol-1-yl)methyl)-N-(4-(3-((triisopropylsilyl)ethynyl)phenyl)thiazol-2-yl)benzamide

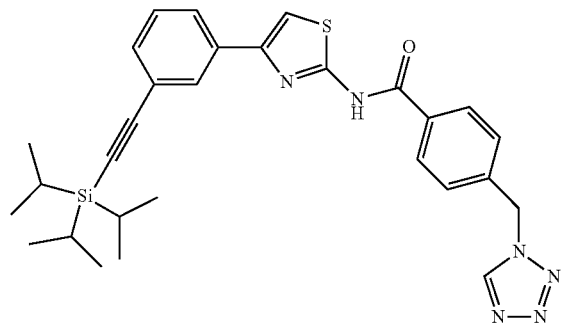 [SMILES: CC(C)[Si](C#Cc1cccc(-c2csc(NC(=O)c3ccc(Cn4cnnn4)cc3)n2)c1)(C(C)C)C(C)C]

According general procedure G using 4-((1H-tetrazol-1-yl)methyl)-N-(4-(3-bromophenyl)thiazol-2-yl)benzamide (91 mg, 0.206 mmol). Purification by silica gel flash chromatography (DCM/MeOH 9:1) afforded the product (9.6 mg, 7%) as a yellow viscous oil. $^1$H NMR (400 MHz, CDCl$_3$) δ 8.61 (s, 1H, NH), 7.87 (d, J=8.3 Hz, 2H, Har), 7.78 (dd, J=1.4, 1.4 Hz, 1H, Har), 7.60 (ddd, J=7.9, 1.5, 1.5 Hz, 1H, Har), 7.35 (ddd, J=7.6, 1.2, 1.2 Hz, 1H, Har), 7.26-7.20 (m, 4H, Har), 5.63 (s, 2H, CH$_2$), 1.13 (s, 21H, 3×(CH$_3$)$_2$CH). $^{13}$C NMR (101 MHz, CDCl$_3$) δ 164.6 (C), 159.4 (C), 149.5 (C), 142.9 (CH), 137.8 (C), 134.4 (C), 133.2 (C), 132.0 (CH), 129.8 (CH), 129.0 (CH), 128.9 (2×CH), 128.6 (2×CH), 126.2 (CH), 124.3 (C), 109.3 (CH), 106.9 (C), 91.6 (C), 51.7 (CH$_2$), 19.1 (3×(CH$_3$)$_2$CH), 11.6 (3×(CH$_3$)$_2$CH). HRMS [M+H]$^+$ C$_{29}$H$_{35}$N$_6$OSSi: Calcd. 543.2357 found 543.2341. Purity: 100.0%.

Example 46

4-((1H-imidazol-1-yl)methyl)-N-(4-(3-((triisopropylsilyl)ethynyl)phenyl)thiazol-2-yl)benzamide

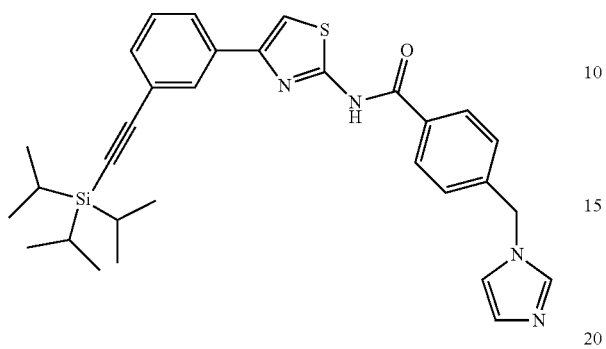

According general procedure G using 4-((1H-imidazol-1-yl)methyl)-N-(4-(3-bromophenyl)thiazol-2-yl)benzamide (57 mg, 0.13 mmol). Purification by silica gel flash chromatography (DCM/MeOH 9:1) afforded the product (29.5 mg, 42%) as a yellow viscous oil. $^1$H NMR (400 MHz, CDCl$_3$) δ 11.95 (bs, 1H, NH), 7.85 (d, J=8.3 Hz, 2H, Har), 7.81 (dd, J=1.5, 1.5 Hz, 1H, Har), 7.63 (ddd, J=7.8, 1.4, 1.4 Hz, 1H, Har), 7.59 (bs, 1H, Har), 7.34 (ddd, J=7.7, 1.3, 1.3 Hz, 1H, Har), 7.21 (dd, J=7.7, 7.7 Hz, 1H, Har), 7.21 (s, 1H, Har), 7.17 (bs, 1H, Har), 7.06 (d, J=8.2 Hz, 2H, Har), 6.91 (dd, J=1.2, 1.2 Hz, 1H, Har), 1.13 (s, 21H, 3×(CH$_3$)$_2$CH). $^{13}$C NMR (101 MHz, CDCl$_3$) δ 165.3 (C), 159.5 (C), 149.5 (C), 141.2 (C), 137.9 (CH), 134.6 (C), 132.5 (C), 131.8 (CH), 130.3 (CH), 129.7 (CH), 128.9 (CH), 128.8 (2×CH), 127.4 (2×CH), 126.2 (CH), 124.1 (C), 119.8 (CH), 109.0 (CH), 107.1 (C), 91.3 (C), 50.6 (CH$_2$), 19.0 (3×(CH$_3$)$_2$CH), 11.6 (3×(CH$_3$)$_2$CH). HRMS [M+H]$^+$ C$_{31}$H$_{37}$N$_4$OSSi: Calcd. 541.2440 found 541.2452. Purity: 97.3%.

Example 47 isopropyl 2-((4-((4-(3-((triisopropylsilyl)ethynyl)phenyl)thiazol-2-yl)carbamoyl)benzyl)amino)acetate

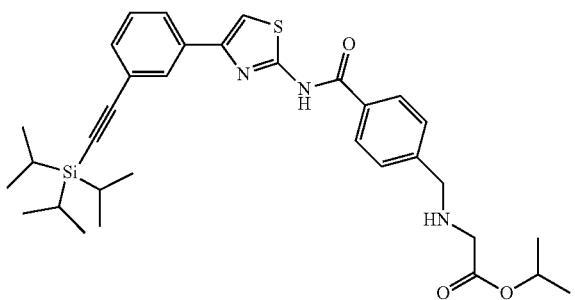 [SMILES: CC(C)OC(=O)CNCc1ccc(C(=O)Nc2nc(-c3cccc(C#C[Si](C(C)C)(C(C)C)C(C)C)c3)cs2)cc1]

According general procedure G using isopropyl 2-((4-((4-(3-bromophenyl)thiazol-2-yl)carbamoyl)benzyl)amino)acetate (28 mg, 0.058 mmol). Purification by silica gel flash chromatography (DCM/Acetone 9:1) afforded the product (7.7 mg, 23%) as a yellow viscous oil. $^1$H NMR (400 MHz, CDCl$_3$) δ 7.91 (d, J=8.2 Hz, 2H, Har), 7.91 (dd, J=1.9, 1.9 Hz, 1H, Har), 7.74 (ddd, J=7.8, 1.5, 1.5 Hz, 1H, Har), 7.53 (d, J=8.1 Hz, 2H, Har), 7.42 (ddd, J=7.7, 1.3, 1.3 Hz, 1H, Har), 7.33 (dd, J=7.7, 7.7 Hz, 1H, Har), 7.22 (s, 1H, Har), 3.99 (s, 2H, CH$_2$), 3.46 (s, 2H, CH$_2$), 1.27 (s, 3H, CH$_3$), 1.25 (s, 3H, CH$_3$), 1.16-1.12 (m, 21H, 3×(CH$_3$)$_2$CH). $^{13}$C NMR (101 MHz, CDCl$_3$) δ 184.2 (C), 164.3 (C), 158.2 (C), 149.3 (C), 134.3 (C), 131.6 (CH), 129.5 (CH), 129.3 (2×CH), 128.6 (CH), 127.8 (2×CH), 125.9 (CH), 124.0 (C), 108.7 (CH), 106.8 (C), 90.9 (C), 69.2 ((CH$_3$)$_2$CHO), 52.1 (CH$_2$), 49.3 (CH$_2$), 21.8 ((CH3)$_2$CHO), 18.7 (3×(CH$_3$)$_2$CH), 11.3 ((3×(CH$_3$)$_2$CH). HRMS [M+H]$^+$C$_{33}$H$_{44}$N$_3$O$_3$SSi: Calcd. 590.2848 found 590.2867.

Example 48

4-((4-methylpiperazin-1-yl)methyl)-N-(4-(3-((triisopropylsilyl)ethynyl)phenyl)thiazol-2-yl)benzamide

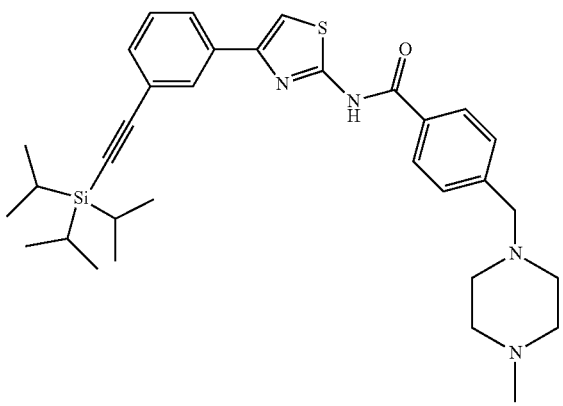 [SMILES: CC(C)[Si](C#Cc1cccc(-c2csc(NC(=O)c3ccc(CN4CCN(C)CC4)cc3)n2)c1)(C(C)C)C(C)C]

According general procedure G using N-(4-(3-bromophenyl)thiazol-2-yl)-4-((4-methylpiperazin-1-yl)methyl)benzamide (25 mg, 0.053 mmol). Purification by silica gel flash chromatography (DCM/MeOH 90:10) afforded the product (24.9 mg, 82%) as a yellow viscous oil. $^1$H NMR (300 MHz, CDCl$_3$) δ 10.35 (bs, 1H, NH), 7.88 (dd, J=1.5, 1.5 Hz, 1H, Har), 7.83 (d, J=8.2 Hz, 2H, Har), 7.70 (ddd, J=7.8, 1.4, 1.4 Hz, 1H, Har), 7.40 (d, J=8.2 Hz, 2H, Har), 7.37 (ddd, J=7.7, 1.3, 1.3 Hz, 1H, Har), 7.30 (dd, J=7.7, 7.7 Hz, 1H, Har), 7.22 (s, 1H, Har), 3.54 (s, 2H, CH$_2$), 2.48 (bs, 8H, 4×CH$_2$), 2.31 (s, 3H, CH$_3$), 1.14 (s, 21H, 3×(CH$_3$)$_2$CH). $^{13}$C NMR (75 MHz, CDCl$_3$) δ 165.0 (C), 158.9 (C), 149.6 (C), 144.3 (C), 134.6 (C), 131.9 (CH), 130.9 (C), 129.8 (CH), 129.7 (2×CH), 128.9 (CH), 127.7 (2×CH), 126.2 (CH), 124.3 (C), 109.0 (CH), 107.1 (C), 91.1 (C), 62.7 (CH$_2$), 55.3 (2×CH$_2$), 53.3 (2×CH$_2$), 46.2 (CH$_3$), 19.0 (3×(CH3)$_2$CH), 11.6 (3× (CH$_3$)$_2$CH). HRMS [M+H]$^+$ C$_{33}$H$_{45}$N$_4$OSSi: Calcd. 573.3078 found 573.3077. Purity: 100.0%.

Example 49

N-(4-(3-ethynylphenyl)thiazol-2-yl)-4-((4-methyl-piperazin-1-yl)methyl)benzamide

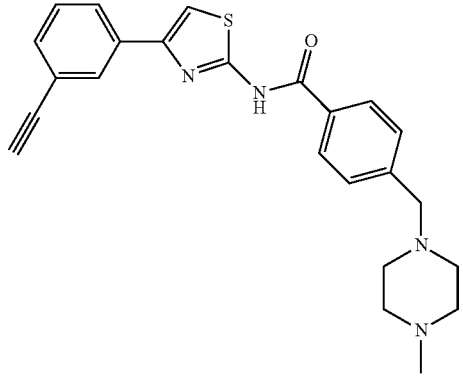 [SMILES: C#Cc1cccc(-c2csc(NC(=O)c3ccc(CN4CCN(C)CC4)cc3)n2)c1]

4((4-methylpiperazin-1-yl)methyl)-N-(4-(3-((triisopropylsilyl)ethynyl)phenyl)thiazol-2-yl)benzamide (Example 48, 14 mg, 0.025 mmol) was dissolved in dry THF (1 mL) and TBAF (73 µL, 2M in THF) was added. The solution was stirred overnight at room temperature. The mixture was evaporated under reduced pressure and purified by silica gel flash chromatography (DCM/MeOH 7:3) to afford the product as a yellow viscous oil (13.2 mg, quant.). $^1$H NMR (400 MHz, CDCl$_3$) δ 6.67 (dd, J=1.5, 1.5 Hz, 1H, Har), 6.62 (d, J=8.2 Hz, 2H, Har), 6.53 (ddd, J=7.8, 1.5, 1.5 Hz, 1H, Har), 6.21-6.14 (m, 3H, Har), 6.08 (dd, J=7.7, 7.7 Hz, 1H, Har), 5.96 (s, 1H, Har), 2.33 (s, 2H, CH$_2$), 1.86 (s, 1H, CH), 1.33 (bs, 8H, 4×CH$_2$), 1.15 (s, 3H, CH$_3$). $^{13}$C NMR (101 MHz, CDCl$_3$) δ 164.7 (C), 158.6 (C), 149.2 (C), 143.9 (C), 134.6 (C), 131.7 (CH), 130.8 (C), 129.9 (CH), 129.6 (2×CH), 128.9 (CH), 127.6 (2×CH), 126.5 (CH), 122.7 (C), 108.9 (CH), 83.5 (C), 77.6 (CH), 62.3 (CH$_2$), 54.9 (2×CH$_2$), 52.5 (2×CH$_2$), 45.6 (CH$_3$). HRMS [M+H]$^+$ C$_{24}$H$_{25}$N$_4$OS: Calcd. 417.1744 found 417.1735. Purity =95.5%

Example 50

4-((4-(prop-2-yn-1-yl)piperazin-1-yl)methyl)-N-(4-(3-((triisopropylsilyl)ethynyl)phenyl)thiazol-2-yl)benzamide

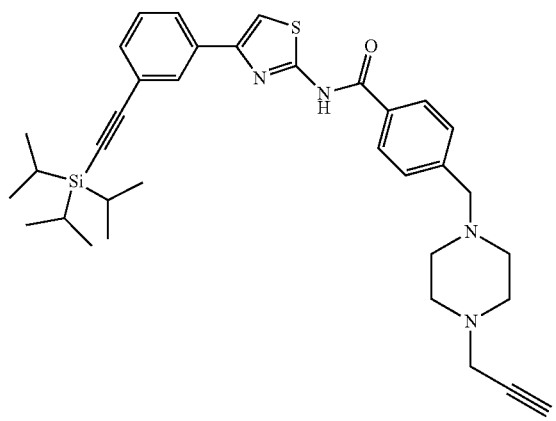 [SMILES: C#CCN1CCN(Cc2ccc(C(=O)Nc3nc(-c4cccc(C#C[Si](C(C)C)(C(C)C)C(C)C)c4)cs3)cc2)CC1]

1-(3-((triisopropylsilyl)ethynyl)phenyl)ethanone

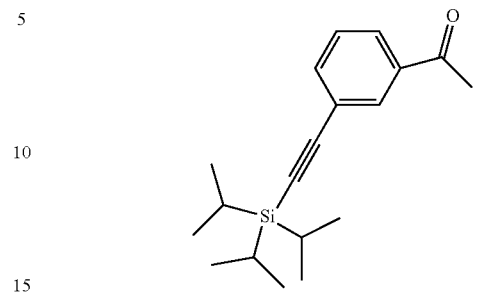

According the general procedure D using 1-(3-bromophenyl)ethanone (50 mg, 0.25 mmol). Purification by silica gel flash chromatography (PE/DCM 3:1) afforded the product (75 mg, quanti.) as a yellow viscous oil. $^1$H NMR (300 MHz, CDCl$_3$) δ 8.03 (dd, J=1.4, 1.4 Hz, 1H, Har), 7.89 (ddd, J=7.8, 1.5, 1.5 Hz, 1H, Har), 7.66 (ddd, J=7.7, 1.3, 1.3 Hz, 1H, Har), 7.41 (dd, J=7.7, 7.7 Hz, 1H, Har), 2.61 (s, 2H, CH$_2$), 1.14 (s, 21H, 3×(CH$_3$)$_2$CH). $^{13}$C NMR (75 MHz, CDCl$_3$) δ 197.78 (C), 137.44 (C), 136.73 (CH), 132.13 (CH), 128.88 (CH), 128.27 (CH), 124.51 (C), 92.37 (C), 91.50 (C), 27.01 (CH$_3$), 19.00 (3×(CH$_3$)$_2$CH), 11.62 (3×(CH$_3$)$_2$CH). HRMS [M+H]$^+$ C$_{19}$H$_{29}$OSi: Calcd. 301.1982 found 301.1970.

2-bromo-1-(3-((triisopropylsilyl)ethynyl)phenyl)ethanone

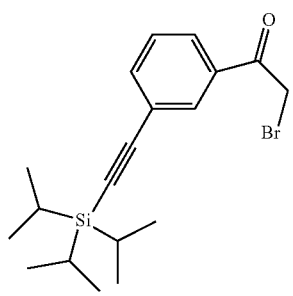 [SMILES: CC(C)[Si](C#Cc1cccc(C(=O)CBr)c1)(C(C)C)C(C)C]

To a solution of 1-(3-((triisopropylsilyl)ethynyl)phenyl)ethanone (184 mg, 0.61 mmol) in EA (900 µL) and CHCl$_3$ (900 µL) was added CuBr$_2$ (271 mg, 1.22 mmol). The solution was refluxed overnight. After cooling, the mixture was evaporated to dryness under vacuum. The resulting solid was dissolved in AE, filtered through a Celite pad and washed with AE. The organic layer was then washed with a saturated NaHCO$_3$ solution, dried over Na$_2$SO$_4$, filtered and evaporated under vacuum. The crude product (184 g, 85%) was used directly without further purification.

4-(3-((triisopropylsilyl)ethynyl)phenyl)thiazol-2-amine

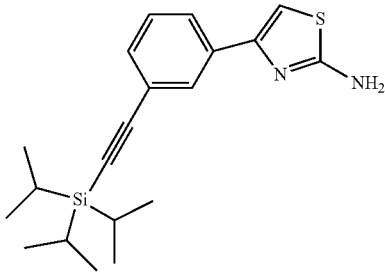 [SMILES: CC(C)[Si](C#Cc1cccc(-c2csc(N)n2)c1)(C(C)C)C(C)C]

To a stirred suspension of 2-bromo-1-(3-((triisopropylsilyl)ethynyl)phenyl)ethanone (184 mg, 0.48 mmol) in EtOH (5 mL) was added thiourea (37 mg, 0.484 mmol) and the mixture was heated at 70° C. overnight. After cooling to room temperature, the solvent was evaporated to dryness. The resulting solid was stirred in a mixture of EtOAc/saturated aqueous NaHCO$_3$ solution (2:1) until dissolution, and then extracted with EtOAc. The organic layer was dried over Na$_2$SO4, filtrated and the solvent was removed under reduced pressure. Purification by silica gel flash chromatography (DCM/MeOH 99:1) afforded the product (128 mg, 75%) as a yellow viscous oil. $^1$H NMR (300 MHz, CDCl$_3$) δ 7.87 (dd, J=1.4, 1.4 Hz, 1H, Har), 7.69 (ddd, J=7.8, 1.4, 1.4 Hz, 1H, Har), 7.41 (ddd, J=7.6, 1.3, 1.3 Hz, 1H, Har), 7.31 (dd, J=7.7, 7.7 Hz, 1H, Har), 6.72 (s, 1H, Har), 5.56 (bs, 2H, NH$_2$), 1.15 (s, 21H, 3×(CH$_3$)$_2$CH). $^{13}$C NMR (75 MHz, CDCl$_3$) δ 168.14 (C), 150.54 (C), 134.98 (C), 131.58 (CH), 129.81 (CH), 128.81 (CH), 126.20 (CH), 124.15 (C), 107.26 (C), 103.49 (CH), 90.89 (C), 19.00 (3×(CH$_3$)$_2$CH), 11.63 (3×(CH$_3$)$_2$CH). HRMS [M+H]$^+$ C$_{20}$H$_{29}$N$_2$SSi: Calcd. 357.1815 found 357.1814.

4-((4-(prop-2-yn-1-yl)piperazin-1-yl)methyl)-N-(4-(3-((triisopropylsilyl)ethynyl)phenyl)thiazol-2-yl)benzamide

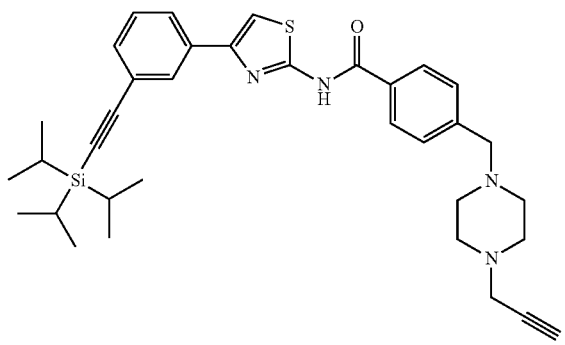 [SMILES: C#CCN1CCN(Cc2ccc(C(=O)Nc3nc(-c4cccc(C#C[Si](C(C)C)(C(C)C)C(C)C)c4)cs3)cc2)CC1]

4-(3-((triisopropylsilyl)ethynyl)phenyl)thiazol-2-amine (128 mg, 0.36 mmol) was diluted with toluene (1 mL) in a two necked round bottom flask equipped with a reflux condenser under an argon atmosphere. The solution was cooled down at 0° C. and trimethylaluminium in toluene (176 µL, 2M) was slowly added. After 15 minutes, the ester (65 mg, 0.24 mmol) in toluene (300 µL) was added. The resulting solution was heated under reflux for two days, cooled to room temperature and slowly hydrolyzed with water to prevent foam formation. The aqueous layer was extracted four times with DCM, and the organic layers were combined and dried over Na$_2$SO$_4$. The solvent was evaporated under reduced pressure. Purification by silica gel flash chromatography (DCM/MeOH 9:1) afforded the product as a yellow viscous oil (120 mg, 84%). $^1$H NMR (300 MHz, CDCl$_3$) δ 11.08 (bs, 1H, NH), 7.79 (bs, 1H, Har), 7.73 (d, J=8.0 Hz, 2H, Har), 7.66-7.60 (m, 1H, Har), 7.31-7.22 (m, 4H, Har), 7.21 (s, 1H, Har), 3.48 (s, 2H, CH$_2$), 3.30 (d, J=2.1 Hz, 2H, CH$_2$), 2.59 (bs, 4H, 2×CH$_2$), 2.46 (bs, 4H, 2×CH$_2$), 2.25 (s, J=2.1 Hz, 1H, CH), 1.13 (s, 21H, 3×(CH$_3$)$_2$CH). $^{13}$C NMR (75 MHz, CDCl$_3$) δ 165.5 (C), 159.4 (C), 149.4 (C), 143.9 (C), 134.4 (C), 131.7 (CH), 131.0 (C), 129.7 (CH), 129.4 (2×CH), 128.8 (CH), 127.8 (2×CH), 126.1 (CH), 124.1 (C), 108.9 (CH), 107.0 (C), 91.1 (C), 79.0 (C), 73.6 (CH), 62.6 (CH$_2$), 53.2 (2×CH$_2$), 52.1 (2×CH$_2$), 47.0 (CH$_3$), 19.0 (3×(CH3)$_2$CH), 11.6 (3×(CH$_3$)$_3$CH). HRMS [M+H]$^+$ C$_{35}$H$_{45}$N$_4$OSSi: Calcd. 597.3078 found 597.3065.

Intermediates and Precursors

When not commercially available or readily obtainable by the skilled man in the art, the intermediates and precurors to the compounds of this invention were synthesised as follows:

tert-Butyl 1-piperazinecarboxylate

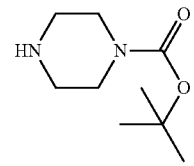

A solution of di-tert-butyl dicarbonate (6.32 g, 29 mmol) in MeOH (62 mL) was slowly added to a stirring solution of piperazine (5 g, 58 mmol) in MeOH (62 mL) at 0° C. The mixture was then stirred for 18 h at room temperature, and the solvent removed in vacuum. The crude solid was redissolved in diethyl ether with warming, and the white precipitate left was filtered off. The product was extracted from the mother liquor with 1M citric acid solution, and the aqueous layer was washed with Et$_2$OAc, basified with Na$_2$CO$_3$ (pH 11), and extracted with Et$_2$OAc. The organic layer was dried over Na$_2$SO$_4$ and evaporated in vacuum to give tert-butyl 1-piperazinecarboxylate as a waxy white solid (crude, 4 g, 37%). $^1$H NMR (300 MHz, CDCl$_3$) δ 1.46 (s, 9H, 3×CH$_3$), δ 2.11 (s, 1H, NH), δ 2.83 (t, 4H, J=5.1Hz, 2×CH$_2$), δ 3.41 (t, 4H, J=5.1 Hz, 2×CH$_2$). $^{13}$C NMR (75 MHz, CDCl$_3$) δ 155.1 (C), δ 79.8 (C), δ 46.2 (4×CH$_2$), δ 28.7 (3×CH$_3$). MS (ESI) [M+H]$^+$ 187. mp=53-54° C.

tert-Butyl 4-propargylpiperazine-1-carboxylate

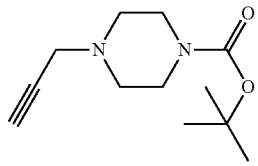 [SMILES: C#CCN1CCN(C(=O)OC(C)(C)C)CC1]

A solution of tert-butyl 1-piperazinecarboxylate (4 g, 21.5 mmol) and diisopropylethylamine (5.8 mL, 22.6 mmol) in CHCl₃ (180 mL) was stirred at 0° C. during 15 min. Propargyl bromide (2.3 mL, 21.5 mmol) was slowly added to the solution. The mixture was stirred for 24 h at room temperature. CHCl₃ (50 mL) was then added and the solution obtained was washed with saturated NaHCO3 solution, brine, and then dried over Na₂SO₄. The solution was filtered and evaporated to dryness to give tert-butyl 4-propargylpiperazine-1-carboxylate (3.25 g, 68%). ¹H RMN (300 MHz, CDCl₃) δ 3.46 (t, 4H, J=5.1 Hz, 2×CH₂), δ 3.29 (t, 2H, J=2.4 Hz, CH₂), 2.50 (t, 4H, J=5.1Hz, 2×CH₂), 2.25 (t, 1H, J=2.4 Hz, CH), 1.45 (s, 9H, 3×CH₃). ¹³C RMN (75 MHz, CDCl₃) δ 155.0 (C), 80.0 (C), 78.7 (C), 73.8 (CH), 51.9 (CH₂), 47.3 (2×CH₂), 46.2 (2×CH₂), 28.7 (3×CH₃). MS (ESI) [M+H]⁺ 225. mp =53-54° C.

N-Propargylpiperazine

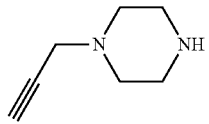

tert-Butyl 4-propargylpiperazine-1-carboxylate (300 mg, 1.34 mmol) was dissolved in a mixture of trifluoroacetic acid (0.9 mL) and DCM (4 mL). The solution was stirred at room temperature overnight, and then was evaporated to dryness in vacuum. The residue was dissolved in water and then based with Na2CO3 (pH11), and extracted with EtOAc. The organic layer was dried over Na₂SO₄, filtered and evaporated to dryness to give N-propargylpiperazine as yellow oil. (73 mg, 44%). ¹H RMN (300 MHz, CDCl₃) δ 3.27 (d, 2H, J=2.5 Hz, CH₂), δ 2.92 (t, 4H, J=5.1 Hz, 2×CH₂), δ 2.53 (t, 4H, J=5.1 Hz, 2×CH₂), δ 2.23 (t, 1H, J=2.5 Hz, CH). ¹³C RMN (75 MHz, CDCl₃) δ 78.9 (C8), 73.6 (C9), 53.1 (CH₂), 47.7 (2×CH₂), 46.0 (2×CH₂). HRMS [M+H]⁺ C₇H₁₂N₂: Calcd. 125.1073 found 125.1072.

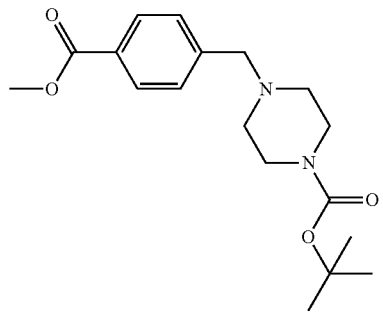 [SMILES: COC(=O)c1ccc(CN2CCN(C(=O)OC(C)(C)C)CC2)cc1]

tert-butyl 4-(4-(methoxycarbonyl)benzyl)piperazine-1-carboxylate

To a solution of methyl 4-(bromomethyl)benzoate (1.55 g, 6.77 mmol), K2CO3 (1.77 g, 12.8 mmol) in CH3CN at 0° C. was added the tert-butyl 1-piperazinecarboxylate (1.4 g, 7.53 mmol). The mixture was stirred 16 h at room temperature. The mixture was filtered through Celite pad and evaporated to dryness to give the product as a yellow oil. (2.4 g, 95%). ¹H RMN (300 MHz, CDCl₃) δ 7.97 (d, J=8.3 Hz, 2H, Har), 7.38 (d, J=8.3 Hz, 2H, Har), 3.89 (s, 3H, CH₃), 3.40 (t, 4H, J=5.1 Hz, 2×CH₂), 2.37 (t, 4H, 2×CH₂), 1.43 (s, 9H, 3×CH₃). ¹³C RMN (75 MHz, CDCl₃) δ 167.3 (C), 155.1 (C), 143.8 (C), 129.9 (2×CH), 129.4 (C), 129.2 (2×CH), 79.9 (C), 62.9 (CH₂), 53.2 (4×CH₂), 52.3 (CH₃), 28.7 (3×CH₃). HRMS [M+H]⁺ C₁₈H₂₇N₂O₄: Calcd. 335.1970 found 335.1965.

Methyl 4-(piperazin-1-ylmethyl)benzoate

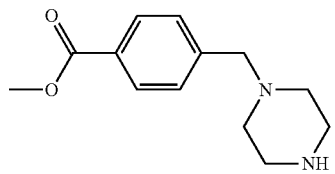 [SMILES: COC(=O)c1ccc(CN2CCNCC2)cc1]

tert-butyl 4-(4-(methoxycarbonyl)benzyl)piperazine-1-carboxylate (1.5 g, 4.49 mmol) was dissolved in a mixture of trifluoroacetic acid (4.0 mL) and DCM (13.5 mL). The solution was stirred at room temperature overnight, and then was evaporated to dryness in vacuum to give the product as colourless oil. (1.0 g, quant.).¹H RMN (300 MHz, CDCl₃) δ 7.95 (d, J=8.3 Hz, 2H, Har), 7.37 (d, J=8.3 Hz, 2H, Har), 3.87 (s, 3H, CH₃), 3.50 (s,2H, CH₂), 2.86 (t, J=5.0 Hz, 4H, 2×CH₂), 2.38 (t, J=5.0 Hz, 4H, 2×CH₂), 1.89 (s, 1H, NH). ¹³C RMN (75 MHz, CDCl₃) δ 167.3 (C), 144.0 (2×C), 129.8 (2×CH), 129.2 (2×CH), 63.5 (CH₂), 54.7 (2×CH₂), 52.3 (CH₃), 46.3 (2×CH₂).

Methyl 4-((4-(prop-2-yn-1-yl)piperazin-1-yl)methyl)benzoate

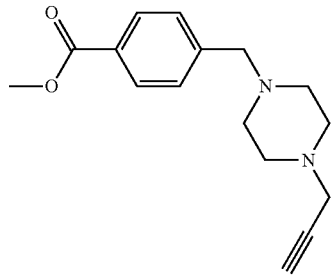 [SMILES: C#CCN1CCN(Cc2ccc(C(=O)OC)cc2)CC1]

To a solution of methyl 4-(piperazin-1-ylmethyl)benzoate (1.0 g, 4.49 mmol), K₂CO₃ (7.25 g, 52.53 mmol) in CH₃CN (38 mL) at 0° C. was added the propargyl bromide (1.4 g, 7.53 mmol). The mixture was stirred 16 h at room temperature. The mixture was filtered trough Celite pad and evaporated to dryness in vacuum. The residue was diluted in DCM and a saturated citric acid solution. The aqueous layer was extracted with DCM, then based with Na₂CO₃ (pH8-9), and extracted with DCM. The organic layer was dried over Na₂SO₄, filtered and evaporated to dryness to give the product. Purification by silica gel flash chromatography (EtOAc/MeOH 9:1) afforded the product (524 mg, 43%) as a yellow viscous oil. ¹H NMR (300 MHz, CDCl3) δ 7.97 (d, J=8.2 Hz, 2H, Har), 7.40 (d, J=8.1 Hz, 2H, Har), 3.89 (s, 3H, CH₃), 3.55 (s, 2H, CH₂), 3.29 (d, J=2.3 Hz, 2H, CH₂), 2.60 (bs, 4H, 2×CH₂), 2.51 (bs, 4H, 2×CH₂), 2.25 (t, J=2.3 Hz, 1H, CH). ¹³C RMN (75 MHz, CDCl₃) δ 167.3 (C), 149.4

(C), 144.0 (C), 129.8 (2×CH), 129.2 (2×CH), 79.1 (C), 73.5 (CH$_2$), 62.8 (CH$_2$), 53.2 (2×CH$_2$), 52.3 (CH$_3$), 52.1 (2×CH$_2$), 46.7 (CH$_2$). HRMS [M+H]$^+$ C$_{16}$H$_{21}$N$_2$O$_2$: Calcd. 273.1598 found 273.1605.

Methyl 5-bromofuran-2-carboxylate

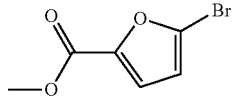

A solution of 5-bromo-2-furoic acid (1.00 g, 5.2 mmol) in dichloromethane (50 mL) was treated at 0° C. with oxalyl chloride (674 µL, 7.8 mmol) and a catalytic amount of N,N-dimethylformamide (125 µL). After 25 minutes, MeOH (2 mL) was added to the solution and stirred at ambient temperature for one night. The solvent and excess of oxalyl chloride were removed under reduced pressure and the solid was dissolved in EtOAc. The organic layer was washed with a 1M NaOH solution, dried over Na$_2$SO$_4$, filtered and evaporated to dryness to give a white solid (890 mg, 83%). $^1$H NMR (300 MHz, CDCl$_3$) δ 7.12 (d, J=3.6 Hz, 1H, Har), 6.45 (d, J=3.6 Hz, 1H, Har), 3.88 (s, 3H, CH$_3$). $^{13}$C RMN (75 MHz, CDCl$_3$) δ 158.4 (C), 146.5 (C), 127.8 (C), 120.4 (CH), 114.3 (CH), 52.4 (CH$_3$). MS [M+H]$^+$ C$_6$H$_5$BrO$_3$: Calcd. 203.9422 found 203.9414.

4-(5-(methoxycarbonyl)furan-2-yl)benzoic acid

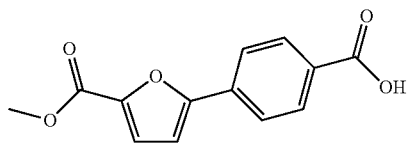 [SMILES: COC(=O)c1ccc(-c2ccc(C(=O)O)cc2)o1]

To a solution of halide (933 mg, 4.5 mmol) in 1,4-dioxane (55 mL) was added Pd(PPh$_3$)$_4$ (264 mg, 0.22 mmol). The mixture was stirred at room temperature for 15 min, and 4-carboxyphenylboronic acid (793 mg, 4.78 mmol), dissolved in water (37 mL), and K$_2$CO$_3$ (1.25 g) were introduced. The mixture was stirred at 100° C. for 16 h. The reaction was filtered through a Celite pad, and the solvent was removed under vacuum. The residue was diluted in EtOAc and washed with water. The aqueous layer was acidified to pH 6 and extracted with EtOAc. The organic layer was dried over Na$_2$SO$_4$, filtered, and concentrated to dryness to afford the product (464 mg, 41%) as a white solid. $^1$H NMR (300 MHz, MeOD) δ 8.13 (d, J=8.9 Hz, 2H, Har), 7.94 (d, J=8.9 Hz, 2H, Har), 7.37 (d, J=3.6 Hz, 1H, Har), 7.13 (d, J=3.8 Hz, 1H, Har), 3.95 (s, 3H, CH$_3$). $^{13}$C RMN (75 MHz, CDCl$_3$) δ 158.4 (C-6), 146.5 (C-1), 127.8 (C-4), 120.4 (C-2), 114.3 (C-3), 52.4 (C-10). HRMS [M+Na$^+$] C$_{13}$H$_{11}$O$_5$: Calcd. 247.0601 found 247.0607.

Methyl 5-(4-(4-methylpiperazine-1-carbonyl)phenyl)furan-2-carboxylate

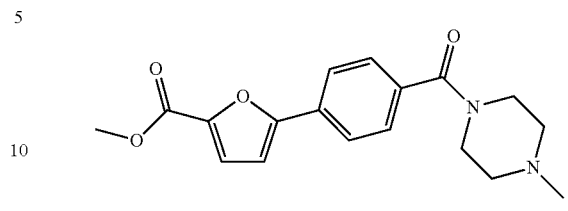

A solution of the carboxylic acid (150 mg, 0.65 mmol), DCC (402 mg, 1.3 mmol) and HOBt (176 mg, 1.3 mmol) in DMF (940 µL it) was stirred at room temperature during fifteen minutes. The 1-methyl piperazine (80 µL it, 0.71 mmol) and NEt$_3$ (94 µL) was added to the solution and the resulting mixture was stirred at room temperature during 20 hours. The precipitate was filtered off and the filtrate was diluted with EtOAc. The organic layer was extracted with a 0.1M HCl solution. The aqueous layer was washed with EtOAc and based with a saturated Na$_2$CO$_3$ solution (pH 10). The mixture was extracted with Et$_2$O, and the combined organic layer was dried over Na$_2$SO$_4$, filtered and evaporated under vacuum. Purification by silica gel flash chromatography (DCM/MeOH 9:1) afforded the product (144 mg, 68%) as a yellow viscous oil. $^1$H NMR (300 MHz, CDCl$_3$) δ 7.82 (d, J=8.5 Hz, 2H, Har), 7.47 (d, J=8.3 Hz, 2H, Har), 7.25 (d, J=3.8 Hz, 1H, Har), 6.79 (d, J=3.8 Hz, 1H, Har), 3.92 (s, 3H, CH$_3$), 3.81 (bs, 4H, 2×CH$_2$), 2.49 (bs, 4H, 2×CH$_2$), 2.33 (s, 3H, CH$_3$). $^{13}$C NMR (75 MHz, CDCl3) δ 170.6 (C16), 156.8 (C6), 144.4 (C), 136.2 (C), 130.0 (C), 128.8 (CH), 128.1 (CH), 127.4 (CH), 125.1 (CH), 120.3 (CH), 108.1 (CH), 52.3 (CH$_3$), 46.4 (CH$_2$), 42.5 (CH$_3$). HRMS [M+H]$^+$ C$_{18}$H$_{21}$N$_2$O$_4$: Calcd. 329.1496 found 329.1497.

Methyl 5-(4-(4-(prop-2-yn-1-yl)piperazine-1-carbonyl)phenyl)furan-2-carboxylate

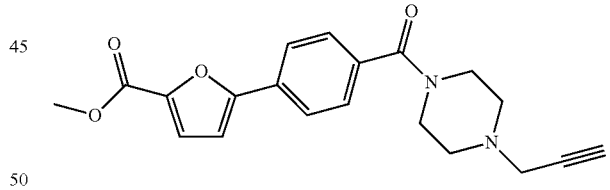

A solution of the carboxylic acid (130 mg, 0.46 mmol), DCC (285 mg, 1.38 mmol) and HOBt (124 mg, 0.92 mmol) in DMF (660 µL) was stirred at room temperature during fifteen minutes. The 1-propargyl piperazine (63 mg, 0.51 mmol) and DIPEA (1.19 mL, 4.6 mmol) was added to the solution and the resulting mixture was stirred at 80° C. overnight. The mixture was evaporated under vacuum. The resulting solid was dissolved with EtOAc and filtered through a Celite pad. The filtrate was washed with a saturated Na2CO3 solution. The combined organic layer was dried over Na2SO4, filtered and evaporated under vacuum. Purification by silica gel flash chromatography (DCM/MeOH 9:1) afforded the product (115 mg, 75%) as a yellow viscous oil. 1H NMR (300 MHz, CDCl3) δ 7.97 (d, J=8.2 Hz, 2H, Har), 7.40 (d, J=8.1 Hz, 2H, Har), 3.89 (s, 3H, CH$_3$), 3.29 (d, J=2.3 Hz, 2H, CH$_2$), 2.60 (bs, 4H, 2×CH$_2$), 2.51 (bs, 4H, 2×CH$_2$), 2.25 (t, J=2.3 Hz, 1H, CH). $^{13}$C NMR (101 MHz, CDCl$_3$) δ 170.0 (C), 159.4 (C), 156.8 (C), 144.4 (C), 136.1 (C), 131.1 (C), 128.1 (2×CH), 125.2 (2×CH), 120.3 (CH), 108.2 (CH), 77.6 (C), 74.3 (CH), 52.3 (CH$_3$), 52.1 (2×CH$_2$), 49.1 (2×CH$_2$), 47.14 (CH$_2$). HRMS [M+H]$^+$ C$_{20}$H$_{21}$N$_2$O$_4$: Calcd. 353.1496 found 353.1507.

Methyl 4-((4-methylpiperazin-1-yl)methyl)benzoate

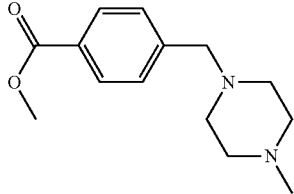 [SMILES: COC(=O)c1ccc(CN2CCN(C)CC2)cc1]

To a solution of methyl 4-(bromomethyl)benzoate (5 g, 21.8 mmol), K$_2$CO$_3$ (5.1 g, 37.1 mmol) in CH$_3$CN at 0° C. was added the 1-methylpiperazine (2.66 mL, 24 mmol). The mixture was stirred 7 hours at room temperature. The mixture was filtered through Celite pad, washed with EtOAc and evaporated to dryness to give the product as a yellow oil. (5.02 g, 93%). $^1$ NMR (300 MHz, CDCl$_3$) δ 7.98 (d, J=8.3 Hz, 2H, Har), 7.39 (d, J=8.4 Hz, 2H, Har), 3.90 (s, 3H, CH$_3$), 3.55 (s, 2H, CH$_2$), 2.47 (bs, 8H, 4×CH$_2$), 2.29 (s, 3H, CH$_3$). $^{13}$C NMR (75 MHz, CDCl$_3$) δ 167.4 (C), 151.5 (C), 144.2 (C), 130.0 (2×CH), 129.3 (2×CH), 63.0 (CH$_2$), 55.5 (2×CH$_2$), 53.5 (2×CH$_2$), 52.4 (CH$_3$), 46.4 (CH$_3$). HRMS [M+H]$^+$ C$_{14}$H$_{21}$N$_2$O$_2$: Calcd. 249.1598 found 249.1598.

4-bromo-3-methylacetophenonone

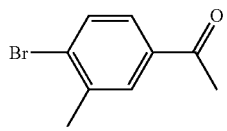

4-bromo-3-methylbenzonitrile (1g, 5.1 mmol) was dissolved in toluene (4 mL) under argon atmosphere. Methyl magnesium bromide (1.3 mL, 11.22 mmol) was added to the solution. The mixture was heated at 60-65° C. overnight. The reaction mixture was hydrolyzed with a 5M H$_2$SO$_4$ solution during 1h30. The aqueous layer was extracted with EtOAc (5×100 mL). The combined organic layer was washed with 25 mL of water, dried over Na$_2$SO$_4$, filtered and evaporated under vacuum. Purification by silica gel flash chromatography (PE/EtOAc 5:1) afforded the product (630 mg, 58%) as a white oil. $^1$H NMR (300 MHz, CDCl3) δ 7.80 (bs, 1H, Har), 7.61 (bs, 2H, Har), 2.56 (s, 3H, CH$_3$), 2.44 (s, 3H, CH$_3$). $^{13}$C NMR (75 MHz, CDCl$_3$) δ 197.7 (C), 138.7 (C), 136.4 (C), 133.0 (CH), 131.0 (CH), 130.7 (CH), 127.4 (CH), 26.9 (CH$_3$), 23.3 (CH$_3$). HRMS (ESI) [M+Na]$^+$ C$_9$H$_9$BrONa: Calcd. 234.9729 found 234.9737.

2-bromo-1-(4-bromo-3-methylphenyl)ethanone

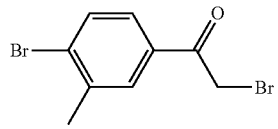

In a two necked round bottom flask equipped with a reflux condenser under an argon atmosphere was added CuBr$_2$ (700 mg, 3.14 mmol) and EtOAc (8 mL). The suspension was stirred during 20 minutes. The 4-bromo-3-methylacetophenonone (335 mg, 1.57 mmol) pre-dissolved in EtOAc (8 mL) was added to the mixture and heated at 80° C. during one hour. A new equivalent of CuBr$_2$ (330 mg, 1.57 mmol) was added and the reaction was stirred at 80° C. overnight. The suspension was cooled down, filtered through a Celite pad and washed with EtOAc. The filtrate was washed with a saturated NaHCO$_3$ solution. The organic layer was dried over Na$_2$SO$_4$, filtered and evaporated under vacuum. Purification by silica gel flash chromatography (PE/EtOAc 6:1) afforded the product (273 mg, 60%) as a white oil. $^1$H NMR (300 MHz, CDCl$_3$) δ 7.85-7.80 (m, 1H, Har), 7.68-7.58 (m, 2H, Har), 4.40 (s, 2H, CH$_2$), 2.46 (s, 3H, CH$_3$). $^{13}$C NMR (75 MHz, CDCl$_3$) δ 191.0 (C), 139.3 (C), 133.3 (CH), 133.2 (C), 132.0 (C), 131.2 (CH), 127.9 (CH), 30.9 (CH$_2$), 23.3 (CH$_3$). HRMS (ESI) [M+H]$^+$ C$_9$H$_9$Br$_2$O: Calcd. 312.8834 found 312.8838.

4-(4-bromo-3-methylphenyl)thiazol-2-amine

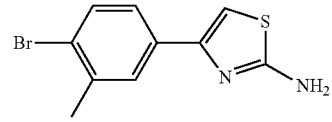

To a stirred suspension of 2-bromo-1-(4-bromo-3-methylphenyl)ethanone (273 mg, 0.935 mmol) in EtOH (5 mL) was added thiourea (78 mg, 1 mmol) and the mixture was heated at 70° C. overnight. After cooling to room temperature, the solvent was evaporated to dryness. The resulting solid was stirred in a mixture of EtOAc/saturated aqueous NaHCO$_3$ solution (2:1) until dissolution, and then extracted with EtOAc. The organic layer was dried over Na$_2$SO4, filtrated and the solvent was removed under reduced pressure. The product was crystallized in PE and filtered to afford a yellow oil (140 mg, 56%). $^1$H NMR (300 MHz, CDCl$_3$) δ 7.64 (d, J=1.8 Hz, 1H, Har), 7.51 (d, J=8.3 Hz, 1H, Har), 7.41 (dd, J=8.3, 2.0 Hz, 1H, Har), 6.69 (s, 1H, Har), 5.24 (s, 2H, NH$_2$), 2.42 (s, 3H, CH$_3$). $^{13}$C NMR (75 MHz, CDCl$_3$) δ 167.8 (C), 150.6 (C), 138.3 (C), 134.1 (C), 132.8 (CH), 128.6 (CH), 125.1 (CH), 124.4 (C), 103.4 (CH), 23.3 (CH$_3$). HRMS (ESI) [M+H]$^+$ C$_{10}$H$_{10}$BrN$_2$S: Calcd 268.9743 found 268.9749.

2-bromo-1-(3-bromophenyl)ethanone

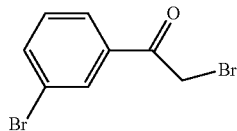

In a two necked round bottom flask equipped with a reflux condenser under an argon atmosphere was added CuBr$_2$ (2.24 mg, 10 mmol) and EtOAc (24 mL). The suspension was stirred during 20 minutes. The 4-bromo-3-methylacetophenonone (1 g, 5.02 mmol) pre-dissolved in EtOAc (24 mL) was added to the mixture and heated at 80° C. during one hour. A new equivalent of CuBr$_2$ (1.07 g, 5 mmol) was added and the reaction was stirred at 80° C. overnight. The suspension was cooled down, filtered through a Celite pad and washed with EtOAc. The filtrate was washed with a saturated NaHCO$_3$ solution. The organic layer was dried over Na$_2$SO$_4$, filtered and evaporated under vacuum. Purification by silica gel flash chromatography (PE/DCM 3:2) afforded the product (795 mg, 57%) as a white oil. $^1$H NMR (300 MHz, CDCl$_3$) δ 8.09 (dd, J=1.8, 1.8 Hz, 1H, Har), 7.88 (ddd, J=7.8, 1.5, 1.1 Hz, 1H, Har), 7.71 (ddd, J=8.0, 1.9, 1.0 Hz, 1H, Har), 7.36 (dd, J=7.9, 7.9 Hz, 1H, Har), 4.41 (s, 2H, CH$_2$). $^{13}$C NMR (75 MHz, CDCl$_3$) δ 190.3 (C), 137.1 (CH), 135.9 (C), 132.1 (CH), 130.7 (CH), 127.7 (CH), 123.5 (C), 30.8 (CH$_2$). HRMS (ESI) [M+H]$^+$ C$_8$H$_7$Br$_2$O: Calcd. 276.8860 found 276.8858.

4-(3-bromophenyl)thiazol-2-amine

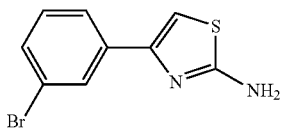

To a stirred suspension of 2-bromo-1-(3-bromophenyl) ethanone (2.13 g, 7.72 mmol) in EtOH (40 mL) was added thiourea (595 mg, 7.8 mmol) and the mixture was heated at 70° C. overnight. After cooling to room temperature, the solvent was evaporated to dryness. The resulting solid was stirred in a mixture of EtOAc/saturated aqueous NaHCO$_3$ solution (2:1) until dissolution, and then extracted with EtOAc. The organic layer was dried over Na$_2$SO4, filtrated and the solvent was removed under reduced pressure. The product was crystallized in PE and filtered to afford a yellow solid (1.6 g, 82%). $^1$H NMR (300 MHz, MeOD) δ 7.97 (dd, J=1.7, 1.7 Hz, 1H, Har), 7.74 (ddd, J=7.9, 1.5, 1.1 Hz, 1H, Har), 7.44 (ddd, J=7.9, 1.9, 1.0 Hz, 1H, Har), 7.29 (dd, J=7.9, 7.9 Hz, 1H, Har), 6.93 (s, 1H, Har). $^{13}$C NMR (75 MHz, MeOD) δ 166.5 (C), 150.9 (C), 139.2 (C), 132.2 (CH), 132.2 (CH), 130.7 (CH), 126.4 (CH), 124.5 (C), 105.0 (CH). HRMS (ESI) [M+H]$^+$ C$_9$H$_8$BrN$_2$S: Calcd. 254.9586 found 254.9590. mp =127.2-127.8° C.

4-bromo-3-chloro-N-methoxy-N-methylbenzamide

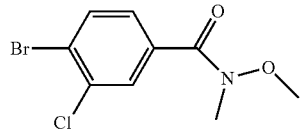

To a solution of 4-bromo-3-chlorobenzoic acid (2 g, 8.53 mmol) in DMF (20 mL) was added EDCI.HCl (3.99 g, 25.6 mmol), HOBt (2.3 g, 17.1 mmol) and the DIPEA (2.65 mL, 10.23 mmol) at 0° C. After five minutes of stirring, the Weinreb amine (1 g, 10.23 mmol) was added to the solution and the solution was heated at 50° C. overnight. The mixture was partitioned between EtOAc (200 mL) and water (50 mL). The organic layer was washed with 1M NaOH solution (60 mL), 2M HCl solution (60 mL) and brine (60 mL). The organic layer was dried over Na$_2$SO$_4$, filtered and evaporated under vacuum to afford the product (2.36 g, 94%) as a yellow viscous oil. $^1$H NMR (300 MHz, CDCl$_3$) δ 7.77 (d, J=1.8 Hz, 1H, Har), 7.62 (d, J=8.3 Hz, 1H, Har), 7.43 (dd, J=8.3, 1.8 Hz, 1H, Har), 3.51 (s, 3H, CH$_3$), 3.32 (s, 3H, CH$_3$). $^{13}$C NMR (75 MHz, CDCl$_3$) δ 167.6 (C), 134.6 (C), 134.5 (C), 133.6 (CH), 130.5 (CH), 128.0 (CH), 125.4 (C), 61.6 (OCH$_3$), 33.7 (CH$_3$). HRMS (ESI) [M+H]$^+$ C$_9$H$_{10}$BrClNO$_2$: Calcd. 277.9578 found 277.9578.

4-bromo-3-chlorobenzophenone

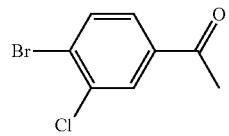

The 4-bromo-N-methoxy-N,3-dimethylbenzamide (108 mg, 0.368 mmol) was dissolved with THF (1 mL) at 0° C. under an argon atmosphere. Methylmagnesium bromide (270 μL, 0.81 mmol) was added dropwise and the solution was stirred at room temperature overnight. The mixture was quenched with a saturated NH$_4$Cl solution (30 mL) and then Et$_2$O was added. The aqueous layer was extracted with Et$_2$O (3×30 mL). The combined organic layer was washed with brine (30 mL), dried over Na$_2$SO$_4$, filtered and evaporated under vacuum to afford the product (66 mg, 77%) as a yellow solid. $^1$H NMR (300 MHz, CDCl3) δ 8.01 (d, J=2.1 Hz, 1H, Har), 7.73 (d, J=8.3 Hz, 1H, Har), 7.67 (dd, J=8.4, 2.0 Hz, 1H, Har), 2.58 (s, 3H, CH$_3$). $^{13}$C NMR (75 MHz, CDCl3) δ 196.2 (C), 137.6 (C), 134.4 (CH), 130.4 (CH), 128.5 (C), 128.0 (CH), 126.5 (C), 26.9 (CH$_3$). HRMS (ESI) [M+H]$^+$ C$_8$H$_7$BrClO: Calcd. 232.9363 found 232.9366. mp=87.5-89.2° C.

2-bromo-1-(4-bromo-3-chlorophenyl)ethanone

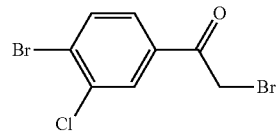

In a two necked round bottom flask equipped with a reflux condenser under an argon atmosphere was added CuBr$_2$ (955 mg, 4.18 mmol) and EtOAc (10 mL). The suspension was stirred during 20 minutes. The 4-bromo-3-methylacetophenonone (500 mg, 2.14 mmol) pre-dissolved in EtOAc (10 mL) was added to the mixture and heated at 80° C. during one hour. A new equivalent of CuBr$_2$ (460 mg, 2.06 mmol) was added and the reaction was stirred at 80° C. overnight. The suspension was cooled down, filtered through a Celite pad and washed with EtOAc. The filtrate was washed with a saturated NaHCO$_3$ solution. The organic layer was dried over Na$_2$SO$_4$, filtered and evaporated under vacuum. Purification by silica gel flash chromatography (PE/EtOAc 4:1) afforded the product (582 mg, 87%) as a yellow viscous oil. $^1$H NMR (300 MHz, CDCl3) δ 8.06 (d, J=2.1 Hz, 1H, Har), 7.77 (d, J=8.5 Hz, 1H, Har), 7.71 (dd, J=8.4, 2.0 Hz, 1H, Har), 4.38 (s, 2H, CH$_2$). $^{13}$C NMR (75 MHz, CDCl$_3$) δ 134.7 (CH), 131.0 (CH), 128.3 (CH), 30.4 (CH$_2$). HRMS (ESI) [M+H]$^+$ C$_8$H$_6$Br$_2$ClO: Calcd. 310.8468 found 310.8455.

4-(4-bromo-3-chlorophenyl)thiazol-2-amine

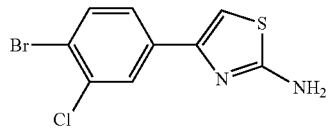 [SMILES: Nc1nc(-c2ccc(Br)c(Cl)c2)cs1]

To a stirred suspension of 2-bromo-1-(4-bromo-3-chlorophenyl)ethanone (273 mg, 0.935 mmol) in EtOH (5 mL) was added thiourea (78 mg, 1 mmol) and the mixture was heated at 70° C. overnight. After cooling to room temperature, the solvent was evaporated to dryness. The resulting solid was stirred in a mixture of EtOAc/saturated aqueous NaHCO$_3$ solution (2:1) until dissolution, and then extracted with EtOAc. The organic layer was dried over Na$_2$SO4, filtrated and the solvent was removed under reduced pressure. The product was crystallized in PE and filtered to afford a yellow solid (140 mg, 56%). $^1$H NMR (300 MHz, CDCl$_3$) δ 7.88 (d, J=1.9 Hz, 1H, Har), 7.60 (d, J=8.4 Hz, 1H, Har), 7.50 (dd, J=8.4, 1.9 Hz, 1H, Har), 6.76 (s, 1H, Har), 5.13 (s, 2H, NH$_2$). $^{13}$C NMR (75 MHz, CDCl$_3$) δ 168.3 (C), 149.1 (C), 135.5 (C), 135.0 (C), 134.1 (CH), 128.0 (CH), 125.5 (CH), 121.6 (C), 104.4 (CH). HRMS (ESI) [M+H]$^+$ C$_9$H$_7$BrClN$_2$S: Calcd 288.9196 found 288.9191. mp =142.5-143.0° C.

2-bromo-1-(3-bromo-4-methylphenyl)ethanone

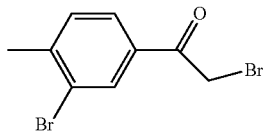

In a two necked round bottom flask equipped with a reflux condenser under an argon atmosphere was added CuBr$_2$ (2.1 g, 9.4 mmol) and EtOAc (22 mL). The suspension was stirred during 20 minutes. The 3-bromo-4-methylacetphenonone (1 g, 4.69 mmol) pre-dissolved in EtOAc (22 mL) was added to the mixture and heated at 80° C. during one hour. A new equivalent of CuBr$_2$ (1.0 g, 4.7 mmol) was added and the reaction was stirred at 80° C. overnight. The suspension was cooled down, filtered through a Celite pad and washed with EtOAc. The filtrate was washed with a saturated NaHCO$_3$ solution. The organic layer was dried over Na$_2$SO$_4$, filtered and evaporated under vacuum. Purification by silica gel flash chromatography (PE/DCM 4:1) afforded the product (1.075 g, 86%) as a white oil. $^1$H NMR (300 MHz, CDCl$_3$) δ 8.12 (d, J=1.7 Hz, 1H, Har), 7.79 (dd, J=7.9, 1.9 Hz, 1H, Har), 7.33 (d, J=7.9 Hz, 1H, Har), 4.39 (s, 2H, CH$_2$), 2.45 (s, 3H, CH$_3$). $^{13}$C NMR (75 MHz, CDCl$_3$) δ 190.0 (C), 145.0 (C), 133.5 (C), 133.1 (CH), 131.4 (CH), 128.0 (CH), 125.8 (C), 30.9 (CH$_2$), 23.6 (CH$_3$). HRMS [M+Na]$^+$ C$_9$H$_8$Br$_2$NaO: Calcd. 312.8834 found 312.8835.

4-(3-bromo-4-methylphenyl)thiazol-2-amine

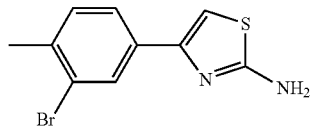

To a stirred suspension of 2-bromo-1-(3-bromo-4-methylphenyl)ethanone (1.075 g, 3.99 mmol) in EtOH (21 mL) was added thiourea (343 mg, 4.03 mmol) and the mixture was heated at 70° C. overnight. After cooling to room temperature, the solvent was evaporated to dryness. The resulting solid was stirred in a mixture of EtOAc/saturated aqueous NaHCO$_3$ solution (2:1) until dissolution, and then extracted with EtOAc. The organic layer was dried over Na$_2$SO4, filtrated and the solvent was removed under reduced pressure. The product was crystallized in PE and filtered to afford a yellow solid (828 mg, 77%). $^1$H NMR (300 MHz, MeOD) δ 7.90 (d, J=1.7 Hz, 1H, Har), 7.53 (dd, J=7.9, 1.7 Hz, 1H, Har), 7.18 (d, J=7.9 Hz, 1H, Har), 6.72 (s, 1H, Har), 2.32 (s, 3H, CH$_3$). $^{13}$C NMR (75 MHz, MeOD) δ 172.0 (C), 150.7 (C), 138.7 (C), 136.5 (C), 132.7 (CH), 131.4 (CH), 126.6 (CH), 104.1 (CH), 23.55 (CH$_3$). HRMS [M+Na]$^+$C$_{10}$H$_{10}$BrN$_2$S: Calcd. 268.9746 found 268.9743.

2-bromo-1-(5-bromothiophen-2-yl)ethanone

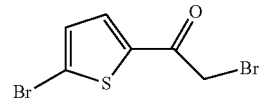

To a solution of 1-(5-bromothiophen-2-yl)ethanone (1.41 g, 6.91 mmol) in AE (10 mL) and CHCl$_3$ (10 mL) was added CuBr$_2$ (3.1 g, 13.82 mmol). The solution was refluxed overnight. After cooling, the mixture was evaporated to dryness under vacuum. The resulting solid was dissolved in AE, filtered through a Celite pad and washed with AE. The organic layer was then washed with a saturated NaHCO$_3$ solution, dried over Na$_2$SO$_4$, filtered and evaporated under vacuum. Purification by silica gel flash chromatography (EP/DCM 2:3) afforded the product (1.72 g, 88%) as a yellow viscous oil. $^1$H NMR (300 MHz, CDCl$_3$) δ 7.54 (d, J=4.1 Hz, 1H, Har), 7.13 (d, J=4.1 Hz, 1H, Har), 4.28 (s, 2H, CH$_2$). $^{13}$C NMR (75 MHz, CDCl$_3$) δ 183.71 (C), 142.4 (C), 134.1 (CH), 131.8 (CH), 124.8 (C), 30.0 (CH$_2$). HRMS [M+H]$^+$ C$_6$H$_4$Br$_2$NaOS: Calcd. 304.8242 found 304.8242.

4-(5-bromothiophen-2-yl)thiazol-2-amine

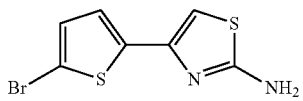

To a stirred suspension of 2-bromo-1-(5-bromothiophen-2-yl)ethanone (1.65 g, 5.81 mmol) in EtOH (30 mL) was added thiourea (454 mg, 5.87 mmol) and the mixture was heated at 70° C. overnight. After cooling to room temperature, the solvent was evaporated to dryness. The resulting solid was stirred in a mixture of EtOAc/saturated aqueous NaHCO3 solution (2:1) until dissolution, and then extracted with EtOAc. The organic layer was dried over Na$_2$SO4, filtrated and the solvent was removed under reduced pressure. Purification by silica gel flash chromatography (DCM/MeOH 95:15) afforded the product (1.38 g, 91%) as a yellow solid. $^1$H NMR (300 MHz, MeOD) δ 7.09 (d, J=3.9 Hz, 1H, Har), 6.99 (d, J=3.9 Hz, 1H, Har), 6.67 (s, 1H, Har). $^{13}$C NMR (75 MHz, MeOD) δ 171.2 (C), 145.0 (C), 141.8 (C), 131.7 (CH), 124.4 (CH), 111.8 (C), 101.9 (CH). HRMS [M+H]$^+$ C$_7$H$_6$BrN$_2$S: Calcd. 260.9150 found 260.9156.

N-(4-(4-bromo-3-methylphenyl)thiazol-2-yl)-4-((4-methylpiperazin-1-yl)methyl)benzamide

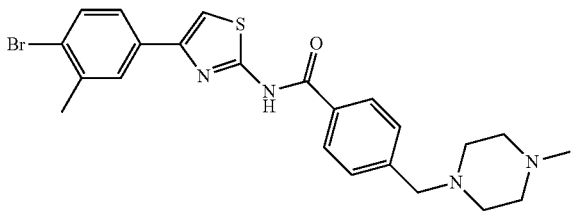 [SMILES: Cc1cc(-c2csc(NC(=O)c3ccc(CN4CCN(C)CC4)cc3)n2)ccc1Br]

4-(4-bromo-3-methylphenyl)thiazol-2-amine (273 mg, 0.94 mmol) was diluted with toluene (1.5 mL) in a two necked round bottom flask equipped with a reflux condenser under an argon atmosphere. The solution was stirred and trimethylaluminium in heptane (443 µL, 2M) was slowly added. The solution was heated at 50° C. during 20 min and the ester 2 (170 mg, 0.62 mmol) in toluene (500 µL) was added. The resulting solution was heated under reflux for one night, cooled to room temperature and slowly hydrolyzed with water to prevent foam formation. The aqueous layer was based with a 1M NaOH solution (pH9-10). The mixture was extracted three times with DCM, and the organic layers were combined and dried over Na$_2$SO$_4$. The solvent was evaporated under reduced pressure. Purification by silica gel flash chromatography (DCM/MeOH 8:2) afforded the product (178 mg, 59%) as a yellow solid. $^1$H NMR (300 MHz, CDCl$_3$ δ 10.49 (bs, 1H, Har), 7.82 (d, J=8.3 Hz, 2H, Har), 7.61 (d, J=1.5 Hz, 1H, Har), 7.47 (d, J=8.3 Hz, 1H, Har), 7.40 (dd, J=8.1, 2.0 Hz, 1H, Har), 7.38 (d, J=8.3 Hz, 2H, Har), 7.16 (s, 1H, Har), 3.53 (s, 2H, CH$_2$), 2.48 (bs, 8H, 4×CH$_2$), 2.38 (s, 3H, CH$_3$), 2.31 (s, 3H, CH$_3$). $^{13}$C NMR (75 MHz, CDCl$_3$) δ 165.1 (C), 159.1 (C),149.5 (C), 144.3 (C), 138.4 (C), 133.7 (C), 132.9 (CH), 130.9 (C), 129.6 (2×CH), 128.6 (CH), 127.7 (2×CH), 125.2 (CH), 124.8 (C), 108.7 (CH), 62.7 (CH$_2$), 55.4 (2×CH$_2$), 53.3 (2×CH$_2$), 46.2 (CH$_3$), 23.3 (CH$_3$). HRMS (ESI) [M+H]$^+$ C$_{23}$H$_{26}$BrN$_4$OS: Calcd. 485.1005 found 485.1009. mp=181.4-182.4° C.

N-(4-(3-bromophenyl)thiazol-2-yl)-4-((4-methylpiperazin-1-yl)methyl)benzamide

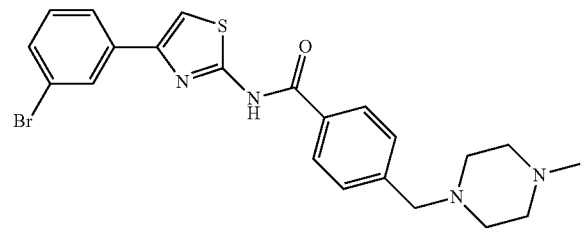 [SMILES: CN1CCN(Cc2ccc(C(=O)Nc3nc(-c4cccc(Br)c4)cs3)cc2)CC1]

4-(4-bromophenyl)thiazol-2-amine (195 mg, 0.76 mmol) was diluted with toluene (2.5 mL) in a two necked round bottom flask equipped with a reflux condenser under an argon atmosphere. The solution was stirred and trimethylaluminium in heptane (360 µL, 2M) was slowly added. The solution was heated at 50° C. during 20 min and the ester 2 (126 mg, 0.51 mmol) in toluene (500 µL) was added. The resulting solution was heated under reflux for one night, cooled to room temperature and slowly hydrolyzed with water to prevent foam formation. The aqueous layer was based with a 1M NaOH solution (pH9-10). The mixture was extracted three times with DCM, and the organic layers were combined and dried over Na$_2$SO$_4$. The solvent was evaporated under reduced pressure. Purification by silica gel flash chromatography (DCM/MeOH 85:15) afforded the product (206 mg, 86%) as a yellow viscous oil. $^1$H NMR (300 MHz, CDCl3) δ 8.00 (dd, J=1.7, 1.7 Hz, 1H, Har), 7.90 (d, J=8.3 Hz, 2H, Har), 7.73 (ddd, J=7.8, 2.6, 1.1 Hz, 1H, Har), 7.49 (d, J=8.3 Hz, 2H, Har), 7.44 (ddd, J=7.9, 1.9, 1.0 Hz, 1H, Har), 7.27 (dd, J=7.9, 7.9 Hz, 1H, Har), 7.21 (s, 1H, Har), 3.59 (s, 2H, CH$_2$), 2.55 (bs, 8H, 4×CH$_2$), 2.35 (s, 3H, CH$_3$). $^{13}$C NMR (75 MHz, CDCl3) δ 165.33 (C), 159.4 (C), 148.7 (C), 144.2 (C), 136.5 (C), 131.1 (CH), 130.9 (C), 130.4 (CH), 129.6 (CH), 129.4 (C), 127.8 (C), 124.8 (CH), 123.1 (C), 109.3 (CH), 62.7 (CH$_2$), 55.3 (2×CH$_2$), 53.3 (2×CH$_2$), 46.2 (CH$_3$). HRMS (ESI) [M+H]$^+$ C$_{22}$H$_{24}$BrN$_4$OS: Calcd. 471.0844 found 471.0849.

N-(4-(4-bromo-3-chlorophenyl)thiazol-2-yl)-4-((4-methylpiperazin-1-yl)methyl)benzamide

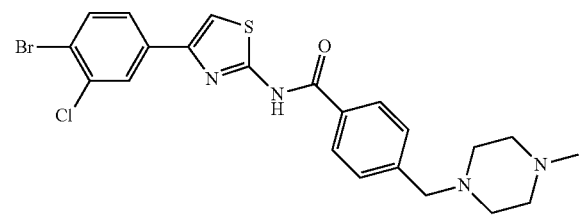 [SMILES: CN1CCN(Cc2ccc(C(=O)Nc3nc(-c4ccc(Br)c(Cl)c4)cs3)cc2)CC1]

4-(4-bromo-3-chlorophenyl)thiazol-2-amine (200 mg, 0.69 mmol) was diluted with toluene (2 mL) in a two necked round bottom flask equipped with a reflux condenser under an argon atmosphere. The solution was stirred and trimethylaluminium in heptane (327 µL, 2M) was slowly added. The solution was heated at 50° C. during 20 min and the ester 2 (114 mg, 0.46 mmol) in toluene (700 µL) was added. The resulting solution was heated under reflux for one night, cooled to room temperature and slowly hydrolyzed with water to prevent foam formation. The aqueous layer was based with a 1M NaOH solution (pH9-10). The mixture was extracted three times with DCM, and the organic layers were combined and dried over $Na_2SO_4$. The solvent was evaporated under reduced pressure. Purification by silica gel flash chromatography (DCM/MeOH 85:15) afforded the product (224.3 mg, 64%) as a yellow viscous oil. $^1$H NMR (300 MHz, $CDCl_3$) δ 10.32 (bs, 1H, NH), 7.95 (d, J=2.0 Hz, 1H, Har), 7.91 (d, J=8.3 Hz, 2H, Har), 7.55 (d, J=8.3 Hz, 1H, Har), 7.47 (dd, J=8.4, 2.0 Hz, 1H, Har), 7.40 (d, J=8.2 Hz, 2H, Har), 7.21 (s, 1H, Har), 3.54 (s, 2H, $CH_2$), 2.50 (bs, 8H, 4×$CH_2$), 2.33 (s, 3H, $CH_3$). $^{13}$C NMR (75 MHz, $CDCl_3$) δ 165.1 (C), 159.2 (C), 148.1 (C), 144.5 C), 135.2 (C), 135.1 (C), 134.1 (CH), 130.8 (C), 129.6 (2×CH), 128.1 (CH), 127.8 (2×CH), 125.6 (CH), 122.0 (C), 109.7 (CH), 62.7 ($CH_2$), 55.3 (2×$CH_2$), 53.2 (2×$CH_2$), 46.2 ($CH_3$). HRMS (ESI) [M+H]$^+$ $C_{22}H_{23}BrClN_4OS$: Calcd. 505.0459 found 505.0452.

N-(4-(3-bromo-4-methylphenyl)thiazol-2-yl)-4-((4-methylpiperazin-1-yl)methyl)benzamide

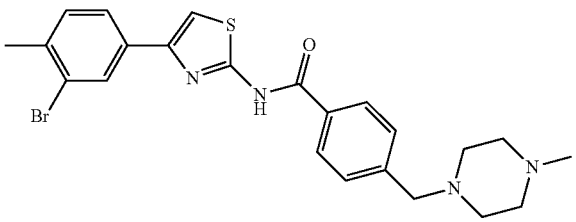

4-(3-bromo-4-methylphenyl)thiazol-2-amine (118 mg, 0.44 mmol) was diluted with toluene (1 mL) in a two necked round bottom flask equipped with a reflux condenser under an argon atmosphere. The solution was stirred and trimethylaluminium in heptane (210 µL, 2M) was slowly added. The solution was heated at 50° C. during 20 min and the ester 2 (73 mg, 0.29 mmol) in toluene (700 µL) was added. The resulting solution was heated under reflux for one night, cooled to room temperature and slowly hydrolyzed with water to prevent foam formation. The aqueous layer was based with a 1M NaOH solution (pH9-10). The mixture was extracted three times with DCM, and the organic layers were combined and dried over $Na_2SO_4$. The solvent was evaporated under reduced pressure. Purification by silica gel flash chromatography (DCM/MeOH 85:15) afforded the product (127 mg, 60%) as a yellow viscous oil. $^1$H NMR (400 MHz, CDCl3) δ 7.98 (d, J=1.6 Hz, 1H, Har), 7.86 (d, J=8.3 Hz, 2H, Har), 7.61 (dd, J=7.9, 1.6 Hz, 1H, Har), 7.45 (d, J=8.2 Hz, 2H, Har), 7.22 (d, J=8.0 Hz, 1H, Har), 7.15 (s, 1H, Har), 3.56 (d, J=5.2 Hz, 2H, $CH_2$), 2.51 (bs, 8H, 4×$CH_2$), 2.40 (s, 3H, $CH_3$), 2.33 (s, 3H, $CH_3$). $^{13}$C NMR (101 MHz, CDCl3) δ 164.8 (C), 158.7 (C), 148.9 (C), 144.4 (C), 137.8 (C), 134.1 (C), 131.3 (CH), 130.9 (C), 130.2 (CH), 129.8 (CH), 127.7 (CH), 125.6 (C), 125.1 (CH), 108.6 (CH), 62.72 ($CH_2$), 55.34 (2×$CH_2$), 53.25 (2×$CH_2$), 46.19 ($CH_3$), 23.02 ($CH_3$). HRMS [M+H]$^+$ $C_{23}H_{26}BrN_4OS$: Calcd. 485.1005 found 485.1004.

N-(4-(5-bromothiophen-2-yl)thiazol-2-yl)-4-((4-methylpiperazin-1-yl)methyl)benzamide

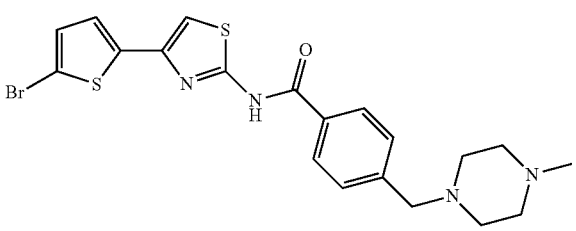 [SMILES: CN1CCN(Cc2ccc(C(=O)Nc3nc(-c4ccc(Br)s4)cs3)cc2)CC1]

4-(5-bromothiophen-2-yl)thiazol-2-amine (1 g, 3.82 mmol) was diluted with toluene (7 mL) in a two necked round bottom flask equipped with a reflux condenser under an argon atmosphere. The solution was stirred and trimethylaluminium in heptane (1.8 mL, 2M) was slowly added. The solution was heated at 50° C. during 20 min and the ester 2 (630 mg, 2.54 mmol) in toluene (1 mL) was added. The resulting solution was heated under reflux for one night, cooled to room temperature and slowly hydrolyzed with water to prevent foam formation. The aqueous layer was based with a 1M NaOH solution (pH 9-10). The mixture was extracted three times with DCM, and the organic layers were combined and dried over $Na_2SO_4$. The solvent was evaporated under reduced pressure. Purification by silica gel flash chromatography (DCM/MeOH 8:2) afforded the product (1.09 g, 91%) as a brown solid. $^1$H NMR (300 MHz, $CDCl_3$) δ 7.75 (d, J=8.2 Hz, 2H, Har), 7.33 (d, J=8.2 Hz, 2H, Har), 6.98 (s, 1H, Har), 6.97 (d, J=3.9 Hz, 1H, Har), 6.84 (d, J=3.9 Hz, 1H, Har), 3.47 (s, 2H, $CH_2$), 2.41 (bs, 8H, 4×$CH_2$), 2.27 (s, 3H, $CH_3$). $^{13}$C NMR (75 MHz, $CDCl_3$) δ 165.6 (Cq), 159.3 (Cq), 144.2 (Cq), 143.9 (Cq), 139.9 (Cq), 131.0 (Cq), 130.7 (CH), 129.5 (2×CH), 127.8 (2×CH), 124.0 (CH), 112.1 (Cq), 107.3 (CH), 62.6 ($CH_2$), 55.3 (2×$CH_2$), 53.3 (2×$CH_2$), 46.2 ($CH_3$). HRMS [M+H]$^-$ $C_{20}H_{22}BrN_4OS_2$: Calcd. 477.0413 found 477.0412.

N-(4-(4-bromo-3-methylphenyl)thiazol-2-$_3$71)-4-((4-(prop-2-yn-1-yl)piperazin-1-yl)methyl)benzamide

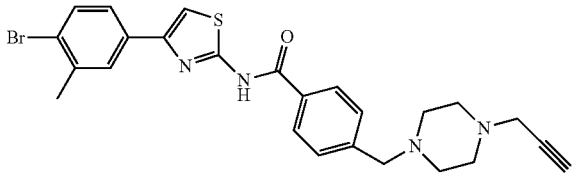 [SMILES: C#CCN1CCN(Cc2ccc(C(=O)Nc3nc(-c4ccc(Br)c(C)c4)cs3)cc2)CC1]

4-(4-bromo-3-methylphenyl)thiazol-2-amine (80 mg, 0.3 mmol) was diluted with DCM (2.5 mL) in a two necked round bottom flask equipped with a reflux condenser under an argon atmosphere. The solution was cooled down at 0° C. and trimethylaluminium in heptane (172 µL it, 2M) was slowly added. After 15 minutes, the ester (73 mg, 0.27 mmol) in DCM (1 mL) was added. The resulting solution was heated under reflux for two days, cooled to room temperature and slowly hydrolyzed with water to prevent foam formation. The aqueous layer was extracted four times with DCM, and the organic layers were combined and dried over $Na_2SO_4$. The solvent was evaporated under reduced pressure. Purification by silica gel flash chromatography (DCM/MeOH 9:1) afforded the product which was crystallized in PE to afford a yellow viscous oil (41 mg, 29%). $^1$H NMR (300 MHz, CDCl3) δ 10.49 (s, 1H, NH), 7.81 (d, J=8.2 Hz, 2H, Har), 7.60 (d, J=1.4 Hz, 1H, Har), 7.46 (d, J=8.2 Hz, 1H, Har), 7.42-7.37 (m, 3H, Har), 7.17 (s, 1H, Har), 3.56 (s, 2H, CH$_2$), 3.32 (d, J=2.3 Hz, 2H, CH$_2$), 2.64 (bd, 4H, 2×CH$_2$), 2.53 (bs, 4H, 2×CH$_2$), 2.37 (s, 3H, CH$_3$), 2.27 (t, J=2.3 Hz, 1H, CH). $^{13}$C NMR (75 MHz, CDCl3) δ 165.0 (C), 159.1 (C), 151.7 (C), 149.5 (C), 138.4 (C), 133.7 (C), 132.8 (CH), 131.8 (C), 129.7 (2×CH), 128.6 (CH), 127.8 (2×CH), 125.2 (CH), 124.8 (C), 108.7 (CH), 77.6 (C), 73.8 (CH$_2$), 62.6 (CH$_2$), 53.2 (2×CH$_2$), 52.0 (2×CH$_2$), 47.1 (CH$_2$), 23.3 (CH$_3$). Purity: 90.4%.

tert-butyldiphenyl(prop-2-yn-1-yloxy)silane

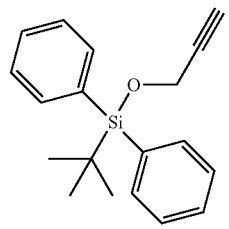 [SMILES: C#CCO[Si](c1ccccc1)(c1ccccc1)C(C)(C)C]

To a solution of 2-propynol (105 µL, 1.78 mmol) in CH$_2$Cl$_2$ (700 µL) was added tert-butyldiphenylsilyl chloride (490 µL, 1.87 mmol) and imidazole (242 mg, 3.56 mmol). After 16 h stirring, the reaction mixture was washed with water, dried over Na$_2$SO$_4$, and was concentrated in vacuo to afford a colourless oil (520 mg, quant.). $^1$H NMR (300 MHz, CDCl$_3$) δ 7.76-7.69 (m, 5H, Har), 7.42 (m, 5H, Har), 4.32 (d, J=2.4 Hz, 2H, CH$_2$), 2.39 (t, J=2.4 Hz, 1H, CH), 1.08 (s, 9H, (CH$_3$)$_3$). $^{13}$C NMR (75 MHz, CDCl$_3$) δ 135.9 (4×CH), 135.1 (C), 133.3 (C), 130.2 (2×CH), 128.1 (4×CH), 82.3 (C), 73.4 (CH), 52.8 (CH$_2$), 27.0 ((CH$_3$)$_3$CSi), 19.5 ((CH$_3$)$_3$CSi).

triisopropyl(prop-2-yn-1-yloxy)silane.

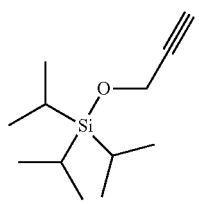

To a solution of 2-propynol (105 µL, 1.78 mmol) in CH$_2$Cl$_2$ (700 µL) was added tert-butyldiphenylsilyl chloride (396 µL, 1.87 mmol) and imidazole (242 mg, 3.56 mmol). After 16 h stirring, the reaction mixture was washed with water, dried over Na$_2$SO$_4$, and was concentrated in vacuo to afford a colourless oil (378 mg, quant.). $^1$H NMR (300 MHz, CDCl$_3$) δ 4.38 (d, J=2.4 Hz, 2H, CH$_2$), 2.39 (t, J=2.4 Hz, 1H, CH), 1.08 (d, J=4.6 Hz, 21H, (3×(CH$_3$)$_2$CH). $^{13}$C NMR (75 MHz, CDCl$_3$) δ 82.8 (C), 72.9 (CH), 52.1 (CH$_2$), 18.2 (3×(CH$_3$)$_2$CH), 12.3 (3×(CH$_3$)$_2$CH).

tert-butyl(ethynyl)diphenylsilane

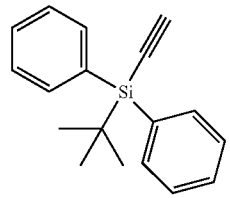 [SMILES: C#C[Si](c1ccccc1)(c1ccccc1)C(C)(C)C]

To a cooled (−78° C.) solution of lithium acetylide (ethylene diamine complex) (250 mg, 92 mmol) in dry THF (12 mL) was added dropwise tert-butyldiphenylsilyl chloride (590 µL it, 2.26 mmol). After 1 h, the reaction was stirred at 0° C. for 2 h and stirred overnight at room temperature. The reaction mixture was then quenched with saturated NH$_4$Cl and extracted with Et$_2$O. The combined organic layers were dried over Na$_2$SO$_4$, filtered and evaporated under vacuo to afford the product (594 mg, 99%). $^1$H NMR (300 MHz, CDCl$_3$) δ 7.87-7.80 (m, 4H, Har), 7.48-7.36 (m, 6H, Har), 2.73 (s, 1H, CH), 1.14 (s, 9H, (CH$_3$)$_3$). $^{13}$C NMR (75 MHz, CDCl$_3$) δ 135.7 (4×CH), 129.8 (2×C), 127.9 (6×CH), 97.4 (C), 85.5 (C), 27.1 ((CH$_3$)$_3$CSi), 18.5 ((CH$_3$)$_3$CSi).

tert-butyldimethyl(prop-2-yn-1-yloxy)silane

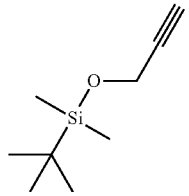

To a solution of 2-propynol (105 µL, 1.78 mmol) in CH$_2$Cl$_2$ (700 µL) was added tert-butyldiphenylsilyl chloride (282 mg, 1.87 mmol) and imidazole (242 mg, 3.56 mmol). After 16 h stirring, the reaction mixture was washed with water, dried over Na$_2$SO$_4$, and was concentrated in vacuo to afford a colourless oil (302 mg, quant.). $^1$H NMR (300 MHz, CDCl$_3$) δ 4.31 (d, J=2.4 Hz, 2H, CH$_2$), 2.39 (t, J=2.4 Hz, 1H, CH), 0.91 (s, 9H, (CH$_3$)$_3$), 0.12 (s, 6H, (CH$_3$)$_2$). $^{13}$C NMR (75 MHz, CDCl$_3$) δ 82.7 (C), 73.2 (CH), 51.9 (CH$_2$), 26.1 ((CH3)$_3$CSi), 18.6 ((CH$_3$)$_3$CSi),-4.9 (2×CH$_3$Si).

N-(4-(3-bromophenyl)thiazol-2-yl)-5-(4-(4-methylpiperazine-1-carbonyl)phenyl)furan-2-carboxamide

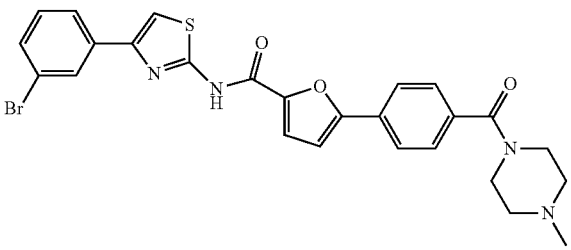 [SMILES: CN1CCN(C(=O)c2ccc(-c3ccc(C(=O)Nc4nc(-c5cccc(Br)c5)cs4)o3)cc2)CC1]

4-(3-bromophenyl)thiazol-2-amine (524 mg, 2.05 mmol) was diluted with toluene (2 mL) in a two necked round bottom flask equipped with a reflux condenser under an argon atmosphere. The solution was stirred and trimethylaluminium in toluene (1.03 mL, 2M) was slowly added. The solution was heated at 50° C. during 20 min and the ester (450 mg, 1.37 mmol) in toluene (1 mL) was added. The resulting solution was heated under reflux for one night, cooled to room temperature and slowly hydrolyzed with water to prevent foam formation. The aqueous layer was based with a 1M NaOH solution (pH9-10). The mixture was extracted three times with DCM, and the organic layers were combined and dried over $Na_2SO_4$. The solvent was evaporated under reduced pressure. Purification by silica gel flash chromatography (DCM/MeOH 9:1) afforded the product (354 mg, 47%) as a brown viscous oil. $^1$H NMR (300 MHz, $CDCl_3$) δ 11.38 (s, 1H, NH), 7.69 (dd, J=1.7, 1.7 Hz, 1H, Har), 7.53 (d, J=8.4 Hz, 2H, Har), 7.49 (ddd, J=7.9, 2.4, 1.2 Hz, 1H, Har), 7.44-7.40 (m, J=8.4 Hz, 2H, Har), 7.35 (d, J=3.7 Hz, 1H, Har), 7.34-7.29 (m, 1H, Har), 7.11 (dd, J=7.9, 7.9 Hz, 1H, Har), 7.07 (s, 1H, Har), 6.71 (d, J=3.7 Hz, 1H, Har), 3.82 (bs, 2H, $CH_2$), 3.48 (bs, 2H, $CH_2$), 2.45 (bs, 4H, 2×$CH_2$), 2.33 (s, 3H, $CH_3$). $^{13}$C NMR (75 MHz, $CDCl_3$) δ 169.8 (C), 158.6 (C), 156.1 (C), 155.9 (C), 150.0 (C), 149.1 (C), 145.5 (C), 136.3 (C), 131.1 (CH), 130.5 (Cq), 130.3 (CH), 129.4 (CH), 128.0 (2×CH), 124.9 (2×CH), 124.8 (CH), 123.0 (C), 119.7 (CH), 109.7 (CH), 108.9 (CH), 55.4 (2×$CH_2$), 55.0 (2×$CH_2$), 46.2 ($CH_3$). HRMS [M+H]$^+$ $C_{26}H_{24}BrN_4O_3S$: Calcd. 551.0747 found 551.0724. Purity: 100%.

((prop-2-yn-1-yloxy)methanetriyl)tribenzene

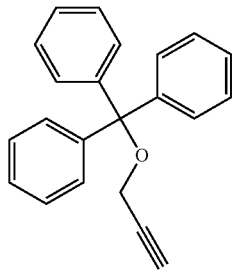 [SMILES: C#CCOC(c1ccccc1)(c1ccccc1)c1ccccc1]

To a solution of triphenylmethyl chloride (500 mg, 1.79 mmol) in DCM (740 µL) was added DMAP (4.8 mg, 0.02 eq.), pyridine (140 µL, 1.8 mmol) and 2-propynol (740 µL, 1.79 mmol). After 16 h stirring at room temperature, the reaction mixture was neutralized with water. The aqueous layer was extracted three time with EA. The combined organic layers were dried over $Na_2SO_4$, and concentrated in vacuo. Purification by silica gel flash chromatography (EA 100%) afforded a colourless oil (559 mg, quant.). $^1$H NMR (300 MHz, $CDCl_3$) δ 7.57-7.53 (m, 6H, Har), 7.39-7.33 (m, 9H, Har), 3.83 (d, J=2.4 Hz, 2H, $CH_2$), 2.44 (t, J=2.4 Hz, 1H, CH). $^{13}$C NMR (75 MHz, $CDCl_3$) δ 143.7 (C), 128.9 (6×CH), 128.3 (6×CH), 127.5 (3×CH), 87.9 (C), 80.7 (C), 73.8 (CH), 53.2 ($CH_2$).

2-bromo-1-(4-bromophenyl)ethanone

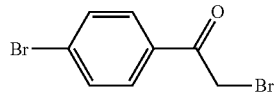

To a solution of 3'-bromoacetophenone (4 g, 20 mmol) in EA (30 mL) and $CHCl_3$ (30 mL) was added $CuBr_2$ (8.9 g, 40 mmol). The solution was refluxed overnight. After cooling, the mixture was evaporated to dryness under vacuum. The resulting solid was dissolved in AE, filtered through a Celite pad and washed with AE. The organic layer was then washed with a saturated $NaHCO_3$ solution, dried over $Na_2SO_4$, filtered and evaporated under vacuum. Purification by silica gel flash chromatography (EP/DCM 4:1) afforded the product (4.66 g, 85%) as a colourless viscous oil. $^1$H NMR (300 MHz, $CDCl_3$) δ 7.85 (d, J=8.6 Hz, 2H, Har), 7.63 (d, J=8.6 Hz, 2H, Har), 4.40 (s, 2H, $CH_2$). $^{13}$C NMR (75 MHz, $CDCl_3$) δ 190.7 (C), 133.0 (C), 132.5 (2×CH), 130.7 (2×CH), 129.6 (C), 30.7 ($CH_2$). HRMS (ESI) [M+H]$^+$ $C_8H_7Br_2O$: Calcd. 276.8858 found 276.8854.

4-(4-bromophenyl)thiazol-2-amine

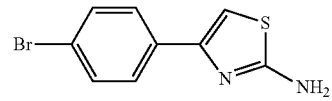 [SMILES: Nc1nc(-c2ccc(Br)cc2)cs1]

To a stirred suspension of 2-bromo-1-(4-bromophenyl)ethanone (4.66 g, 16.9 mmol) in EtOH (105 mL) was added thiourea (1.53 g, 20 mmol) and the mixture was heated at 70° C. overnight. After cooling to room temperature, the solvent was evaporated to dryness. The resulting solid was stirred in a mixture of EtOAc/saturated aqueous $NaHCO_3$ solution (2:1) until dissolution, and then extracted with EtOAc. The organic layer was dried over $Na_2SO_4$, filtrated and the solvent was removed under reduced pressure. The product was crystallized in PE and filtered to afford a yellow solid (4.21 g, 98%). $^1$H NMR (300 MHz, MeOD) δ 7.66 (d, J=8.6 Hz, 2H, Har), 7.49 (d, J=8.6 Hz, 2H, Har), 6.85 (s, 1H, Har). $^{13}$C NMR (75 MHz, MeOD) δ 150.5 (C), 135.3 (C), 132.6 (2×CH), 128.7 (2×CH), 122.2 (C), 103.5 (CH). HRMS (ESI) [M+H]$^+$ $C_9H_8BrN_2S$: Calcd. 254.9586 found 254.9577.

N-(4-(4-bromophenyl)thiazol-2-yl)-4-((4-methylpiperazin-1-yl)methyl)benzamide

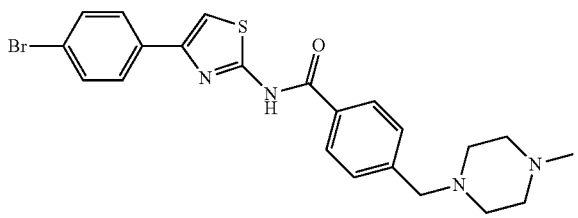

4-(4-bromophenyl)thiazol-2-amine (1 g, 3.9 mmol) was diluted with toluene (4 mL) in a two necked round bottom flask equipped with a reflux condenser under an argon atmosphere. The solution was stirred and trimethylaluminium in toluene (1.84 mL, 2M) was slowly added. The solution was heated at 50° C. during 20 min and the ester (645 mg, 2.6 mmol) in toluene (2 mL) was added. The resulting solution was heated under reflux for one night, cooled to room temperature and slowly hydrolyzed with water to prevent foam formation. The aqueous layer was based with a 1M NaOH solution (pH9-10). The mixture was extracted three times with DCM, and the organic layers were combined and dried over $Na_2SO_4$. The solvent was evaporated under reduced pressure. Purification by silica gel flash chromatography (DCM/MeOH 9:1) afforded the product (584 mg, 48%) as a yellow solid. $^1$H NMR (300 MHz, $CDCl_3$) δ 10.35 (bs, 1H, NH), 7.81 (d, J=7.8 Hz, 2H, Har), 7.62 (d, J=8.2 Hz, 2H, Har), 7.45 (d, J=8.2 Hz, 2H, Har), 7.39 (d, J=7.7 Hz, 2H, Har), 7.18 (s, 1H, Har), 3.54 (s, 2H, $CH_2$), 2.51 (bs, 8H, 2×$CH_2$), 2.34 (s, 3H, $CH_3$). $^{13}$C NMR (75 MHz, $CDCl_3$) δ 165.1 (C), 159.1 (C), 149.3 (C), 144.3 (C), 133.5 (C), 132.1 (2×CH), 130.9 (C), 129.6 (2×CH), 127.9 (2×CH), 127.8 (2×CH), 122.3 (C), 108.8 (CH), 62.7 ($CH_2$), 55.3 (2×$CH_2$), 53.2 (2×$CH_2$), 46.1 ($CH_3$). HRMS [M+H]$^+$ $C_{22}H_{24}BrN_4OS$: Calcd. 471.0849 found 471.0841.

methyl 4-(morpholinomethyl)benzoate

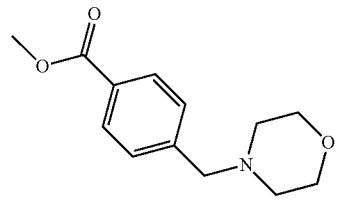 [SMILES: COC(=O)c1ccc(CN2CCOCC2)cc1]

To a solution of methyl 4-(bromomethyl)benzoate (1 g, 4.36 mmol), $K_2CO_3$ (1.02 g, 7.4 mmol) in $CH_3CN$ at 0° C. was added the morpholine(418 μL, 4.8 mmol). The mixture was stirred 7 hours at room temperature. The mixture was filtered through Celite pad, washed with EtOAc and evaporated to dryness to give the product as a colourless oil. (1.02 g, quanti.). $^1$H NMR (300 MHz, $CDCl_3$) δ 7.85 (d, J=8.3 Hz, 2H, Har), 7.27 (d, J=8.2 Hz, 2H, Har), 3.76 (s, 2H, Har), 3.56 (t, J=4.7 Hz, 2H, 2×$CH_2$), 3.39 (s, 2H, $CH_2$), 2.29 (t, J=4.6 Hz, 2H, 2×$CH_2$). $^{13}$C NMR (75 MHz, $CDCl_3$) δ 167.0 (C), 143.5 (C), 129.7 (2×CH), 129.1 (C), 129.0 (2×CH), 67.0 ($CH_2$), 63.1 ($CH_2$), 53.7 (2×$CH_2$), 52.1 ($CH_3$). HRMS [M+H]$^+$ $C_{13}H_{18}NO_3$: Calcd. 236.1281 found 236.1290.

N-(4-(3-bromophenyl)thiazol-2-yl)-4-(morpholinomethyl)benzamide

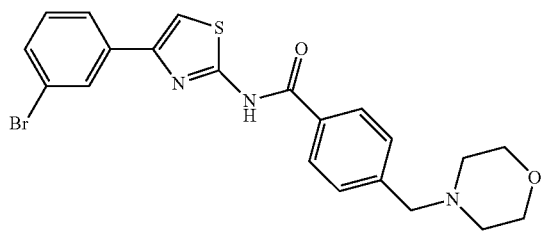 [SMILES: O=C(Nc1nc(-c2cccc(Br)c2)cs1)c1ccc(CN2CCOCC2)cc1]

4-(3-bromophenyl)thiazol-2-amine (600 mg, 2.35 mmol) was diluted with toluene (2 mL) in a two necked round bottom flask equipped with a reflux condenser under an argon atmosphere. The solution was stirred and trimethylaluminium in toluene (1.1 mL, 2M) was slowly added. The solution was heated at 50° C. during 20 min and the ester (370 mg, 1.56 mmol) in toluene (1.6 mL) was added. The resulting solution was heated under reflux for one night, cooled to room temperature and slowly hydrolyzed with water to prevent foam formation. The aqueous layer was based with a 1M NaOH solution (pH9-10). The mixture was extracted three times with DCM, and the organic layers were combined and dried over $Na_2SO_4$. The solvent was evaporated under reduced pressure. Purification by silica gel flash chromatography (DCM/MeOH 9:1) afforded the product (593 mg, 83%) as a yellow solid. $^1$H NMR (300 MHz, $CDCl_3$) δ 10.58 (bs, 1H, NH), 7.89 (dd, J=1.5, 1.5 Hz, 1H, Har), 7.82 (d, J=8.2 Hz, 2H, Har), 7.65 (ddd, J=7.8, 1.4, 1.4 Hz, 1H, Har), 7.40 (d, J=8.1 Hz, 2H, Har), 7.38-7.33 (m, 1H, Har), 7.20 (s, 1H, Har), 7.17 (dd, J=7.9, 7.9 Hz, 1H, Har), 3.74 (t, J=4.4 Hz, 4H, 2×$CH_2$), 3.55 (s, 2H, $CH_2$), 2.45 (t, J=4.4 Hz, 4H, 2×$CH_2$). $^{13}$C NMR (75 MHz, $CDCl_3$) δ 164.9 (C), 158.9 (C), 148.6 (C), 136.3 (C), 130.9 (CH), 130.3 (CH), 129.6 (C), 129.6 (2×CH), 129.2 (CH), 127.6 (2×CH), 124.6 (CH), 122.9 (C), 109.2 (CH), 66.9 (2×$CH_2$), 62.8 ($CH_2$), 53.6 (2×$CH_2$). HRMS [M+H]$^+$ $C_{21}H_{21}BrN_3O_2S$: Calcd. 458.0532 found 458.0528.

methyl 4-((1H-tetrazol-1-yl)methyl)benzoate

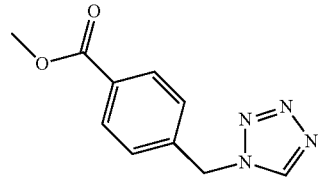 [SMILES: COC(=O)c1ccc(Cn2cnnn2)cc1]

To a solution of methyl 4-(bromomethyl)benzoate (500 g, 2.18 mmol), $Cs_2CO_3$ (781 mg, 2.4 mmol) in DMF was added the tetrazole (143 mg, 2.04 mmol). The mixture was stirred overnight at room temperature. The mixture was filtered through Celite pad, washed with EtOAc and evaporated to dryness. The oil was partitioned between $Et_2O$ and water. The organic layer was dried over $Na_2SO_4$ and evaporated under reduced pressure to give a mixture of two tautomers. Purification by silica gel flash chromatography (PE/EA 3:7) afforded the tautomer 1 (212 mg, 48%) as a white solid. $^1$H NMR (300 MHz, $CDCl_3$) δ 8.86 (s, 1H, Har), 7.89 (d, J=7.9 Hz, 2H, Har), 7.28 (d, J=7.9 Hz, 2H, Har), 5.66 (s, 2H, $CH_2$), 3.79 (s, 3H, $CH_3$). $^{13}$C NMR (75 MHz, $CDCl_3$) δ 166.2 (C), 143.1 (CH), 138.0 (C), 130.7 (C), 130.3 (2×CH), 128.1 (2×CH), 52.3 ($CH_3$), 51.4 ($CH_2$). HRMS [M+Na]$^+$ $C_{10}H_{10}N_4NaO_2$: Calcd. 241.0696 found 241.0689.

71

4-((1H-tetrazol-1-yl)methyl)-N-(4-(3-bromophenyl)thiazol-2-yl)benzamide

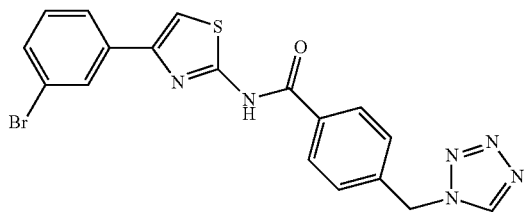 [SMILES: O=C(Nc1nc(-c2cccc(Br)c2)cs1)c1ccc(Cn2cnnn2)cc1]

4-(3-bromophenyl)thiazol-2-amine (100 mg, 0.39 mmol) was diluted with toluene (400 µL) in a two necked round bottom flask equipped with a reflux condenser under an argon atmosphere. The solution was stirred and trimethylaluminium in toluene (185 µL, 2M) was slowly added. The solution was heated at 50° C. during 20 min and the ester (57 mg, 0.26 mmol) in toluene (200 µL) was added. The resulting solution was heated under reflux for one night, cooled to room temperature and slowly hydrolyzed with water to prevent foam formation. The aqueous layer was based with a 1M NaOH solution (pH9-10). The mixture was extracted three times with DCM, and the organic layers were combined and dried over Na₂SO₄. The solvent was evaporated under reduced pressure. Purification by silica gel flash chromatography (DCM/Acetone 8:2) afforded the product (41.3 mg, 24%) as a yellow viscous oil. The crude product was used without further purifications.

methyl 4-(((2-(dimethylamino)ethyl)amino)methyl)benzoate

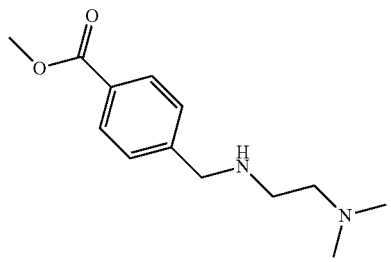

To a solution of methyl 4-(bromomethyl)benzoate (500 g, 2.18 mmol), K₂CO₃ (501 mg, 3.70 mmol) in DMF was added the N,N-Dimethylethylenediamine (262 µL, 2.4 mmol). The mixture was stirred overnight at 45° C. The mixture was filtered through Celite pad, washed with DCM. The organic layer was extracted with a 1M HCl solution. The aqueous layer was basified at pH 10 with a 1M NaOH solution and extracted three time with EA. The organic layer was dried over Na₂SO₄ and evaporated under reduced pressure to give the product (100 mg, 20%) as a white oil. $^1$H NMR (300 MHz, CDCl₃) δ 7.92 (d, J=8.3 Hz, 2H, Har), 7.33 (d, J=8.4 Hz, 2H, Har), 3.82 (s, 3H, CH₃), 3.79 (s, 2H, CH₂), 2.60 (t, J=6.0 Hz, 2H, CH₂), 2.35 (t, J=6.0 Hz, 2H, CH₂), 2.12 (s, 6H, (CH₃)₂N). $^{13}$C NMR (75 MHz, CDCl₃) δ 167.2 (C), 146.1 (C), 129.8 (2×CH), 128.8 (C), 128.1 (2×CH), 59.1 (CH₂), 53.8 (CH₂), 52.1 (CH₃), 46.7 (CH₂), 45.6 (2×CH₃). HRMS [M+H]⁺ C₁₃H₂₁N₂O₂: Calcd. 237.1598 found 237.1600.

72

N-(4-(3-bromophenyl)thiazol-2-yl)-4-(((2-(dimethylamino)ethyl)amino)methyl)benzamide

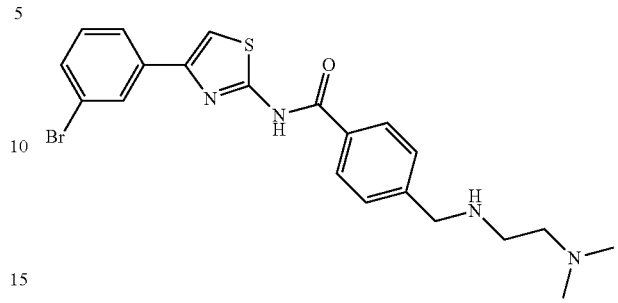

4-(3-bromophenyl)thiazol-2-amine (160 mg, 0.63 mmol) was diluted with toluene (700 µL) in a two necked round bottom flask equipped with a reflux condenser under an argon atmosphere. The solution was stirred and trimethylaluminium in toluene (298 µL, 2M) was slowly added. The solution was heated at 50° C. during 20 min and the ester (100 mg, 0.42 mmol) in toluene (270 µL) was added. The resulting solution was heated under reflux for one night, cooled to room temperature and slowly hydrolyzed with water to prevent foam formation. The aqueous layer was based with a 1M NaOH solution (pH 9-10). The mixture was extracted three times with DCM, and the organic layers were combined and dried over Na₂SO₄. The solvent was evaporated under reduced pressure. Purification by silica gel flash chromatography (DCM/MeOH/H₂O 65:25:4) afforded the product (49.3 mg, 26%) as a yellow viscous oil. $^1$H NMR (300 MHz, CDCl₃) δ 7.89 (bs, 1H, Har), 7.78 (d, J=7.9 Hz, 2H, Har), 7.65 (d, J=7.7 Hz, 1H, Har), 7.38-7.30 (m, 3H, Har), 7.21-7.14 (m, 2H, Har), 6.34 (bs, 1H, Har), 3.84 (s, 2H, CH₂), 2.72 (t, J=5.8 Hz, 2H, CH₂), 2.46 (t, J=5.8 Hz, 2H, CH₂), 2.20 (s, 6H, (CH₃)₂N). $^{13}$C NMR (75 MHz, CDCl₃) δ 165.5 (C), 159.4 (C), 148.8 (C), 145.9 (C), 136.6 (C), 131.0 (CH), 130.9 (C), 130.4 (CH), 129.4 (CH), 128.7 (2×CH), 128.0 (2×CH), 124.8 (CH), 123.1 (C), 109.3 (CH), 59.1 (CH₂), 53.8 (CH₂), 46.8 (CH₂), 45.7 (2×CH₃). HRMS [M+H]⁻ C₂₁H₂₄BrN₄OS: Calcd. 459.0849 found 459.0827.

methyl 4-((1H-imidazol-1-yl)methyl)benzoate

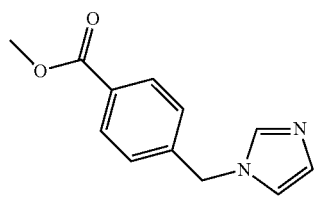 [SMILES: COC(=O)c1ccc(Cn2ccnc2)cc1]

To a solution of methyl 4-(bromomethyl)benzoate (500 g, 2.18 mmol), Cs₂CO₃ (781 mg, 2.4 mmol) in DMF (10 mL) was added the imidazole (163 mg, 2.4 mmol). The mixture was heated one hour in microwave at 150° C. The mixture was filtered through Celite pad, washed with DCM. The organic layer was washed twice with water, dried over Na₂SO₄ and evaporated under reduced pressure to give the product (381 mg, 81%) as a colourless oil. $^1$H NMR (300 MHz, CDCl₃) δ 7.96 (d, J=8.4 Hz, 2H, Har), 7.51 (s, 1H, Har), 7.14 (d, J=8.6 Hz, 2H, Har), 7.05 (s, 1H, Har), 6.86 (s, 1H, Har), 5.14 (s, 2H, CH$_2$), 3.86 (s, 3H, CH$_3$). $^{13}$C NMR (75 MHz, CDCl$_3$) δ 166.4 (C), 141.2 (C), 137.5 (CH), 130.2 (2×CH), 130.0 (C), 127.0 (2×CH), 119.3 (CH), 52.2 (CH$_3$), 50.3 (CH$_2$). HRMS [M+H]$^+$ C$_{12}$H$_{13}$N$_2$O$_2$: Calcd. 217.0970 found 217.0972.

4-((1H-imidazol-1-yl)methyl)-N-(4-(3-bromophenyl)thiazol-2-yl)benzamide

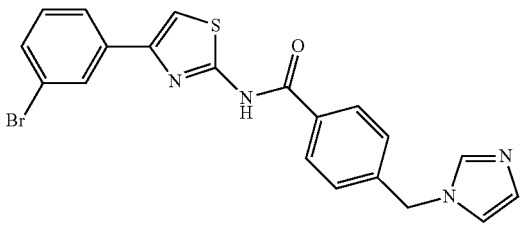 [SMILES: O=C(Nc1nc(-c2cccc(Br)c2)cs1)c1ccc(Cn2ccnc2)cc1]

4-(3-bromophenyl)thiazol-2-amine (100 mg, 0.39 mmol) was diluted with toluene (400 µL) in a two necked round bottom flask equipped with a reflux condenser under an argon atmosphere. The solution was stirred and trimethylaluminium in toluene (185 µL, 2M) was slowly added. The solution was heated at 50° C. during 20 min and the ester (56 mg, 0.26 mmol) in toluene (200 µL) was added. The resulting solution was heated under reflux for one night, cooled to room temperature and slowly hydrolyzed with water to prevent foam formation. The aqueous layer was based with a 1M NaOH solution (pH 9-10). The mixture was extracted three times with DCM, and the organic layers were combined and dried over Na$_2$SO$_4$. The solvent was evaporated under reduced pressure. Purification by silica gel flash chromatography (DCM/MeOH 9:1) afforded the product (57.2 mg, 50%) as a yellow viscous oil. $^1$H NMR (300 MHz, MeOD) δ 7.85-7.80 (m, 3H, Har), 7.59-7.54 (m, 1H, Har), 7.44 (s, 1H, Har), 7.23 (ddd, J=8.0, 1.9, 1.0 Hz, 1H, Har), 7.10 (d, J=8.5 Hz, 2H, Har), 7.09-7.08 (m, 1H, Har), 7.07 (s, 1H, Har), 6.85 (s, 1H, Har), 6.80 (s, 1H, Har), 4.23 (s, 2H, CH$_2$). $^{13}$C NMR (75 MHz, MeOD) δ 165.3 (C), 148.5 (C), 141.1 (C), 136.4 (C), 132.1 (C), 130.7 (CH), 130.2 (CH), 129.0 (CH), 129.0 (C), 128.5 (2×CH), 127.5 (2×CH), 124.5 (CH), 122.7 (C), 109.1 (CH), 50.3 (CH$_2$). HRMS [M+H]$^{+C}$$_{20}$H$_{16}$BrN$_4$OS: Calcd. 439.0223 found 439.0223.

2-isopropoxy-2-oxoethanaminium chloride

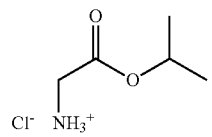

Glycine (1g, 13.3 mmol) was dissolved in isopropanol (10 mL) at 0° C. SOCl$_2$ (1.93 mL, 26.6 mmol) was added dropwise. The mixture was stirred at reflux overnight. After cooling, the solvent was evaporated under reduced pressure and hexane was added at 0° C. The suspension was filtered to afford the product (1.76 g, 86%) as a white solid. $^1$H NMR (300 MHz, MeOD) δ 5.13 (hept, J=6.3 Hz, 1H, (CH$_3$)$_2$CHO), 3.81 (s, 2H, CH$_2$), 1.32 (s, 3H, (CH$_3$)$_2$CHO), 1.30 (s, 3H, (CH$_3$)$_2$CHO). $^{13}$C NMR (75 MHz, MeOD) δ 168.0 (C), 71.7 ((CH$_3$)$_2$CHO), 41.2 (CH$_2$), 21.9 ((CH$_3$)$_2$CHO). HRMS [M+H]$^+$ C$_5$H$_{12}$NO$_2$: Calcd. 118.0858 found methyl 4-(2-isopropoxy-2-oxoethyl)benzoate

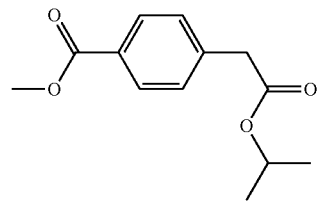 [SMILES: COC(=O)c1ccc(CC(=O)OC(C)C)cc1]

To a solution of methyl 4-(bromomethyl)benzoate (500 g, 2.18 mmol), K$_2$CO$_3$ (854 mg, 6.33 mmol) in CH$_3$CN at 0° C. was added the 2-isopropoxy-2-oxoethanaminium chloride (368 mg, 2.4 mmol). The mixture was stirred two days at room temperature. The mixture was filtered through Celite pad, washed with EA and evaporated to dryness to give the product as a colourless oil. (318 mg, 55%).
$^1$H NMR (300 MHz, CDCl$_3$) δ 7.96 (d, J=8.3 Hz, 2H, Har), 7.38 (d, J=8.3 Hz, 2H, Har), 5.04 (hept, J=6.3 Hz, 1H, (CH$_3$)$_2$CHO), 3.87 (s, 3H, CH$_3$), 3.83 (s, 2H, CH$_2$), 3.34 (s, 2H, CH$_2$), 2.39 (s, 1H, NH), 1.23 (s, 3H, (CH$_3$)$_2$CHO), 1.21 (s, 3H, (CH$_3$)$_2$CHO). $^{13}$C NMR (75 MHz, CDCl$_3$) δ 172.0 (C), 167.2 (C), 145.1 (C), 130.0 (2×CH), 129.3 (C), 128.4 (2×CH), 68.7 ((CH$_3$)$_2$CHO), 53.1 (CH$_2$), 52.3 (CH$_3$), 50.5 (CH$_2$), 22.1 ((CH$_3$)$_2$CHO). HRMS [M+H]$^+$ C$_5$H$_{12}$NO$_2$: Calcd. 118.0858 found 118.0863.

4-(bromomethyl)-N-(4-(3-bromophenyl)thiazol-2-yl)benzamide

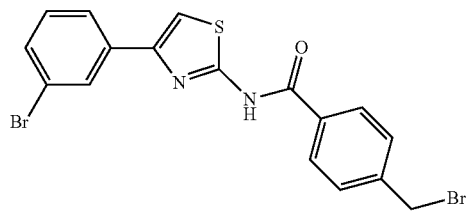 [SMILES: O=C(Nc1nc(-c2cccc(Br)c2)cs1)c1ccc(CBr)cc1]

4-(3-bromophenyl)thiazol-2-amine (200 mg, 0.78 mmol) was diluted with toluene (800 µL) in a two necked round bottom flask equipped with a reflux condenser under an argon atmosphere. The solution was stirred and trimethylaluminium in toluene (488 µL, 2M) was slowly added. The solution was heated at 50° C. during 20 min and the ester (150 mg, 0.65 mmol) in toluene (400 µL) was added. The resulting solution was heated under reflux for one night, cooled to room temperature and slowly hydrolyzed with water to prevent foam formation. The aqueous layer was extracted three times with DCM, and the organic layers were combined and dried over Na$_2$SO$_4$. The solvent was evaporated under reduced pressure. Purification by silica gel flash chromatography (PE/EE 1:1) afforded the product (189 mg, 65%) as a yellow viscous oil. $^1$H NMR (300 MHz, CDCl$_3$) δ 11.61 (bs, 1H, NH), 7.79-7.69 (m, 3H, Har), 7.57-7.48 (m, 1H, Har), 7.33-7.23 (m, 3H, Har), 7.18 (s, 1H, Har), 7.10 (dd, J=7.7, 7.7 Hz, 1H, Har), 4.44 (s, 2H, CH$_2$). $^{13}$C NMR (75 MHz, CDCl$_3$) δ 165.2 (C), 159.9 (C), 148.7 (C), 142.6 (C), 136.1 (C), 131.8 (C), 131.1 (CH), 130.4 (CH), 129.4

(2×CH), 129.3 (CH), 128.2 (2×CH), 124.8 (CH), 123.0 (C), 109.5 (CH), 32.3 (CH$_2$). HRMS [M+H]$^+$ C$_{17}$H$_{13}$Br$_2$N$_2$OS: Calcd. 450.9126 found 450.9110.

isopropyl 2-((4-((4-(3-bromophenyl)thiazol-2-yl)carbamoyl)benzl)amino)acetate

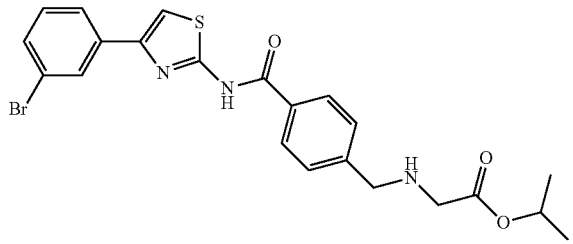 [SMILES: CC(C)OC(=O)CNCc1ccc(C(=O)Nc2nc(-c3cccc(Br)c3)cs2)cc1]

To a solution of 4-(bromomethyl)-N-(4-(3-bromophenyl)thiazol-2-yl)benzamide (60 g, 0.13 mmol), K$_2$CO$_3$ (53 mg, 0.38 mmol) in CH$_3$CN at 0° C. was added the 2-isopropoxy-2-oxoethanaminium chloride (22.3 mg, 0.145 mmol). The mixture was stirred two days at room temperature. The mixture was filtered through Celite pad, washed with DCM and evaporated to dryness. Purification by silica gel flash chromatography (DCM/MeOH 95:5) afforded the product (28.5 mg, 45%) as a yellow viscous oil. $^1$H NMR (300 MHz, CDCl$_3$) δ 7.88 (dd, J=1.7, 1.7 Hz, 1H, Har), 7.80 (d, J=8.3 Hz, 2H, Har), 7.65 (ddd, J=7.8, 1.5, 1.1 Hz, 1H, Har), 7.37 (ddd, J=8.0, 1.9, 1.0 Hz, 1H, Har), 7.34 (d, J=8.2 Hz, 2H, Har), 7.19 (s, 1H, Har), 7.18 (dd, J=7.9, 7.9 Hz, 1H, Har), 5.10 (Hept, J=6.3 Hz, 1H, Har), 3.85 (s, 2H, CH$_2$), 3.43 (s, 2H, CH$_2$), 1.27 (s, 3H, (CH$_3$)$_2$CHO), 1.24 (s, 3H, (CH3$_2$CHO). $^{13}$C NMR (75 MHz, CDCl$_3$) δ 171.87 (C), 165.30 (C), 159.33 (C), 148.83 (C), 144.67 (C), 136.54 (C), 131.17 (C), 131.12 (CH), 130.47 (CH), 129.43 (CH), 128.87 (2×CH), 128.07 (2×CH), 124.82 (CH), 123.15 (C), 109.39 (CH), 69.02 ((CH$_3$)$_2$CHO), 52.97 (CH$_2$), 50.57 (CH$_2$), 22.17 ((CH3$_2$CHO). HRMS [M+H]$^+$ C$_{22}$H$_{23}$BrN$_3$O$_3$S: Calcd. 488.0624 found 488.0638.

BIOLOGICAL ACTIVITY

Biochemical and Cellular Assays

Compounds of the invention that have been tested in the above described ELISA-based in vitro kinase assay and in the Tritiated thymidine uptake cell proliferation in BAF3 cells assay tabulated in the table below.

| Example number | ALK WT IC50 (μM) | ALK L1196M IC50 (μM) | Parental IC50 (μM) | NPM/ALK WT IC50 (μM) | NPM/ALK L1196M IC50 (μM) | Selectivity Index (WT) | Selectivity Index (1196M) |
|---|---|---|---|---|---|---|---|
| 1 | 71 | 5.6 | 4.7 | 1.4 | 0.69 | 3 | 7 |
| 2 | 82 | 5.8 | 5.5 | 0.85 | 2.6 | 6 | 2 |
| 3 | 45 | 4.8 | 2.3 | 0.67 | 1.4 | 3 | 2 |
| 4 | 50 | 6.4 | 5.3 | 2.4 | 2.3 | 2 | 2 |
| 5 | 83 | 2.7 | 5.3 | 1.9 | 2.3 | 3 | 2 |
| 6 | >100 | 6.3 | 6.6 | 2.1 | 2.3 | 3 | 3 |
| 7 | 54 | 1.9 | 5.0 | 2.5 | 1.3 | 2 | 4 |
| 8 | 23 | 5.8 | 1.5 | 0.85 | 0.46 | 2 | 3 |
| 9 | >100 | 8 | 4.0 | 2.3 | 0.90 | 2 | 4 |
| 10 | 15 | 2.6 | 3 | 1.1 | 0.29 | 3 | 10 |
| 11 | 20 | 2.4 | 3.2 | 2.4 | 0.16 | 1 | 20 |
| 12 | 12 | 1.7 | 1.8 | 2.1 | 0.14 | 1 | 13 |
| 13 | 3.3 | 0.3 | 3.1 | 5.6 | 0.57 | 1 | 5 |
| 14 | 1.3 | 0.71 | 7.8 | 2.2 | 6.2 | 4 | 1 |
| 15 | 0.64 | 0.60 | 14 | 1.2 | 7 | 12 | 2 |
| 16 | 0.54 | 0.54 | >50 | 41 | 14 | 1 | 4 |
| 17 | 8.6 | 1.6 | 0.46 | 1.1 | 0.79 | 0 | 1 |
| 18 | 40 | 21 | 0.45 | 1.2 | 1.9 | 0 | 0 |
| 19 | 76 | 5.6 | 0.49 | 1.3 | 3.7 | 0 | 0 |
| 20 | 38 | 31 | 7.3 | 2.8 | 1.9 | 3 | 4 |
| 21 | 1.5 | 0.70 | 12 | 4.6 | 5.7 | 3 | 2 |
| 22 | 4.2 | 1.1 | 8.5 | 2.0 | 1.2 | 4 | 7 |
| 23 | 51 | 45 | 5.9 | 2.3 | 1.2 | 3 | 5 |
| 24 | 1.5 | 0.36 | 2.4 | 1.6 | 1.1 | 1 | 2 |
| 25 | 1.7 | 0.87 | 12 | 6.7 | 3.8 | 2 | 3 |
| 26 | 0.42 | 0.0446 | 11 | 8.7 | 9.4 | 1 | 1 |
| 27 | 0.4281 | 0.0331 | 2.3 | 1.6 | 1.4 | 1 | 2 |
| 28 | 2.127 | 0.0556 | 3.7 | 6.1 | 4.0 | 1 | 1 |
| 29 | 0.3854 | 0.0467 | 10.0 | 7.2 | 0.057 | 1 | 175 |
| 30 | 2.1 | 0.83 | 10 | 0.69 | 3.4 | 15 | 3 |
| 31 | 5.0 | 8.9 | 2.2 | 0.87 | 0.50 | 3 | 4 |
| 32 | 15 | 11 | 2.4 | 2.0 | 2.1 | 1 | 1 |
| 33 | 4.1 | 2.9 | 7.1 | 2.3 | 1.6 | 3 | 4 |
| 34 | >100 | >100 | 4.0 | 1.9 | 1.7 | 2 | 2 |
| 35 | 1.9 | 5.8 | 7.3 | 2.9 | 2.4 | 3 | 3 |
| 36 | 1.9 | 1.1 | 6.9 | 0.88 | 2.1 | 8 | 3 |
| 37 | 4.6 | 2.1 | 2.4 | 0.61 | 1.2 | 4 | 2 |
| 38 | 7.0 | 2.3 | >50 | 10 | 2.3 | >5 | >22 |
| 39 | >100 | 27 | 33 | 9.0 | 1.3 | 4 | 26 |
| 40 | 9.4 | 4.4 | 18 | 5.1 | 0.80 | 4 | 23 |
| 41 | 7.0 | 2.7 | >50 | 22 | 0.83 | >2 | >60 |
| 42 | 53 | 3.7 | 2.6 | 2.9 | 0.96 | 1 | 3 |
| 43 | >100 | 1.3 | 4.5 | 4.9 | 0.86 | 1 | 5 |
| 44 | >100 | 65 | 7.8 | 5.1 | 5.4 | 2 | 1 |

-continued

| Example number | ALK WT IC50 (μM) | ALK L1196M IC50 (μM) | Parental IC50 (μM) | NPM/ALK WT IC50 (μM) | NPM/ALK L1196M IC50 (μM) | Selectivity Index (WT) | Selectivity Index (1196M) |
|---|---|---|---|---|---|---|---|
| 45 | 50 | 30 | 8.0 | 5.1 | 3.2 | 2 | 2 |
| 46 | 52 | 39 | 11 | 6.9 | 3.9 | 2 | 3 |
| 47 | 46 | >100 | >25 | >25 | >25 | 1 | 1 |
| 48 | 0.20 | 0.91 | 13 | 1.6 | 3.1 | 8 | 4 |
| 49 | 26 | 99 | 4 | 1.7 | 1.9 | 2 | 2 |
| 50 | 2.8 | 3.6 | >50 | 10 | 5.2 | >5 | >10 |

The invention claimed is:

1. The compounds of formula (I)

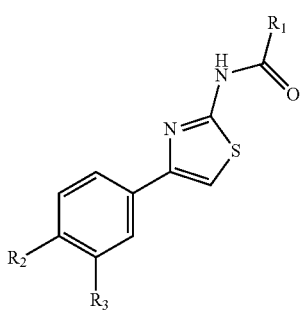

wherein:
—$R_1$ is

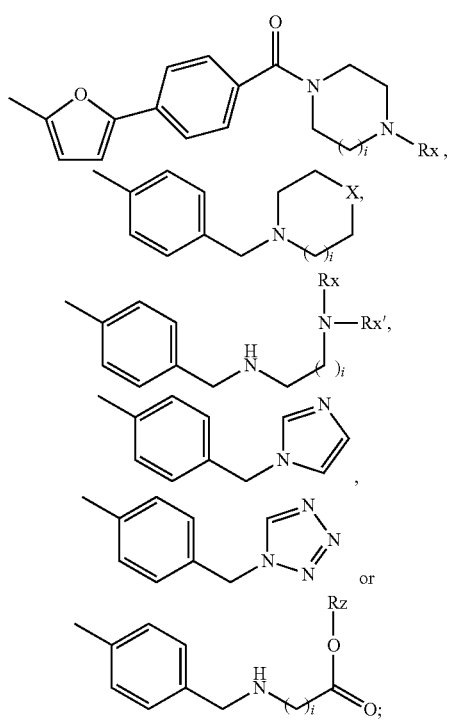

i equals zero, 1 or 2
Rx and Rx' can be the same or different and are a $C_1$-$C_3$ linear or branched alkyl;
X is either oxygen or NRy;
Ry is a $C_1$-$C_3$ linear or branched alkyl or propargyl;
Rz is either hydrogen or $C_1$-$C_3$ linear or branched alkyl;
—$R_2$ and —$R_3$ can be the same or different and are hydrogen, linear or branched $C_1$-$C_3$ alkyl or —C≡C—$R_4$, provided that at least one of —$R_2$ and —$R_3$ is —C≡C—$R_{49}$;
—$R_4$ is hydrogen, —$CH_2$—O—$CPh_3$, cyclohexenyl, $C_1$-$C_4$ alkyl,

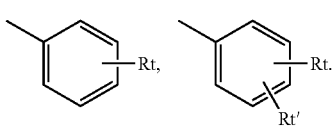

Rt and Rt' can be the same or different and are $C_1$-$C_3$ alkyl optionally substituted with one or more fluorine atoms, $C_1$-$C_3$ alkoxy optionally substituted with one or more fluorine atoms or F;
Ra, Rb and Rc can be the same or different and can be phenyl or $C_1$-$C_4$ linear or branched alkyl;
and pharmaceutically acceptable salts thereof.

2. The compounds of claim 1 wherein
$R_2$ is hydrogen or linear or branched $C_1$-$C_3$ alkyl; and
$R_3$ is —C≡C—$R_4$.

3. The compounds of claim 1 wherein
—$R_2$ is —C≡C—$R_4$; and
$R_3$ is hydrogen or linear or branched $C_1$-$C_3$ alkyl.

4. The compounds of claim 2, wherein —$R_4$ is selected from the list of

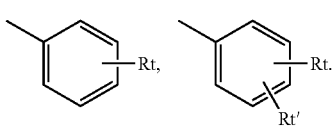

5. The compounds of claim 2, wherein —$R_4$ is selected from the list of

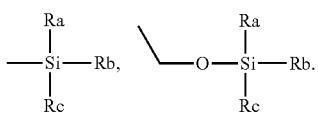

6. The compounds of claim 4 wherein —R₁ is

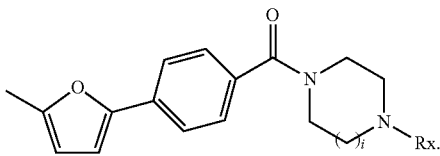

7. The compounds of claim 4 wherein —R₁ is

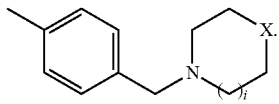

8. The compounds of claim 4 wherein —R₁ is selected from the list of

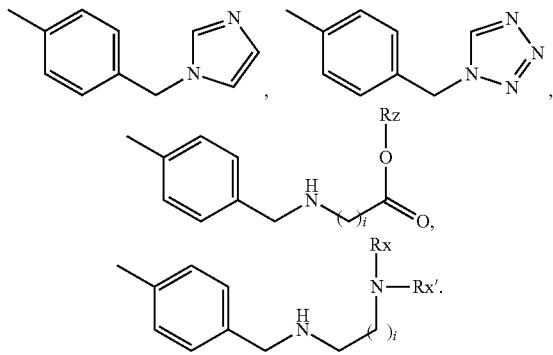

9. The compounds of claim 1 selected from the list of 4((4-methylpiperazin-1-yl)methyl)-N-(4-(3-(phenylethynyl)phenyl)thiazol-2-yl)benzamide;
4((4-methylpiperazin-1-yl)methyl)-N-(4-(3-(p-tolylethynyl)phenyl)thiazol-2-yl)benzamide;
N-(4-(3-((4-methoxyphenyl)ethynyl)phenyl)thiazol-2-yl)-4-((4-methylpiperazin-1-yl)methyl)benzamide;
N-(4-(4-methyl-3-(phenylethynyl)phenyl)thiazol-2-yl)-4-((4-methylpiperazin-1-yl)methyl)benzamide
N-(4-(4-methyl-3-(p-tolylethynyl)phenyl)thiazol-2-yl)-4-((4-methylpiperazin-1-yl)methyl)benzamide;
N-(4-(3-((4-methoxyphenyl)ethynyl)-4-methylphenyl)thiazol-2-yl)-4-((4-methylpiperazin-1-yl)methyl)benzamide;
N-(4-(4-methyl-3((2-(trifluoromethyl)phenyl)ethynyl)phenyl)thiazol-2-yl)-4-((4-methylpiperazin-1-yl)methyl)benzamide;
N-(4-(3-((2-methoxyphenyl)ethynyl)-4-methylphenyl)thiazol-2-yl)-4-((4-methylpiperazin-1-yl)methyl)benzamide;
N-(4-(3((-fluorophenyl)ethynyl)-4-methylphenyl)thiazol-2-yl)-4-((4-methylpiperazin-1-yl)methyl)benzamide;
N-(4-(3-methyl-4-(p-tolylethynyl)phenyl)thiazol-2-yl)-4-((4-methylpiperazin-1-yl)methyl)benzamide;
N-(4-(3-methyl-4-((2-(trifluoromethyl)phenyl)ethynyl)phenyl)thiazol-2-yl)-4-((4-methylpiperazin-1-yl)methyl)benzamide;
4-((4-methylpiperazin-1-yl)methyl)-N-(4-(3-((2-(trifluoromethyl)phenyl)ethynyl)phenyl)thiazol-2-yl)benzamide;
N-(4-(3,4-bis((2-(trifluoromethyl)phenyl)ethynyl)phenyl)thiazol-2-yl)-4-((4-methylpiperazin-1-yl)methyl)benzamide;
N-(4-(4-methyl-3((triisopropylsilyl)ethynyl)phenyl)thiazol-2-yl)-4-((4-methylpiperazin-1-yl)methyl)benzamide;
N-(4-(3-methyl-4-((triisopropylsilyl)ethynyl)phenyl)thiazol-2-yl)-4-((4-methylpiperazin-1-yl)methyl)benzamide;
N-(4-(3,4-bis((triisopropylsilyl)ethynyl)phenyl)thiazol-2-yl)-4-((4-methylpiperazin-1-yl)methyl)benzamide;
4-((4-methylpiperazin-1-yl)methyl)-N-(4-(3(triethylsilyl)ethynyl)phenyl)thiazol-2-yl)benzamide;
4-((4-methylpiperazin-1-yl)methyl)-N-(4-(3-((trimethylsilyl)ethynyl)phenyl)thiazol-2-yl)benzamide;
N-(4-(3-(cyclohex-1-en-1-ylethynyl)phenyl)thiazol-2-yl)-4((4-methylpiperazin-1-yl)methyl)benzamide;
N-(4-(3-(hex-1-yl-1-yl)phenyl)thiazol-2-yl)-4-((4-methylpiperazin-1-yl)methyl)benzamide;
N-(4-(3-(3-((tert-butyldiphenylsilyl)oxy)prop-1-yn-1-yl)phenyl)thiazol-2-yl)-4-((4-methylpiperazin-1-yl)methyl)benzamide;
4-((4-methylpiperazin-1-yl)methyl)-N-(4-(3-(3-((triisopropylsilyl)oxy)prop-1-yn-1-yl)phenyl)thiazol-2-yl)benzamide;
N-(4-(3-(3-((tert-butyldimethylsilyl)oxy)prop-1-yn-1-yl)phenyl)thiazol-2-yl)-4((4methylpiperazin-1-yl)methyl)benzamide;
N-(4-(3-((tert-butyldimethylsilyl)ethynyl)phenyl)thiazol-2-yl)-4((4-methylpiperazin-1-yl)methyl)benzamide;
N-(4-(3-((tert-butyldiphenylsilyl)ethynyl)phenyl)thiazol-2-yl)-4-((4-methylpiperazin-1-yl)methyl)benzamide;
5-(4-(4-methylpiperazine-1-carbonyl)phenyl)-N-(4-(3-((triisopropylsilyl)ethynyl)phenyl)thiazol-2-yl)furan-2-carboxamide;
N-(4-(3-((tert-butyldimethylsilyl)ethynyl)phenyl)thiazol-2-yl)-5-(4-(4-methylpiperazine-1-carbonyl)phenyl)furan-2-carboxamide;
5-(4-(4-methylpiperazine-1-carbonyl)phenyl)-N-(4-(3-(3-((triisopropylsilyl)oxy)prop-1-yn-1-yl)phenyl)thiazol-2-yl)furan-2-carboxamide;
5-(4-(4-methylpiperazine-1-carbonyl)phenyl)-N-(4-(3((2-(trifluoromethyl)phenyl)ethynyl)phenyl)thiazol-2-yl)furan-2-carboxamide;
4-((4-methylpiperazin-1-yl)methyl)-N-(4-(3-(3-(trityloxy)prop-1-yn-1-yl)phenyl)thiazol-2-yl)benzamide;
N-(4-(3((2-fluorophenyl)ethynyl)phenyl)thiazol-2-yl)-4-((4-methylpiperazin-1-yl)methyl)benzamide;
N-(4-(3((4-fluorophenyl)ethynyl)phenyl)thiazol-2-yl)-4-((4-methylpiperazin-1-yl)methyl)benzamide;
N-(4-(3-((3,5-bis(trifluoromethyl)phenyl)ethynyl)phenyl)thiazol-2-yl)-4((4-methylpiperazin-1-yl)methyl)benzamide;
N-(4-(3((3,5-bis(trifluoromethyl)phenyl)ethynyl)phenyl)thiazol-2-yl)-5-(4-(4-methylpiperazine-1-carbonyl)phenyl)furan-2-carboxamide;
4((4-methylpiperazin-1-yl)methyl)-N-(4-(4-((triisopropylsilyl)ethynyl)phenyl)thiazol-2-yl)benzamide;
N-(4-(4-((3,5-bis(trifluoromethyl)phenyl)ethynyl)phenyl)thiazol-2-yl)-4-((4-methylpiperazin-1-yl)methyl)benzamide;
N-(4-(4-((tert-butyldimethylsilyl)ethynyl)phenyl)thiazol-2-yl)-4-((4-methylpiperazin-1-yl)methyl)benzamide;
4-(morpholinomethyl)-N-(4-(3-((triisopropylsilyl)ethynyl)phenyl)thiazol-2-yl)benzamide;
N-(4-(3((3,5-bis(trifluoromethyl)phenyl)ethynyl)phenyl)thiazol-2-yl)-4-(morpholinomethyl)benzamide;

N-(4-(3-((tert-butyldimethylsilyl)ethynyl)phenyl)thiazol-2-yl)-4-(morpholinomethyl)benzamide;
N-(4-(3-((tert-butyldiphenylsilyl)ethynyl)phenyl)thiazol-2-yl)-4-(morpholinomethyl)benzamide;
4((4-methylpiperazin-1-yl)methyl)-N-(4-(3-((2-(trifluoromethoxy)phenyl)ethynyl)phenyl)thiazol-2-yl)benzamide;
5-(4-(4-methylpiperazine-1-carbonyl)phenyl)-N-(4-(3-((2-(trifluoromethoxy)phenyl)ethynyl)phenyl)thiazol-2-yl)furan-2-carboxamide;
4-(((2-(dimethylamino)ethyl)amino)methyl)-N-(4-(3-((triisopropylsilyl)ethynyl)phenyl)thiazol-2-yl)benzamide;
4-((1H-tetrazol-1-yl)methyl)-N-(4-(3-((triisopropylsilyl)ethynyl)phenyl)thiazol-2-yl)benzamide;
4-((1H-imidazol-1-yl)methyl)-N-(4-(3-((triisopropylsilyl)ethynyl)phenyl)thiazol-2-yl)benzamide;
isopropyl 2-((4((4-(3-((triisopropylsilyl)ethynyl)phenyl)thiazol-2-yl)carbamoyl)benzyl)amino)acetate;
4((4-methylpiperazin-1-yl)methyl)-N-(4-(3-((triisopropylsilyl)ethynyl)phenyl)thiazol-2-yl)benzamide;
N-(4-(3-ethynylphenyl)thiazol-2-yl)-4-((4-methylpiperazin-1-yl)methyl)benzamide and
4-((4-(prop-2-yn-1-yl)piperazin-1-yl)methyl)-N-(4-(3-((triisopropylsilyl)ethynyl)phenyl)thiazol-2-yl)benzamide.

\* \* \* \* \*